(12) United States Patent
Mann et al.

(10) Patent No.: US 11,474,103 B2
(45) Date of Patent: Oct. 18, 2022

(54) SYSTEMS FOR DETECTION

(71) Applicant: KONIKU INC., Berkely, CA (US)

(72) Inventors: Winston Mann, San Francisco, CA (US); Renaud Renault, Fremont, CA (US); Jean-Charles Neel, San Francisco, CA (US); Michael Siani-Rose, San Francisco, CA (US); Oshiorenoya Agabi, Dublin, CA (US)

(73) Assignee: KONIKU INC., San Rafael, CA (US)

(*) Notice: Subject to any disclaimer, the term of this patent is extended or adjusted under 35 U.S.C. 154(b) by 10 days.

(21) Appl. No.: 16/486,132

(22) PCT Filed: Feb. 16, 2018

(86) PCT No.: PCT/US2018/000027
§ 371 (c)(1),
(2) Date: Aug. 14, 2019

(87) PCT Pub. No.: WO2018/208332
PCT Pub. Date: Nov. 15, 2018

(65) Prior Publication Data
US 2021/0333270 A1    Oct. 28, 2021

Related U.S. Application Data

(60) Provisional application No. 62/460,711, filed on Feb. 17, 2017.

(51) Int. Cl.
G01N 33/543    (2006.01)
G16B 25/30    (2019.01)
G01N 33/50    (2006.01)

(52) U.S. Cl.
CPC ..... G01N 33/5438 (2013.01); G01N 33/5058 (2013.01); G16B 25/30 (2019.02)

(58) Field of Classification Search
CPC .................. G01N 33/5438; G01N 33/5058
See application file for complete search history.

(56) References Cited

U.S. PATENT DOCUMENTS

| | | | |
|---|---|---|---|
| 4,444,206 | A | 4/1984 | Gold |
| 7,195,899 | B1 | 3/2007 | Chin et al. |
| 7,241,881 | B2 | 7/2007 | Vosshall et al. |
| 7,541,155 | B2 | 6/2009 | Enan |
| 7,550,574 | B2 | 6/2009 | Lee et al. |
| 7,601,829 | B2 | 10/2009 | Lee et al. |

(Continued)

FOREIGN PATENT DOCUMENTS

| | | |
|---|---|---|
| CN | 2862957 Y | 1/2007 |
| EP | 2730645 A2 | 5/2014 |

(Continued)

OTHER PUBLICATIONS

JPO, Notice of Reasons for Rejection dated Nov. 29, 2021 for Japanese Application No. 2019-544719, 75 pages.

(Continued)

*Primary Examiner* — Melanie Brown
(74) *Attorney, Agent, or Firm* — Perkins Coie LLP

(57) ABSTRACT

Cell-based sensor devices, systems, and methods for the detection and identification of volatile compounds, and for the determination of the location of the source of the volatile compounds in an enclosed space are described.

14 Claims, 15 Drawing Sheets

(56) References Cited

U.S. PATENT DOCUMENTS

| | | |
|---|---|---|
| 7,618,829 B2 | 11/2009 | Keizer et al. |
| 7,795,039 B2 | 9/2010 | Spira et al. |
| 7,919,319 B2 | 4/2011 | Jervis et al. |
| 8,333,860 B1 | 12/2012 | Bibi et al. |
| 8,865,464 B2 | 10/2014 | Takayama et al. |
| 9,068,281 B2 | 6/2015 | Wu et al. |
| 10,209,239 B1 | 2/2019 | Hanson et al. |
| 2002/0020666 A1* | 2/2002 | Cote ............ C02F 3/308 210/615 |
| 2002/0050611 A1 | 5/2002 | Yitzchaik et al. |
| 2003/0008331 A1 | 1/2003 | Lerner |
| 2003/0082795 A1 | 5/2003 | Shuler |
| 2004/0096960 A1 | 5/2004 | Burd et al. |
| 2004/0101851 A1 | 5/2004 | White et al. |
| 2004/0219074 A1 | 11/2004 | Childers et al. |
| 2006/0073483 A1 | 4/2006 | White et al. |
| 2006/0166354 A1 | 7/2006 | Wikswo et al. |
| 2006/0172279 A1 | 8/2006 | Smela et al. |
| 2007/0054266 A1 | 3/2007 | Sato et al. |
| 2007/0099173 A1 | 5/2007 | Spira et al. |
| 2007/0161106 A1 | 7/2007 | Jervis et al. |
| 2008/0138797 A1 | 6/2008 | Hunt et al. |
| 2009/0023608 A1 | 1/2009 | Hung et al. |
| 2009/0029403 A1 | 1/2009 | Fleischer et al. |
| 2010/0160999 A1 | 6/2010 | Epstein et al. |
| 2010/0248268 A1 | 9/2010 | Woods et al. |
| 2011/0086427 A1 | 4/2011 | Faris et al. |
| 2011/0111500 A1 | 5/2011 | Chen |
| 2013/0059322 A1 | 3/2013 | Hung et al. |
| 2013/0115606 A1 | 5/2013 | Hansen et al. |
| 2013/0143230 A1 | 6/2013 | Tolias et al. |
| 2014/0308688 A1 | 10/2014 | Grego et al. |
| 2015/0004077 A1 | 1/2015 | Wikswo et al. |
| 2015/0018226 A1 | 1/2015 | Hansen et al. |
| 2017/0002315 A1 | 1/2017 | Urisu et al. |
| 2017/0015964 A1 | 1/2017 | Agabi |
| 2017/0326381 A1 | 11/2017 | Kozai et al. |

FOREIGN PATENT DOCUMENTS

| | | | |
|---|---|---|---|
| JP | 2003533221 A | | 11/2003 |
| JP | 2004081085 A | | 3/2004 |
| JP | 2005532060 A | | 10/2005 |
| JP | 2006-61048 A | | 3/2006 |
| JP | 2006527380 A | | 11/2006 |
| JP | 2007515958 A | | 6/2007 |
| JP | 2008-529540 A | | 8/2008 |
| JP | 2009524407 A | | 7/2009 |
| JP | 2009-270980 A | | 11/2009 |
| JP | 2010130966 A | | 6/2010 |
| JP | 2011-7741 A | | 1/2011 |
| JP | 2013-27376 A | | 2/2013 |
| JP | 2016536983 A | | 12/2016 |
| JP | 2017500062 A | | 1/2017 |
| WO | 9205243 A1 | | 4/1992 |
| WO | 9614933 A1 | | 5/1996 |
| WO | 2002068473 A1 | | 9/2002 |
| WO | 03100057 A1 | | 12/2003 |
| WO | 2004008922 A2 | | 1/2004 |
| WO | 2005059088 A1 | | 6/2005 |
| WO | 2006136953 A2 | | 12/2006 |
| WO | 2010009307 A2 | | 1/2010 |
| WO | 2013086502 A1 | | 6/2013 |
| WO | 2016030378 A1 | | 3/2016 |
| WO | 2017015148 A1 | | 1/2017 |
| WO | 2018081657 A2 | | 5/2018 |

OTHER PUBLICATIONS

Oh et al., "Cell-Based High-Throughput Odorant Screening System Through Visualization on a Microwell Array"; Biosensors and Bioelectronics, vol. 53, pp. 18-25. (Year 2014).

Toda, et al., "Establishment of a New Cell-Based Assay to Measure the Activity of Sweeteners in Fluorescent Food Extracts"; Journal of Agriculture and Food Chemistry, vol. 59, pp. 12131-12138. (Year 2011).

Son et al., "Bioelectronic Nose: An Emerging Tool for Odor Standardization", Trends in Biotechnology, (Apr. 1, 2017), vol. 35, No. 4, doi:10.1016/j.tibtech.2016.12.007, pp. 301-307, XP029948716 [A] 1-5, 18-22, 35-41, 54-57, 83-86, 117-143.

Wasilewski et al., "Bioelectronic Nose: Current Status and Perspectives", Biosensors and Bioelectronics, (Aug. 26, 2016), vol. 87, pp. 480-494, XP055643569 [A] 1-5, 18-22, 35-41, 54-57, 83-86, 117-143.

PCT/US2018/000027, International Search Report dated Nov. 2, 2018.

Dweck, HK., et al. "Olfactory preference for egg laying on citrus substrates in *Drosophila*" Curr. Biol. 2013, 23(24), pp. 2472-2480.

Grosse-Wilde, E. et al. "Sex-specific odorant receptors of the tobacco hornworm *Manduca sexta*" Front. Cell. Neurosci. 2010, 4, pp. 22.

Ling et al. "The Fabrication of an Olfactory Receptor Neuron Chip Based on Planar Multi-Electrode Array and its Odor-Response Analysis" Biosens. Bioelectron., 2010, 26(3), pp. 1124-1128.

Mukhopadhyay "When microfluidic devices go bad" 2005, Annals of Chemistry, 77(21), pp. 429-432.

Northey, T. et al. "Crystal Structures and Binding Dynamics of Odorant-Binding Protein 3 from two aphid species *Megoura viciae* and *Nasonovia rbisnigri*" Sci. Rep. 2016, 6:24739.

Termtanasombat et al. "Cell-Based Odorant Sensor Array for Odor Discrimination Based on Insect Odorant Receptors" J. Chem. Ecol., 2016, 42(7), pp. 716-724.

Zhang, Z. et al. "A Female-Biased Odorant Receptor from Apolygus lucorum (Meyer-Dur) Tune to Some Plant Odors" Int. J. Mol. Sci. 2016, 17(8), E1165.

Zhou, J. et al. "Identification of Host-Plant Volatiles and Characterization of Two Novel General Odorant-Binding Proteins from the Legume Pod Borer, Maruca vitrata Fabricius (Lepidoptera: Crambidae)." PLoS ONE, 2015, 10(10), e0141208.

* cited by examiner

SYSTEMS FOR DETECTION

CROSS-REFERENCE TO RELATED APPLICATIONS

This application is a 35 USC § 371 National Stage application of International Application No. PCT/US2018/000027 filed Feb. 16, 2018, which claims the benefit under 35 USC § 119(e) to U.S. Application Ser. No. 62/460,711 filed Feb. 17, 2017. The disclosure of each of the prior applications is considered part of and is incorporated by reference in the disclosure of this application.

BACKGROUND

Cellular arrays are of utility in medical research and life sciences in general. Traditional cellular arrays use simple containers such as a petri dish or multi-well plate as a vessel for cell culture. However, it is recognized in the art that such a simple approach provides cells with a substantially different environment to that experienced by cells in vivo.

SUMMARY

Disclosed herein are systems comprising: a) at least one sensor panel located within a space, wherein the at least one sensor panel comprises one or more cell-based sensor devices, and wherein each cell-based sensor device comprises: i) a plurality of chambers, wherein each of the plurality of chambers comprises a cell expressing one or more cell-surface receptors, and wherein, when a binding event occurs between one or more of the cell-surface receptors of the cell and a compound present in air within the space, an electrical signal results in response to the binding; and ii) at least one electrode positioned within each chamber of the plurality of chambers to form a plurality of electrodes configured to measure electrical signals; and b) a controller configured to receive the electrical signals measured by the plurality of electrodes in each cell-based sensor device of the at least one sensor panel, wherein the controller stores and processes a pattern of electrical signals associated with the compound that is generated by at least one of the cell-based sensor devices of the at least one sensor panel to identify the compound.

In some embodiments, the system comprises two or more sensor panels located at different known positions within the space, and the controller is further configured to determine a spatial location of a source of the compound within the space. In some embodiments, the one or more cell-based sensor devices or the at least one sensor panel further comprise a semi-permeable gas exchange membrane configured to facilitate transfer of compounds present in the air to a liquid medium that bathes the cells in each of the chambers in each cell-based sensor device of the corresponding sensor panel. In some embodiments, the system further comprises one or more air sampling devices, wherein each air sampling device is in fluid communication with a sensor panel, and wherein each air sampling device is configured to facilitate transfer of compounds present in the air to a liquid medium that bathes the cells in each of the chambers in each cell-based sensor device of the corresponding sensor panel. In some embodiments, at least one of the one or more air sampling devices comprises a semi-permeable gas exchange membrane that retains the liquid medium that bathes the cells but allows diffusion of the compound from air into the liquid medium. In some embodiments, the surface area-to-volume ratio for the semi-permeable membrane and the volume of liquid medium in contact with the semi-permeable membrane at a given instant is greater than 10 $cm^{-1}$. In some embodiments, the surface area-to-volume ratio for the semi-permeable membrane and the volume of liquid medium in contact with the semi-permeable membrane at a given instant is greater than 100 $cm^{-1}$. In some embodiments, the surface area-to-volume ratio for the semi-permeable membrane and the volume of liquid medium in contact with the semi-permeable membrane at a given instant is greater than 1,000 $cm^{-1}$. In some embodiments, at least one of the air sampling devices comprises a pressurized gas chamber for injecting pressurized air into a closed mixing chamber to increase the partial pressure of the compound above a volume of liquid medium that is subsequently injected into the plurality of chambers in each cell-based sensor device. In some embodiments, at least one of the air sampling devices comprises a heating chamber in which the liquid medium is heated prior to exposure to or mixing with air, and wherein the liquid medium is subsequently cooled prior to being used to bathe the cells. In some embodiments, at least one of the air sampling devices comprises a solvent chamber in which air is mixed with a solvent for which the solubility of the compound is high, and which is subsequently mixed with the liquid medium bathing the cells. In some embodiments, the solvent is dimethyl sulfoxide (DMSO). In some embodiments, at least one of the one or more air sampling devices comprises a perfusion chamber configured to facilitate diffusion of the compound from air into the liquid medium. In some embodiments, at least one of the one or more air sampling devices comprises an atomizer configured to facilitate diffusion of the compound from air into the liquid medium. In some embodiments, the compound is a volatile compound. In some embodiments, the compound is a volatile organic compound. In some embodiments, a pattern of electrical signals generated by a cell-based sensor device comprises one or more electrical signals generated by one or more cells within the cell-based sensor device, such that exposure to a compound or mixture of compounds produces a unique pattern of electrical signals. In some embodiments, the controller processes the pattern of electrical signals using a machine learning algorithm to facilitate the identification of the compound. In some embodiments, the machine learning algorithm comprises an artificial neural network or deep learning algorithm. In some embodiments, the artificial neural network or deep learning algorithm is trained using a training dataset comprising patterns of electrical signals generated by a cell-based sensor device upon exposure to a series of known concentrations of the compound. In some embodiments, the training dataset further comprises patterns of electrical signals generated by a cell-based sensor device upon exposure to a series of known concentrations of the compound in the presence of a mixture of different compounds. In some embodiments, the cell is a neuron. In some embodiments, the electrical signals comprise an action potential. In some embodiments, the electrical signals comprise an excited electrical signal level that is below a threshold for an action potential. In some embodiments, the electrical signals comprise a cell membrane depolarization. In some embodiments, a cell in each of the plurality of chambers is modified to express one or more cell-surface receptors. In some embodiments, a cell in each of the plurality of chambers is genetically modified to express one or more cell-surface receptors. In some embodiments, a cell in each of the plurality of chambers is modified or genetically modified to express one or more different cell-surface receptors. In some embodiments, each individual cell-based sensor device is configured to detect a different compound or mixture of compounds. In some embodiments, each of the at least one sensor panels comprises a single cell-based sensor device. In some embodiments, each of the at least one sensor panels comprises four or more cell-based sensor devices. In some embodiments, each of the at least one sensor panels comprises eight or more cell-based sensor devices. In some embodiments, the compound comprises any combination of odorant compounds from Table 1a. In some embodiments, the one or more cell-surface receptors are odorant receptors. In some embodiments, the odorant receptor comprise any combination of odorant receptors from Table 1b. In some embodiments, the odorant receptor comprises OR1A1, MOR106-1, OR51E1, OR10J5, OR51E2, MOR9-1, MOR18-1, MOR272-1, MOR31-1, MOR136-1, or any fragment thereof, or any combination thereof. In some embodiments, the odorant receptor comprises any combination of odorant receptors from Table 2. In some embodiments, the odorant receptor comprises any combination of odorant receptors from Table 3. In some embodiments, the odorant receptor comprises any combination of odorant receptors from Table 4. In some embodiments, the odorant receptor comprises at least 2 odorant receptors from of Table 1b. In some embodiments, the odorant receptor comprises at least 2 odorant receptors from Table 2. In some embodiments, the odorant receptor comprises at least 2 odorant receptors from Table 3. In some embodiments, the compound comprises any combination of volatile compounds from Table 5. In some embodiments, the space is an airport, a train station, a bus station, a sports arena, a performing arts center, a school, a medical facility, or any combination thereof. In some embodiments, the space is a public space. In some embodiments, the controller processes time-stamped patterns of electrical signals received from at least one of the cell-based sensor devices of each of the two or more sensor panels, and data for the known positions of the two or more sensor panels, to determine the spatial location of the source of the compound using a triangulation procedure. In some embodiments, the controller processes time-stamped patterns of electrical signals received from at least one of the cell-based sensor devices of each of the two or more sensor panels, and data for the known positions of the two or more sensor panels, using a machine learning algorithm to improve the accuracy of determining the spatial location of the source of the compound. In some embodiments, the machine learning algorithm is an artificial neural network or deep learning algorithm. In some embodiments, the artificial neural network or deep learning algorithm is trained using a training dataset comprising time-stamped data for the pattern of electrical signals received from at least one cell-based sensor device for each of two or more sensor panels located at known positions within the space, wherein the data are generated using a compound source located at a known position within the space. In some embodiments, the spatial location of the source is accurate to within about 0.01 meters to about 1.0 meters in any dimension. In some embodiments, a concentration detection limit for the compound detected by a cell-based sensor device ranges from about 1 part per billion (ppb) to about 100 parts per million (ppm).

Also disclosed herein are methods for detecting and identifying a volatile compound in an air sample, the method comprising: a) providing at least one sensor panel, wherein the at least one sensor panel comprises one or more cell-based sensor devices, and wherein each cell-based sensor device comprises: i) a plurality of chambers, wherein each of the plurality of chambers comprises a cell expressing one or more cell-surface receptors, and wherein, when a binding event occurs between one or more of the cell-surface receptors of the cell and a compound present in the air sample, an electrical signal results in response to the binding; and ii) at least one electrode positioned within each chamber of the plurality of chambers to form a plurality of electrodes configured to measure electrical signals; b) contacting the at least one sensor panel with the air sample; and c) processing a pattern of electrical signals measured by the plurality of electrodes to detect and identify the compound.

In some embodiments, the cell is a neuron. In some embodiments, the electrical signals comprise an action potential. In some embodiments, the electrical signals comprise an excited electrical signal level that is below a threshold for an action potential. In some embodiments, the electrical signals comprise a cell membrane depolarization. In some embodiments, a cell in each of the plurality of chambers is genetically-modified to express one or more cell-surface receptors. In some embodiments, each chamber of the plurality of chambers comprises a cell that is genetically-modified to express a different cell-surface receptor. In some embodiments, the one or more cell surface receptors are odorant receptors. In some embodiments, the odorant receptors comprise any combination of receptors listed in Table 1b, Table 2, Table 3, or Table 4. In some embodiments, the volatile compound comprises any combination of odorant compounds from Table 1a or Table 5. In some embodiments, the processing step comprises the use of a machine learning algorithm for improving the accuracy of detecting and identifying the compound. In some embodiments, the machine learning algorithm comprises a support vector machine learning algorithm, an artificial neural network, a deep learning neural network, or any combination thereof. In some embodiments, the method is used to detect and identify a volatile marker or taggant for an explosive material.

Disclosed herein are devices comprising: a) a plurality of chambers, wherein each of the plurality of chambers comprises a cell expressing one or more cell-surface receptors, and wherein, when a binding event occurs between one or more of the cell-surface receptors of the cell and a compound introduced into a liquid medium bathing the cells, an electrical signal results in response to the binding; and b) at least one electrode positioned within each chamber of the plurality of chambers to form a plurality of electrodes configured to measure electrical signals; and c) an integrated, semipermeable gas exchange membrane that facilitates diffusion of compounds from a gas into the liquid medium.

Also disclosed herein are devices comprising: a) a plurality of chambers, wherein each of the plurality of chambers comprises a cell expressing one or more cell-surface receptors, and wherein, when a binding event occurs between one or more of the cell-surface receptors of the cell and a compound introduced from a gas into a liquid medium bathing the cells, an electrical signal results in response to the binding; and b) at least one electrode positioned within each chamber of the plurality of chambers to form a plurality of electrodes configured to measure electrical signals.

In some embodiments, the device is directly integrated with, or is in fluidic communication with, a gas-sampling device configured to facilitate transfer of compounds present in the gas to the liquid medium. In some embodiments, the gas-sampling device comprises a pressurized gas chamber for injecting pressurized air into a closed mixing chamber to increase the partial pressure of the compound above a volume of liquid medium that is subsequently injected into the plurality of chambers in each cell-based sensor device. In some embodiments, the gas-sampling device comprises a heating chamber in which the liquid medium is heated prior to exposure to or mixing with the gas, and wherein the liquid medium is subsequently cooled prior to being used to bathe the cells. In some embodiments, the gas-sampling device comprises a solvent chamber in which gas is mixed with a solvent for which the solubility of the compound is high, and which is subsequently mixed with the liquid medium bathing the cells. In some embodiments, the solvent is dimethyl sulfoxide (DMSO). In some embodiments, the gas-sampling device comprises a perfusion chamber configured to facilitate diffusion of the compound from the gas into the liquid medium. In some embodiments, the gas-sampling device comprises an atomizer configured to facilitate diffusion of the compound from the gas into the liquid medium. In some embodiments, the gas is air. In some embodiments, the compound is a volatile compound. In some embodiments, the compound is a volatile organic compound. In some embodiments, a pattern of electrical signals generated by the device comprises one or more electrical signals generated by one or more cells such that exposure to a compound or mixture of compounds produces a unique pattern of electrical signals. In some embodiments, a controller processes a pattern of electrical signals using a machine learning algorithm to facilitate the identification of the compound. In some embodiments, the machine learning algorithm comprises an artificial neural network or deep learning algorithm. In some embodiments, the artificial neural network or deep learning algorithm is trained using a training dataset comprising patterns of electrical signals generated by a cell-based sensor device upon exposure to a series of known concentrations of the compound. In some embodiments, the training dataset further comprises patterns of electrical signals generated upon exposure to a series of known concentrations of the compound in the presence of a mixture of different compounds. In some embodiments, the cell is a neuron. In some embodiments, the electrical signals comprise an action potential. In some embodiments, the electrical signals comprise an excited electrical signal level that is below a threshold for an action potential. In some embodiments, the electrical signals comprise a cell membrane depolarization. In some embodiments, a cell in each of the plurality of chambers is modified to express one or more cell-surface receptors. In some embodiments, a cell in each of the plurality of chambers is genetically modified to express one or more cell-surface receptors. In some embodiments, a cell in each of the plurality of chambers is modified or genetically modified to express one or more different cell-surface receptors. In some embodiments, the compound comprises any combination of odorant compounds from Table 1a. In some embodiments, the one or more cell-surface receptors are odorant receptors. In some embodiments, the odorant receptors comprise any combination of odorant receptors from Table 1b. In some embodiments, the odorant receptor comprises OR1A1, MOR106-1, OR51E1, OR10J5, OR51E2, MOR9-1, MOR18-1, MOR272-1, MOR31-1, MOR136-1, or any fragment thereof, or any combination thereof. In some embodiments, the odorant receptor comprises any combination of odorant receptors from Table 2. In some embodiments, the odorant receptor comprises any combination of odorant receptors from Table 3. In some embodiments, the odorant receptor comprises any combination of odorant receptors from Table 4. In some embodiments, the odorant receptor comprises at least 2 odorant receptors from of Table 1b. In some embodiments, the odorant receptor comprises at least 2 odorant receptors from Table 2. In some embodiments, the odorant receptor comprises at least 2 odorant receptors from Table 3. In some embodiments, the compound comprises any combination of volatile compounds from Table 5.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 2A: cross-sectional view of electrode structure comprising a plurality of protrusions. FIG. 2B: cross-sectional view of electrode comprising a plurality of depressions.

FIG. 3A: front view of electrode structure comprising a plurality of depressions. FIG. 3B: front view of electrode structure comprising a plurality of protrusions.

FIG. 4A: top view. FIG. 4B: side view.

FIG. 5A: top view. FIG. 5B: side view.

FIG. 6A: top view. FIG. 6B: side view.

FIG. 13A: top view. FIG. 13B: side view.

DETAILED DESCRIPTION

Figure 1:
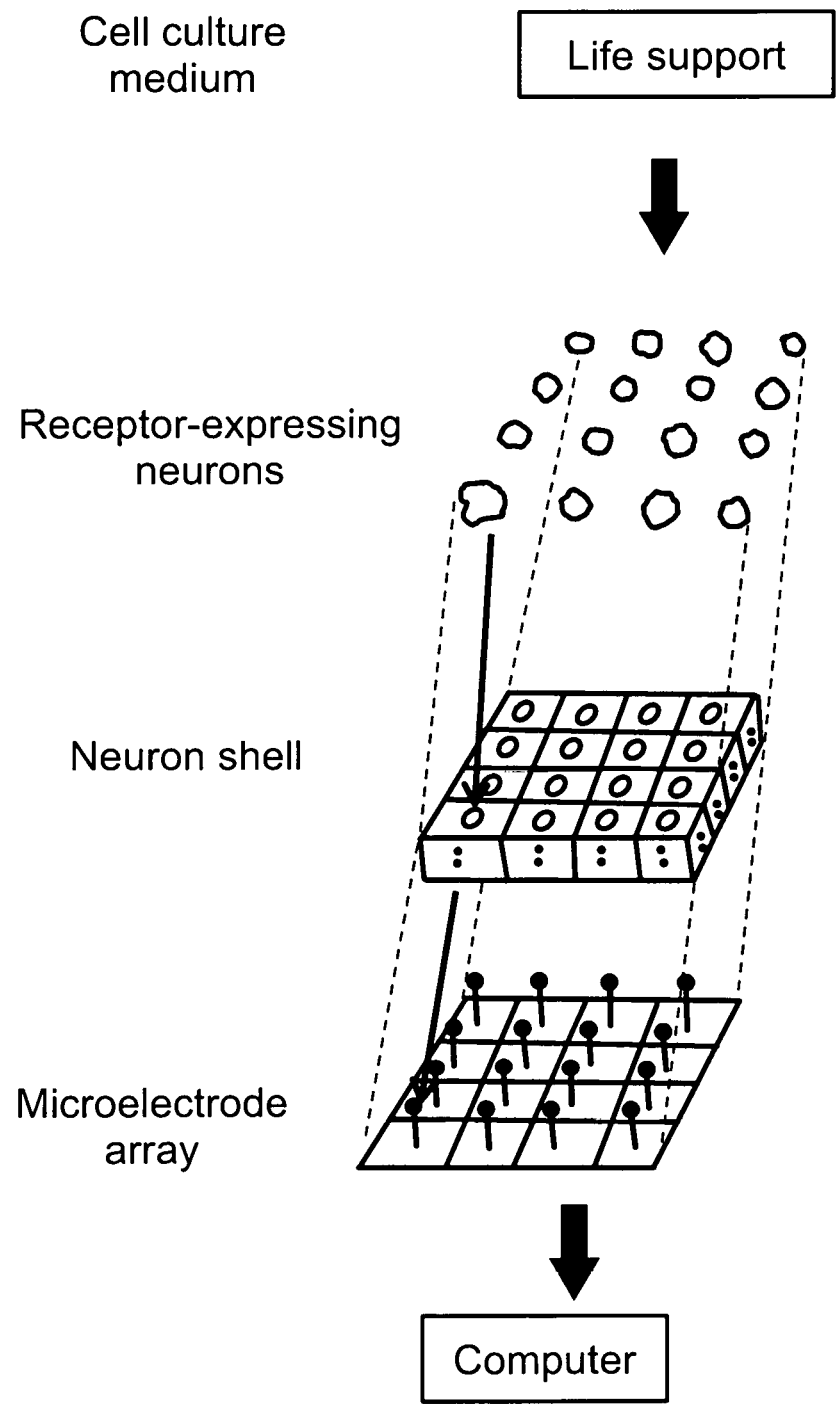
FIG. 1 provides a schematic illustration of a cell-based sensor device comprising an array of cells in contact with a micro electrode array (MEA).

Recently, microfluidic devices that provide for the culturing of cells in carefully-controlled microenvironments that more closely mimic the in vivo environment have been described in the literature. For example, see the cell culture modules and systems described in co-pending patent applications published as US 2017/0015964 A1 and WO 2017/015148 A1. The ability to culture cells and maintain their viability for prolonged periods of time in carefully-controlled microenvironments has application in a variety of fields including basic biomedical research, tissue engineering, biosensor-based detection systems, etc.

Disclosed herein are cell-based sensor devices, sensor panels comprising arrays of one or more cell-based sensor devices, detection systems comprising one or more sensor panels, and methods of use thereof. The disclosed detection systems take advantage of the binding specificity inherent in cell surface receptor-ligand binding interactions and the signal amplification inherent in the signaling pathways of excitable cells to achieve sensitive and specific detection of compounds, e.g., volatile compounds present in air samples drawn from outdoor or indoor (enclosed) environments.

In a first aspect of the present disclosure, cell-based sensor devices are described that comprise a plurality of chambers, wherein each chamber comprises at least one cell expressing one or more cell surface receptors, and at least one electrode configured to measure electrical signals positioned within the chamber. In some embodiments, the cell(s) within each chamber of the device are bathed in a cell culture medium that is continuously, periodically, or randomly perfused through each chamber of the plurality of chambers in order to maintain the viability of the cells therein. Binding events between a compound (or mixture of compounds) introduced into the medium bathing the cells and one or more of the cell surface receptors may give rise to electrical signals, e.g., changes in cell surface electrostatic potentials or cell membrane depolarizations, that are detected by the electrode in the corresponding chamber. In some embodiments, cells in different chambers may comprise different cell surface receptors, or may comprise the same cell surface receptor expressed at different levels, such that the plurality of electrodes associated with the plurality of chambers in the device detect a pattern of electrical signals in response to a binding event that may be recorded and/or processed. In some embodiments, the cell-based sensor device may comprise a processor for processing the patterns of electrical signals detected by the plurality of electrodes. In some embodiments, the processor may be external to the cell-based sensor device. In some embodiments, machine learning-based processing of the patterns of electrical signals may be used to improve the sensitivity and/or specificity of the cell-based sensor device for detection of specific compounds or mixtures of compounds. Some aspects of the disclosed cell-based sensor devices have been described in co-pending PCT Application No. PCT/US17/58895.

In a second aspect of the present disclosure, sensor panels are described which comprise one or more cell-based sensor devices. In some embodiments, the sensor panels may comprise two or more individual cell-based sensor devices, wherein each cell-based sensor device has been designed and/or optimized (e.g., by virtue of choosing the types of cells and/or cell surface receptors expressed in each of the plurality of chambers within each cell-based sensor device) to detect a different compound or mixture of compounds, such that the sensor panel is designed and/or optimized to detect two or more different compounds or mixtures of compounds. In some embodiments, each cell-based sensor device may comprise a processor for processing the patterns of electrical signals detected by plurality of electrodes in each device. In some embodiments, the sensor panel may comprise a processor for processing the patterns of electrical signals detected by the plurality of electrodes in all cell-based sensor devices of the panel. In some embodiments, machine learning-based processing of the patterns of electrical signals recorded by the plurality of electrodes in each of the cell-based sensor devices of the panel is used to improve the sensitivity and/or specificity of the sensor panel for detection of specific compounds or mixtures of compounds, while minimizing signal cross-talk between the individual cell-based sensor devices.

In a third aspect of the present disclosure, detection systems are described which comprise two or more sensor panels. In some embodiments, the two or more sensor panels may comprise the same complement of cell-based sensor devices, i.e., a set of cell-based sensor devices designed and/or optimized for detection of the same set of compounds or mixtures of compounds. In some embodiments, the two or more sensor panels may comprise different complements of cell-based sensor devices, i.e., sets of cell-based sensor devices designed and/or optimized for detection of a different set of compounds or mixtures of compounds. In some embodiments, the two or more sensor panels of the detection system may be positioned at known locations within a defined outdoor or indoor (enclosed) environment. In some embodiments, the detection system may further comprise two or more air sampling devices, wherein each air sampling device is in fluid communication with one of the two or more sensor panels, and wherein each air sampling device is configured to facilitate the transfer compounds present in the air to a liquid medium that bathes the cells in each of the chambers in each cell-based sensor device of the corresponding sensor panel. In some embodiments, the detection system may comprise a controller configured to receive the electrical signals measured by the plurality of electrodes in each cell-based sensor device of the two or more sensor panels. In some embodiments, the controller stores and processes a pattern of electrical signals associated with a compound or mixture of compounds that is generated by at least one of the cell-based sensor devices in each of the two or more sensor panels (which are positioned at known locations) to identify the compound or mixture of compounds and provide a spatial location of a source of the compound or mixture of compounds within an outdoor or indoor (enclosed) environment.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions: As used herein, the singular forms "a", "an", and "the" include plural references unless the context clearly dictates otherwise. Any reference to "or" herein is intended to encompass "and/or" unless otherwise stated.

As used herein, the term "about" means the referenced numeric indication plus or minus 15% of that referenced numeric indication.

The term "cell" as used herein, generally refers to one or more cells. A cell may be obtained or isolated from a subject. A cell may be obtained or isolated from a tissue. A subject may be an animal such as a human, a mouse, a rat, a pig, a dog, a rabbit, a sheep, a horse, a chicken or other animal. A cell may be a neuron. A neuron may be a central neuron, a peripheral neuron, a sensory neuron, an interneuron, a motor neuron, a multipolar neuron, a bipolar neuron, or a pseudo-unipolar neuron. A cell may be a neuron supporting cell, such as a Schwann cell. A cell may be one of the cells of a blood-brain barrier system. A cell may be a cell line, such as a neuronal cell line. A cell may be a primary cell, such as cells obtained from a brain of a subject. A cell may be a population of cells that may be isolated from a subject, such as a tissue biopsy, a cytology specimen, a blood sample, a fine needle aspirate (FNA) sample, or any combination thereof. A cell may be obtained from a bodily fluid such as urine, milk, sweat, lymph, blood, sputum, amniotic fluid, aqueous humour, vitreous humour, bile, cerebrospinal fluid, chyle, chyme, exudates, endolymph, perilymph, gastric acid, mucus, pericardial fluid, peritoneal fluid, pleural fluid, pus, rheum, saliva, sebum, serous fluid, smegma, sputum, tears, vomit, or other bodily fluid. A cell may comprise cancerous cells, non-cancerous cells, tumor cells, non-tumor cells, healthy cells, or any combination thereof. A cell may be a modified cell, such as a genetically modified cell. A modified cell may comprise an addition of one of more cell-surface receptors, such as modified cell-surface receptors. The modified cell-surface receptors may be modified to increase or decrease their ability to bind to a large set of compounds, a small set of compounds, or a specific compound. A modified cell may comprise a deletion of one or more cell-surface receptors.

The term "tissue" as used herein, generally refers to any tissue sample. A tissue may be a sample suspected or confirmed of having a disease or condition. A tissue may be a sample that is genetically modified. A tissue may be a sample that is healthy, benign, or otherwise free of a disease. A tissue may be a sample removed from a subject, such as a tissue biopsy, a tissue resection, an aspirate (such as a fine needle aspirate), a tissue washing, a cytology specimen, a bodily fluid, or any combination thereof. A tissue may comprise cancerous cells, tumor cells, non-cancerous cells, or a combination thereof A tissue may comprise neurons. A tissue may comprise brain tissue, spinal tissue, or a combination thereof. A tissue may comprise cells representative of a blood-brain barrier. A tissue may comprise a breast tissue, bladder tissue, kidney tissue, liver tissue, colon tissue, thyroid tissue, cervical tissue, prostate tissue, lung tissue, heart tissue, muscle tissue, pancreas tissue, anal tissue, bile duct tissue, a bone tissue, uterine tissue, ovarian tissue, endometrial tissue, vaginal tissue, vulvar tissue, stomach tissue, ocular tissue, nasal tissue, sinus tissue, penile tissue, salivary gland tissue, gut tissue, gallbladder tissue, gastrointestinal tissue, bladder tissue, brain tissue, spinal tissue, a blood sample, or any combination thereof.

The term "receptor" as used herein, generally refers to a receptor of a cell. The receptor may be a cell-surface receptor. A cell-surface receptor may be a G coupled protein receptor. A receptor may bind to one or more compounds. A receptor may have a different binding affinity to for each compound to which it binds. A receptor may be modified, such as genetically modified. A receptor may be modified to change the number of compounds to which it may bind. A receptor may be modified to increase the number of different compounds to which it may bind. A receptor may be modified to decrease the number of different compounds to which it may bind. A receptor may bind 1 compound. A receptor may bind 2, 3, 4, 5, 6, 7, 8, 9, 10, 15, 20, 30, 40, 50, 60, 70, 80, 90, 100 compounds or more. A receptor may bind less than 10 compounds. A receptor may bind less than 5 compounds. A receptor may bind at least 5 compounds. A receptor may bind at least 10 compounds. A receptor may bind at least 20 compounds. A receptor may be any receptor or any combination of the receptors listed in Table 1b, Table 2, Table 3, or Table 4. A receptor may be any receptor listed in Table 1b, Table 2, Table 3, Table 4, or any combination thereof, that further comprises a modification.

The term "modification" as used herein, generally refers to a modification to a cell, a modification to a protein, or a modification to a cell receptor. A modification to a cell may include adding one or more receptors, such as modified receptors, to the cell. A modification to a cell may include removing one or more receptors from a cell. A modification to a cell may include modifying one or more receptors that are expressed on the cell. A modification to a protein or cell receptor may include a genetic modification, an enzymatic modification, or a chemical modification. A modification to a protein or cell receptor may include a post-translational modification such as an acylation modification, an acetylation modification, a formylation modification, an alkylation modification, a methylation modification, an arginylation modification, a polyglutamylation modification, a polyglycylation modification, a butyrylation modification, a gamma-carboxylation modification, a glycosylation modification, a malonylation modification, a hydroxylation modification, an iodination modification, a nucleotide addition modification, an oxidation modification, a phosphate ester modification, a propionylation modification, a pyroglutamate formation modification, an S-glutathionylation modification, an S-nitrosylation modification, an S-sulfenylation modification, a succinylation modification, a sulfation modification, a glycation modification, a carbamylation modification, a carbonylation modification, a biotinylation modification, a pegylation modification, or any combination thereof.

The term "compound" as used herein, generally refers to a composition that may produce a signal in a cell, such as an electrical signal. A compound may comprise an odorant. A compound may comprise a compound that binds an odorant receptor or a modified odorant receptor. A compound may comprise a volatile compound. A compound may comprise an organic volatile compound. A compound may comprise a neurotoxin or a toxin. A compound may comprise any compound or mixture thereof the odorant of Table 2a. A compound may comprise a carcinogen. A compound may comprise a chemical weapon, such as a mustard gas, a sarin gas, or a combination thereof. A compound may comprise an illegal substance as defined in 42 United States Code § 12210. A compound may comprise a drug or a pharmaceutical composition or salt thereof. A compound may comprise a protein, a peptide, a nucleic acid, an antibody, an aptamer, a small molecule. A compound may comprise a cell or a cellular fragment. A compound may comprise a tissue or tissue fragment. A compound may comprise a naturally-derived composition or a synthetic composition. A compound may be an explosive compound, such as trinitrotoluene (TNT). A compound may be volatile markeer or taggant for an explosive material. A compound may be a precursor to the compound (such as a chemical precursor), a degradation product of the compound, or a metabolite of the compound, or any combination thereof.

The term "sample" as used herein, generally refers to a sample that may or may not comprise one or more compounds. A sample may be tissue or fluid sample obtained from a subject, such as a human subject. A sample may be a fluid or gas sample obtained from an air space, such as an outdoor air space, an air space adjacent to a deployment of a chemical weapon, or an air space in a residential or commercial setting (i.e., an indoor or enclosed environment). A sample may be a blood sample obtained from a subject. A sample may be a soil sample, such as a sample obtained near a fracking system or oil rig system. A sample may be a sample that may comprise a compound that is an environmental hazard or a health hazard. A sample may be a liquid sample obtained from a water system, such as a river, a stream, a lake, an ocean, or others. A sample may be a food sample or a container system that houses a food sample. A pattern or fingerprint of the systems described herein, may confirm a ripeness of a single piece of food, such as a fruit, or a set of fruit.

The term "signal" as used herein, generally refers to a signal in response to a binding event, for example, a compound binding to a cell-surface receptor of a cell. The signal may be an electrical signal. The signal may be a voltage or a current measurement. The signal may be a change in a cell membrane potential. The signal may be a membrane depolarization. The signal may be an action potential. The signal may be an electrical signal that is subthreshold of an action potential. The signal may be a magnitude of a change in a cell membrane potential, or a magnitude of an action potential. The signal may be the number of action potentials or a train of action potentials. The signal may be a signal measured over a period of time. Information from a signal may be imported into a matrix to form a fingerprint or a pattern of signals. The fingerprint or pattern of signals may be a unique fingerprint. The signal may be a measurement of a amplitude, a period, or a frequency, of a combination thereof of an electrical signal. The signal may be a time length of a refractory period following an action potential. The signal may be a peak voltage of an action potential. The signal may be a time to a peak voltage of an action potential. The signal may be a peak voltage of a membrane depolarization.

Cell-based sensor devices: As noted above, disclosed herein are cell-based sensor devices and methods for use thereof. In some embodiments, the cell-based sensor devices of the present disclosure may comprise a single chamber within which at least one cell expressing one or more cell surface receptors and at least one electrode configured to measure electrical signals are positioned. In some embodiments, the cell-based sensor devices may comprise a plurality of chambers (e.g., an array of chambers), wherein each chamber comprises at least one cell expressing one or more cell surface receptors, and at least one electrode configured to measure electrical signals positioned within the chamber. In some embodiments, the number of chambers within the cell-based sensor device may range from 1 to about 100, or more. In some embodiments, the number of chambers in the cell-based sensor device may be at least 1, at least 5, at least 10, at least 20, at least 30, at least 40, at least 50, at least 60, at least 70, at least 80, at least 90, or at least 100 chambers. In some embodiments, the number of chambers in the cell-based sensor device may be at most 100, at most 90, at most 80, at most 70, at most 60, at most 50, at most 40, at most 30, at most 20, at most 10, at most 5, or at most 1 chamber. Any of the lower and upper values described in this paragraph may be combined to form a range included within the present disclosure, for example, the number of chambers within the cell-based sensor device may range from about 5 to about 20. Those of skill in the art will recognize that number of chambers within the cell-based sensor device may have any value within this range, e.g., 16 chambers. In some embodiments, the plurality of chambers within the cell-based sensor device may be organized as an array of chambers, e.g., and m×n array, where m is the number of rows of chambers and n is the number of columns of chambers in the array.

In some embodiments, the cell-based sensor device may further comprise inlet ports, outlet ports, fluid channels (e.g., inlet channels, outlet channels, perfusion channels, etc.), valves, membranes (e.g., gas exchange membranes, filter membranes, dialysis membranes, or ion exchange membranes), etc., that are fluidically coupled to one or more of the chambers within the cell-based sensor device. In some embodiments, the cell-based sensor device may further comprise a gas exchange membrane comprising a polytetrafluoroethylene (PTFE) membrane having a pore size in the range of 0.2 to 0.5 micrometers.

Any of a variety of cell types known to those of skill in the art may be used in the cell-based sensor devices of the present disclosure. In some embodiments, each chamber of a cell-based sensor device may comprise a single cell. In some embodiments, each chamber of a cell-based sensor device may comprise two cells, three cells, four cells, five cells, ten cells, twenty cells, thirty cells, forty cells, fifty cells, or more. In some embodiments, each chamber of a plurality of chambers within a cell-based sensor device may comprise the same cell or set of cells. In some embodiments, a subset of chambers or all of the chambers of a plurality of chambers with a cell-based sensor device may comprise a different cell or set of cells.

Typically, the cell(s) within each chamber of the device are bathed in a cell culture medium that is continuously, periodically, or randomly perfused through each chamber of the plurality of chambers in order to maintain the viability of the cells therein. The medium may include one or more components, including but not limited to, sodium chloride, glycine, 1-alanine, 1-serine, a neuroactive inorganic salt, 1-aspartic acid, 1-glutamic acid, or any combination thereof. A medium may further include one or more of a pH modulating agent, an amino acid, a vitamin, a supplemental agent, a protein, an energetic substrate, a light-sensitive agent, or any combination thereof. A medium may further include one or more buffering agents. A medium may further include one or more antioxidants.

Typically, the composition and perfusion rate of the cell culture medium, as well as and other operational parameters, e.g., temperature, pH of the medium, $CO_2$ concentration in the medium, etc., are optimized to maintain cell viability of the cell(s) within the chamber(s) of the cell-based sensor device. In some embodiments, the life span of the cells within the device may range from about 1 week to about 1 year. In some embodiments, the life span of cells with the device may be at least 1 week, at least 2 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 1.2 years, at least 1.4 years, at least 1.6 years, at least 1.8 years, or at least 2 years.

In a preferred embodiment, the cells within the chamber(s) of a cell-based sensor device may comprise neurons or other excitable cells, e.g., neurons that have been genetically-engineered to express one or more types of cell surface receptor. Any of a variety of cell surface receptors known to those of skill in the art may be used in the disclosed cell-based sensor device. Examples include, but are not limited to, odorant receptors, taste receptors, light-sensitive ion channels or other photoreceptor proteins, etc. Specific examples of suitable cell surface receptors will be described in more detail below. In some embodiments, the type of neuron used may be the same for each chamber in the plurality of chambers within the cell-based sensor device. In some embodiments, the type of neuron used may be different for different chambers of the plurality of chambers within the cell-based sensor device. In some embodiments, the type of neuron used in the sensor device may be selected base on a low level of naturally occurring cell surface receptors in order to minimize random and or background electrical signal generation. In some embodiments, the neuron used in the sensor device may be a neuron that has been modified, e.g., genetically modified, to suppress or eliminate the expression of naturally occurring cell surface receptors.

In another preferred embodiment, the cell-based sensor devices of the present disclosure may comprise an array of neurons that may be engineered to express cell surface receptors (i.e., odorant receptors) to detect volatile or water soluble odorant compounds. Each neuron within the array may express a single type of chemical sensing protein receptor or multiple types of chemical sensing protein receptors that detect a set of ligands (e.g., odorant compounds). Upon binding of a ligand such as an odorant compound to a cell surface receptor, activation of a series of intracellular signaling proteins or pathways may trigger an action potential by the neuron.

Compounds in fluid or gaseous samples may be introduced to the cell-based sensor device either by mixing with the medium that bathes the cells in the device, or by passive diffusion (e.g., in the case of volatile compounds present in an air sample) through a semi-permeable membrane that is integrated with the sensor device. In some embodiments, the use of an air sampling device may be used to facilitate the introduction of compounds into the cell-based sensor device, as will be discussed in more detail below.

Binding events between a compound (or mixture of compounds) introduced into the medium bathing the cells and one or more of the cell surface receptors present in the cells within the device may give rise to electrical signals, e.g., changes in cell surface electrostatic potentials or cell membrane depolarizations, that are detected by the electrode in each corresponding chamber. In some embodiments, the plurality electrodes associated with the plurality of chambers within the cell-based sensor device (i.e., one or more electrodes per chamber) may comprise a microelectrode array (MEA). FIG. 1 provides a schematic illustration of a cell-based sensor device of the present disclosure that comprises neurons that have been genetically-engineered to express selected cell surface receptors, where the neurons are located within an array of chambers (i.e., "neuron shell") that is in contact with the MEA. In cell-based sensor devices comprising, e.g., neurons, each neuron cell may be associated with (e.g., in close proximity to, connected to, or penetrated by) an electrode in the microelectrode array (MEA), which may permit the detection of depolarization of the neuron membrane following the binding of, e.g., an odorant to the cell surface receptor. This electrical signal generated by the cell may be detected by the electrode and transferred to a processor or computer input device, e.g., a data acquisition board comprising an analog to digital converter. In aggregate, the cells of the cell-based sensor device may differentially detect an array of compounds, which collectively may yield a "fingerprint" of electrical signals used to detect and identify compounds or mixtures of compounds. In some embodiments, the cell-based sensors of the present disclosure may provide qualitative data for the detection and identification of specific compounds or mixtures of compounds. In some embodiments, the cell-based sensors of the present disclosure may provide quantitative data for the detection and identification of specific compounds or mixtures of compounds, for example, the sensor data may provide an measure of the concentration of a specific compound present in an air sample, or the relative concentrations of a mixture of compounds present in an air sample.

In some embodiments, the cell-based sensor device may comprise an array of m×n cells (i.e., within an array of m×n chambers). A single odorant may bind to a cell expressing a single type of odorant receptor. The binding event may then activate a signaling pathway within the cell. If the cell is a neuron, then it may trigger an action potential which can be detected by the electrode inserted in or in close proximity to the cell. If the binding event does not trigger a full action potential, the electrode inserted in or in close proximity to the cell may permit detection of a sub-threshold level electrical signal.

In some embodiments, an array of cells within the sensor device may comprise cells each expressing, e.g., a unique odorant receptor. An odorant may bind differentially across the cells such that each cell generates a different electrical signal, e.g., a different electrical signal level having an amplitude that ranges between zero and that for a full action potential, or a different electrical signal frequency, e.g., a different burst frequency.

Through repeated delivery of a single odorant or set of odorants with known characteristics to the cell-based sensor device, a series of relative signals generated across the array of cells may be observed, detected, or collected. The signal values may be contained within a matrix comprising the different levels of electrical signal detected for each cell, based on sub-threshold and full-threshold electrical signals generated by the neurons.

As noted, the signal levels may be represented in a matrix where each element may represent a real valued amplitude, $a_{ij}$, which may represent the sub-threshold signal level or that for a full on/off action potential, and i and j represent the position coordinates of the cell/electrode combination in the array of the sensor device:

$$a_{00} a_{01} a_{02} a_{03} \ldots a_{0n}$$
$$a_{10} a_{11} a_{12} a_{13} \ldots a_{1n}$$
$$a_{20} a_{21} a_{22} a_{23} \ldots a_{2n}$$
$$a_{30} a_{31} a_{32} a_{33} \ldots a_{3n}$$
$$\ldots$$
$$a_{m0} a_{m1} a_{m2} a_{m3} \ldots a_{mn}$$

In some embodiments, a compound may bind to different receptors at different rates (i.e., with different kinetics), since the binding of a ligand to G protein coupled receptors (GPCRs) requires three dimensional coordination between the molecular features of the ligand and those within the binding site of the receptor. Some receptor binding sites may or may not recognize particular moieties or chemical substituents (e.g., OH, $CH_3$, $NH_2$, or COOH groups, etc.) which may decorate the compound of interest; rather it may be the combination of molecular features of the compound that provide a given ligand the "shape" or conformation that enables binding within a given GPCR binding pocket. Thus, in some cases, different parts, e.g., specific moieties or functional groups, of the ligand may bind to different receptors at different rates or with different affinities and trigger different signals in different cells on the array. In some embodiments, calibration of the sensor device using calibration curves generated by exposing the sensor device to a series of compounds at varying concentration may be used to correct for systematic biases due, for example, to differences in the solubility of the compounds in the liquid medium bathing the cells.

In some embodiments, a single compound may give rise to a fixed set of signal values in the signal level matrix, with a range of amplitude variation across all non-zero values. This may be used as a signal fingerprint for that particular compound.

In some embodiments, a set of compounds (related or unrelated) may have a particular signal fingerprint when mapped against a particular set of receptors in a cell-based sensor device. This signal fingerprint for a set of compounds may represent an overlapping set of the signal fingerprints for binding of individual compounds. That is, one may expect the individual compounds in the set of compounds to bind to more than one receptor in different ways. The entire set may be additive across the array. However, the signals generated by binding of some compounds may mask the signals generated by others. Each combination of compounds may yield a unique signal fingerprint or signature generated by the array of cells within the sensor device.

In some embodiments, there may be a single electrode in each chamber (or microwell) of the cell-based sensor device. In some embodiments there may be two or more electrodes in each chamber of the cell-based sensor device. In some embodiments, there may be at least one electrode, at least two electrodes, at least three electrodes, at least four electrodes, at least five electrodes, at least six electrodes, at least seven electrodes, at least eight electrodes, at least nine electrodes, or at least ten electrodes in each chamber of the plurality of chambers within the sensor device. In some embodiments, a single ground electrode may be placed in contact with the culture medium bathing the cells within the device. In some embodiments, at least one of the electrodes in each chamber of the plurality of chambers within the device may be a ground electrode.

In some embodiments, the electrodes used in the cell-based sensor devices of the present disclosure may comprise two-dimension (i.e., planar) electrodes or three dimensional (e.g., hemispherical) electrodes fabricated from any of a variety of materials known to those of skill in the art. Examples include, but are not limited to, metals, metal alloys, and metal oxides, e.g., aluminum, gold, lithium, copper, graphite, carbon, titanium, brass, silver, platinum, palladium, cesium carbonate, molybdenum (VI) oxide, indium tin oxide (ITO), or any combination thereof.

In some embodiments, the surface of the electrode may comprise a chemically modified gold surface, wherein proteins like laminins, non-specific DNA, peptides, conductive polymers, other chemicals or compounds, or any combination thereof are grafted to the surface to improve neural adhesion and signal quality.

In some embodiments, modifying an electrode surface with a plurality of protrusions, a plurality of recesses, or by adding surface roughness may increase the surface area of the electrode and enhance contact between a cell and the electrode, thereby improving the electrical connection between the cell and the electrode.

In some embodiments, a three-dimensional electrode may comprise a spherical shape, a hemispherical shape, a mushroom shape (i.e., comprising a head portion and a support portion), a rod-like shape, a cylindrical shape, a conical shape, a patch shape, or any combination thereof.

In some embodiments, the width of an electrode (e.g., the width of the narrowest portion of a two-dimensional electrode, or the base or support portion of a three-dimensional electrode) may range from about 1 micrometer ($\mu$m) to about 50 micrometers ($\mu$m). In some embodiments, the width of an electrode may be at least 1 $\mu$m, at least 5 $\mu$m, at least 10 $\mu$m, at least 20 $\mu$m, at least 30 $\mu$m, at least 40 $\mu$m, or at least 50 $\mu$m. In some embodiments, the width of an electrode may be at most 50 $\mu$m, at most 40 $\mu$m, at most 30 $\mu$m, at most 20 $\mu$m, at most 10 $\mu$m, at most 5 $\mu$m, or at most 1 $\mu$m. Any of the lower and upper values described in this paragraph may be combined to form a range included within the present disclosure, for example, the width of an electrode may range from about 10 to about 30 $\mu$m. Those of skill in the art will recognize that the width of an electrode may have any value within this range, e.g., about 22.5 $\mu$m.

In some embodiments, the thickness or height of an electrode (i.e., the thickness of a two-dimensional electrode, or the height of a three-dimensional electrode relative to the substrate on which it is fabricated) may range from about 0.1 micrometer ($\mu$m) to about 50 micrometers ($\mu$m). In some embodiments, the thickness or height of an electrode may be at least 0.1 $\mu$m, at least 1 $\mu$m, at least 5 $\mu$m, at least 10 $\mu$m, at least 20 $\mu$m, at least 30 $\mu$m, at least 40 $\mu$m, or at least 50 $\mu$m. In some embodiments, the thickness or height of an electrode may be at most 50 $\mu$m, at most 40 $\mu$m, at most 30 $\mu$m, at most 20 $\mu$m, at most 10 $\mu$m, at most 5 $\mu$m, at most 1 $\mu$m, or at most 0.1 $\mu$m. Any of the lower and upper values described in this paragraph may be combined to form a range included within the present disclosure, for example, the thickness or height of an electrode may range from about 0.1 to about 10 $\mu$m. Those of skill in the art will recognize that the thickness or height of an electrode may have any value within this range, e.g., about 28.6 $\mu$m.

In some embodiments, an electrode may have a surface density of protrusions ranging from about 0.0001 protrusions per square micrometer (pro/$\mu$m$^2$) to about 10 protrusions per square micrometer (pro/$\mu$m$^2$). In some embodiments, the surface density of protrusions on an electrode may be at least 0.0001, at least 0.0005, at least 0.001, at least 0.002, at least 0.003, at least 0.004, at least 0.005, at least 0.006, at least 0.007, at least 0.008, at least 0.009, at least 0.01, at least 0.02, at least 0.03, at least 0.04, at least 0.05, at least 0.06, at least 0.07, at least 0.08, at least 0.09, at least 0.1, at least 0.2, at least 0.3, at least 0.4, at least 0.5, at least 0.6, at least 0.7, at least 0.8, at least 0.9, at least 1, at least 1.1, at least 1.2, at least 1.3, at least 1.4, at least 1.5, at least 2, at least 3, at least 4, at least 5, at least 6, at least 7, at least 8, at least 9, or at least 10 protrusions per square micrometer. In some embodiments, the surface density of protrusions on an electrode may be at most 10, at most 9, at most 8, at most 7, at most 6, at most 5, at most 4, at most 3, at most 2, at most 1.5, at most 1.4, at most 1.3, at most 1.2, at most 1.1, at most 1, at most 0.9, at most 0.8, at most 0.7, at most 0.6, at most 0.5, at most 0.4, at most 0.3, at most 0.2, at most 0.1, at most 0.09, at most 0.08, at most 0.07, at most 0.06, at most 0.05, at most 0.04, at most 0.03, at most 0.02, at most 0.01, at most 0.009, at most 0.008, at most 0.007, at most 0.006, at most 0.005, at most 0.004, at most 0.003, at most 0.002, at most 0.001, at most 0.0005, or at most 0.0001 protrusions per square micrometer. Any of the lower and upper values described in this paragraph may be combined to form a range included within the present disclosure, for example, the surface density of protrusions on an electrode may range from about 0.001 to about 1.1 protrusions per square micrometer. Those of skill in the art will recognize that the surface density of protrusions on an electrode may have any value within this range, e.g., about 0.015 protrusions per square micrometer.

Similarly, in some embodiments, an electrode may have a surface density of recesses ranging from about 0.0001 recesses per square micrometer (recesses/$\mu m^2$) to about 10 recesses per square micrometer (recesses/$\mu m^2$). In some embodiments, the surface density of recesses on an electrode may be at least 0.0001, at least 0.0005, at least 0.001, at least 0.002, at least 0.003, at least 0.004, at least 0.005, at least 0.006, at least 0.007, at least 0.008, at least 0.009, at least 0.01, at least 0.02, at least 0.03, at least 0.04, at least 0.05, at least 0.06, at least 0.07, at least 0.08, at least 0.09, at least 0.1, at least 0.2, at least 0.3, at least 0.4, at least 0.5, at least 0.6, at least 0.7, at least 0.8, at least 0.9, at least 1, at least 1.1, at least 1.2, at least 1.3, at least 1.4, at least 1.5, at least 2, at least 3, at least 4, at least 5, at least 6, at least 7, at least 8, at least 9, or at least 10 recesses per square micrometer. In some embodiments, the surface density of recesses on an electrode may be at most 10, at most 9, at most 8, at most 7, at most 6, at most 5, at most 4, at most 3, at most 2, at most 1.5, at most 1.4, at most 1.3, at most 1.2, at most 1.1, at most 1, at most 0.9, at most 0.8, at most 0.7, at most 0.6, at most 0.5, at most 0.4, at most 0.3, at most 0.2, at most 0.1, at most 0.09, at most 0.08, at most 0.07, at most 0.06, at most 0.05, at most 0.04, at most 0.03, at most 0.02, at most 0.01, at most 0.009, at most 0.008, at most 0.007, at most 0.006, at most 0.005, at most 0.004, at most 0.003, at most 0.002, at most 0.001, at most 0.0005, or at most 0.0001 recesses per square micrometer. Any of the lower and upper values described in this paragraph may be combined to form a range included within the present disclosure, for example, the surface density of recesses on an electrode may range from about 0.005 to about 1.6 recesses per square micrometer. Those of skill in the art will recognize that the surface density of recesses on an electrode may have any value within this range, e.g., about 0.68 recesses per square micrometer.

In some embodiments, the surface of an electrode may be smooth. In some embodiments, the surface of an electrode may have a surface roughness. A surface roughness may be uniform across the surface of an electrode. A portion of the surface of an electrode may have a surface roughness, such as a top portion of the electrode, or a bottom portion of the electrode. An electrode may have alternating rows of smooth and rough portions.

In some embodiments, a surface roughness may be about 5, 10, 15, 20, 25, 30, 35, 50, 100, 200, 300, 400, 500, 600, 700, 800, 900, 1000, 1500, 2000, 2500, 3000 nanometers (nm) or more. In some embodiments, a surface roughness may be from about 5 to about 50 nm. In some embodiments, a surface roughness may be from about 5 to about 100 nm. In some embodiments, a surface roughness may be from about 5 to about 500 nm. In some embodiments, a surface roughness may be from about 10 to about 50 nm. In some embodiments, a surface roughness may be from about 10 to about 100 nm. In some embodiments, a surface roughness may be from about 10 to about 500 nm.

Figure 2A:
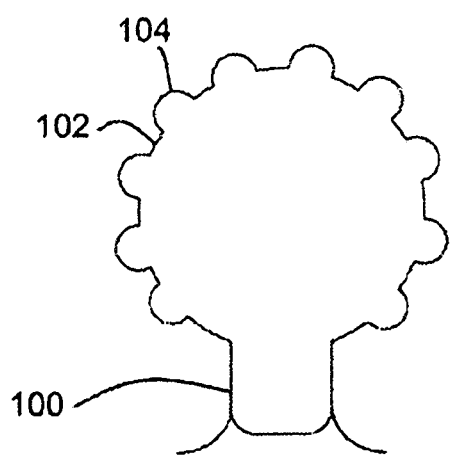
FIGS. 2A-B show schematic cross sectional views of electrode structures for use with an embodiment of the invention.
Figure 2B:
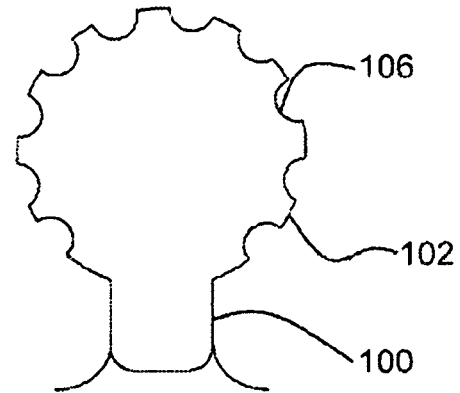
Figure 3A:
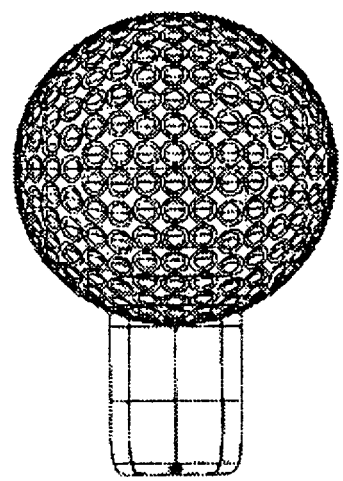
FIGS. 3A-B show schematic views of electrode structures for use with an embodiment of the invention.
Figure 3B:
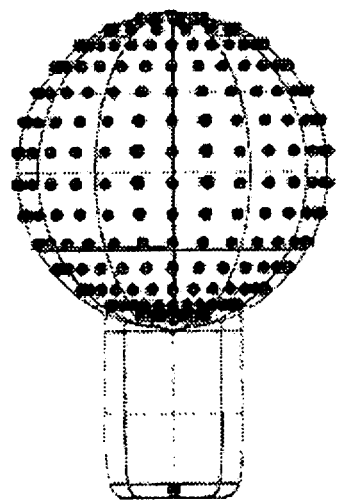

FIGS. 2A and 2B show schematic cross sectional views of suitable electrode structures for use with embodiments of the disclosed cell-based sensor devices. In FIG. 2A, the electrode structure has a generally spherical form, standing on columnar support 100. The sphere surface 102 has an array of rounded protrusions 104. In FIG. 2B, the electrode has a corresponding format, except that protrusions 104 are replaced by depressions 106. The effect of this is to provide additional surface area and surface features for interaction with cells, which may facilitate detection of electrical signals. FIGS. 3A and 3B correspond to FIGS. 2A and 2B, showing front views of suitable electrode structures with depressions or protrusions, respectively.

In some embodiments, the electrodes of the microelectrode array (or plurality of electrodes associated with the plurality of chambers containing cells with the device) may be used to stimulate cells as well as record electrical signals generated by the cells in response to ligand binding. For example, in some embodiments, one or more electrodes in each chamber may be used to trigger action potentials in neurons in order to calibrate the electrical signals recorded by the measurement electrodes and/or normalize the electrical signal levels recorded for different chambers or for chambers comprising neurons expressing different levels and/or different types of cell surface receptors. In some embodiments, one or more electrodes in each chamber may be used to stimulate the cells to assay the health of the cells, to measure an increase in the impedance of the cell-electrode interface, or to establish a baseline reading for that particular electrode to determine what a spike train signal for stimulated cells might look like in a detection event (i.e., to establish how many cells are in close proximity or contact with the electrode, what the electrical signal waveforms from these cells look like, to prepare for bursting behavior, etc).

In some embodiment, the cell-based sensor device may be "tuned" to improve the detection sensitivity for a specific compound or mixture of compounds, e.g., by controlling the types of receptors on the array and/or their position within the array of chambers. The type of neuron chosen for use in expressing a given receptor, e.g., an odorant receptor, may be selected on the basis of different background receptor expression levels and/or different background electrical signals (e.g., firing frequencies).

In some embodiments, the detection sensitivity of the disclosed cell-based sensor devices, or of the sensor panels and detection systems comprising said devices, may be adjusted by any of a variety of techniques known to those of skill in the art. Examples include, but are not limited to: (i) addition of one or more "odorant binding proteins" (e.g., soluble proteins that specific odorant molecules and improve their solubility and/or facilitate interaction with an odorant receptor) to the liquid medium bathing the cells in the device, (ii) addition of one or more compound stabilization additives (e.g., colloidal zinc) that stabilize the solubility of volatile organic compounds in solution to the liquid medium bathing the cells, (iii) by genetically engineering one or more of the receptors expressed by the cells within the device to enhance binding affinity and/or the electrical response of the cell, (iv) by overexpressing or underexpressing the receptors in one or more of the cell types within the device, (v) by genetically engineering one or more components of the intracellular signaling pathway to tune the sensitivity and electrical response of the cells within the device, (vi) by addition or genetic engineering of one or more synthetic signaling components to enhance the sensitivity and electrical response of the cells within the device, or (vii) by genetically deleting one or more naturally-occurring signaling components within the cells.

In some embodiments, the cell-based sensor device may comprise a processor for processing the patterns of electrical signals (or fingerprints) detected by the plurality of electrodes within the device. In some embodiments, the processor may be external to the cell-based sensor device. In some embodiments, machine learning-based processing of the patterns of electrical signals may be used to improve the sensitivity and/or specificity of the cell-based sensor device for detection of specific compounds or mixtures of compounds, e.g., using a machine learning algorithm that has been trained using training data sets comprising paired sets of the patterns of electrical signals (or "fingerprints") measured in response to exposure of the cell-based sensor device to specific compounds or mixtures of compounds at known concentrations. In some embodiments, the machine learning-based analysis may allow correcting for systematic bias in the detection sensitivity for different compounds arising from, e.g., differences in the solubility of different compounds in the medium bathing the cells, variations in the numbers of cell surface receptors expressed in different cell types, etc. Examples of suitable machine learning-based algorithms and training data sets will be described in more detail below.

The cell-based sensor devices and sensor panels of the present disclosure may be fabricated using any of a variety of techniques and materials known to those of skill in the art. In general, the sensor devices or sensor panels, or components thereof, may be fabricated either as monolithic parts or as an assembly of two or more separate parts that are subsequently mechanically clamped, fastened, or permanently bonded together. Examples of suitable fabrication techniques include, but are not limited to, conventional machining, CNC machining, injection molding, 3D printing, alignment and lamination of one or more layers of laser or die-cut polymer films, or any of a number of microfabrication techniques such as photolithography and wet chemical etching, dry etching, deep reactive ion etching, or laser micromachining, or any combination of these techniques. Once the sensor device or sensor panel part(s) have been fabricated, they may be fastened together using any of a variety of fasteners, e.g., screws, clips, pins, brackets, and the like, or may be bonded together using any of a variety of techniques known to those of skill in the art (depending on the choice of materials used), for example, through the use of anodic bonding, thermal bonding, ultrasonic welding, or any of a variety of adhesives or adhesive films, including epoxy-based, acrylic-based, silicone-based, UV curable, polyurethane-based, or cyanoacrylate-based adhesives.

The cell-based sensor devices and sensor panels of the present disclosure may be fabricated using a variety of materials known to those of skill in the art. Examples of suitable materials include, but are not limited to, silicon, fused-silica, glass, any of a variety of polymers, e.g., polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, metals (e.g., aluminum, stainless steel, copper, nickel, chromium, and titanium), or any combination of these materials.

In some embodiments, the cell-based sensor devices of the present disclosure, or one or more individual chambers of the plurality of chambers contained therein, may further comprise one or more additional components for use in regulating the microenvironment of the cells within the sensor device and maintaining cell viability. Examples include, but are not limited to, heating elements, cooling elements, temperature sensors, pH sensors, gas sensors (e.g., $O_2$ sensors, $CO_2$ sensors), glucose sensors, optical sensors, electrochemical sensors, opto-electric sensors, piezoelectric sensors, magnetic stirring/mixing components (e.g., micro stir bars or magnetic beads that are driven by an external magnetic field), etc., or any combination thereof. In some embodiments, the cell-based sensors of the present disclosure may further comprise additional components or features, e.g., transparent optical windows, microlens components, or light-guiding features to facilitate microscopic observation or spectroscopic monitoring techniques, inlet and outlet ports for making connections to perfusion systems, electrical connections for connecting electrodes or sensors to external processors or power supplies, etc. In some embodiments, the cell-based sensors of the present disclosure may further comprise a grid of LEDs positioned underneath the cells, e.g., neurons, within the plurality of chambers which may be used to stimulate the neurons optogenetically to assay cell health in situations where the health or response accuracy of the cells may be suspect. In some embodiments, the disclosed sensor devices may further comprise a controller (separately or in addition to the processor discussed above) configured to control heating and/or cooling elements, and/or to send instructions to and/or read data from one or more sensors.

In some embodiments, the disclosed cell-based sensor devices, or sensor panels comprising grids of cell-based sensor devices, may detect a presence or an absence of a compound in a liquid sample at a concentration detection limit ranging from about 10 millimolar (mM) to about 1 picomolar (pM), or less. In some embodiments, the concentration detection limit may be better than 10 mM, better than 5 mM, better than 1 mM, better than 100 micromolar (uM), better than 50 uM, better than 10 uM, better than 5 uM, better than 1 uM, 100 nanomolar (nM), better than 50 nM, better than 10 nM, better than 5 nM, better than 1 nM, better than 100 pM, better than 50 pM, better than 10 pM, better than 5 pM, or better than 1 pM. In some embodiments, the concentration detection limit may be compound specific.

In some embodiments, the disclosed cell-based sensor devices, or sensor panels comprising grids of cell-based sensor devices, may detect a presence or a second of a compound in a gas or air sample with a detection limit ranging from 100 parts per million (ppm) to 0.1 parts per billion (ppb), or less. In some embodiments, the detection limit may be better than 100 ppm, better than 10 ppm, better than 1 ppm, better than 100 ppb, better than 10 ppb, better than 1 ppb, or better than 0.1 ppb. In some embodiments, the concentration detection limit may be compound specific.

Sensitivity may refer to a value calculated according to the formula TP/(TP+FN), where TP is the number of true positive measurements (e.g., correctly detecting a presence of a compound in an environment or sample) and FN is the number of false negative measurements (e.g., incorrectly detecting an absence of a compound in an environment or sample). In some embodiments, the disclosed cell-based sensor devices, or sensor panels comprising grids of cell-based sensor devices, may detect a presence or an absence of one or more compounds at a sensitivity of greater than about: 70%, 75%, 80%, 85%, 86%, 87%, 88%, 89%, 90%, 91%, 92%, 93%, 94%, 95%, 96%, 97%, 98%, 99%, or 99.5% for the one or more compounds. In some cases, increasing the number of unique odorant receptors within the microelectrode array sensor device may increase the sensitivity of detection for one or more compounds.

Specificity may refer to a value calculated according to the formula TN/(TN+FP), where TN is the number of true negative measurements (e.g., correctly detecting an absence of a compound in an environment or sample) and FP is the number of false positive measurements (e.g., incorrectly detecting a presence of a compound in an environment or sample). In some embodiments, the disclosed cell-based sensor devices, or sensor panels comprising grids of cell-based sensor devices, may detect a presence or an absence of one or more compounds at a specificity of greater than about: 70%, 75%, 80%, 85%, 86%, 87%, 88%, 89%, 90%, 91%, 92%, 93%, 94%, 95%, 96%, 97%, 98%, 99%, or 99.5% for the one or more compounds. In some cases, increasing the number of unique odorant receptors within the microelectrode array sensor device may increase the sensitivity of detection for one or more compounds.

Positive Predictive Value (PPV) may refer to a value calculated according to the formula TP/(TP+FP). A PPV value may be the proportion of samples with positive test results that correctly detect a presence or an absence of a compound. In some embodiments, the disclosed cell-based sensor devices, or sensor panels comprising grids of cell-based sensor devices, may detect a presence or an absence of one or more compounds at a PPV of greater than about: 70%, 75%, 80%, 85%, 86%, 87%, 88%, 89%, 90%, 91%, 92%, 93%, 94%, 95%, 96%, 97%, 98%, 99%, or 99.5% for the one or more compounds.

Negative Predictive Value (NPV) may refer to a value calculated according to the formula TN/(TN+FN). In some embodiments, the disclosed cell-based sensor devices, or sensor panels comprising grids of cell-based sensor devices, may detect a presence or an absence of one or more compounds at an NPV of greater than about: 70%, 75%, 80%, 85%, 86%, 87%, 88%, 89%, 90%, 91%%, 92%, 93%, 94%, 95%, 96%, 97%, 98%, 99%, or 99.5% for the one or more compounds.

In some embodiments, the disclosed cell-based sensor devices, or sensor panels comprising grids of cell-based sensor devices, may detect a presence or an absence of one or more compounds at an accuracy of greater than about: 70%, 75%, 80%, 85%, 86%, 87%, 88%, 89%, 90%, 91%, 92%, 93%, 94%, 95%, 96%, 97%, 98%, 99%, or 99.5% for the one or more compounds.

In some embodiments, the disclosed cell-based sensor devices, or sensor panels comprising grids of cell-based sensor devices, may detect a presence or an absence of one or more compounds at a confidence level of greater than about 70%, 75%, 80%, 85%, 86%, 87%, 88%, 89%, 90%, 91%, 92%, 93%, 94%, 95%, 96%, 97%, 98%, 99%, or 99.5% for the one or more compounds.

In some embodiments, the disclosed cell-based sensor devices, or sensor panels comprising grids of cell-based sensor devices, may detect a presence or an absence of one or more compounds at one or more of a sensitivity, a specificity, a PPV, an NPV, an accuracy, a confidence level, or any combination thereof at greater than about: 70%, 75%, 80%, 85%, 86%, 87%, 88%, 89%, 90%, 91%, 92%, 93%, 94%, 95%, 96%, 97%, 98%, 99%, or 99.5% for the one or more compounds.

Sensor panels: Also disclosed herein are sensor panels comprising two or more individual cell-based sensor devices, wherein each cell-based sensor device has been designed and/or optimized (e.g., by virtue of choosing the types of cells and/or cell surface receptors expressed in each of the plurality of chambers within each cell-based sensor device) to detect a different compound or mixture of compounds, such that the sensor panel is designed and/or optimized to detect two or more different compounds or mixtures of compounds.

In some embodiments, a sensor panel may comprise a single cell-based sensor device, e.g., when deployed as part of a detection system comprising two or more sensor panels positioned at different locations, as will be described in more detail below.

Figure 4A:
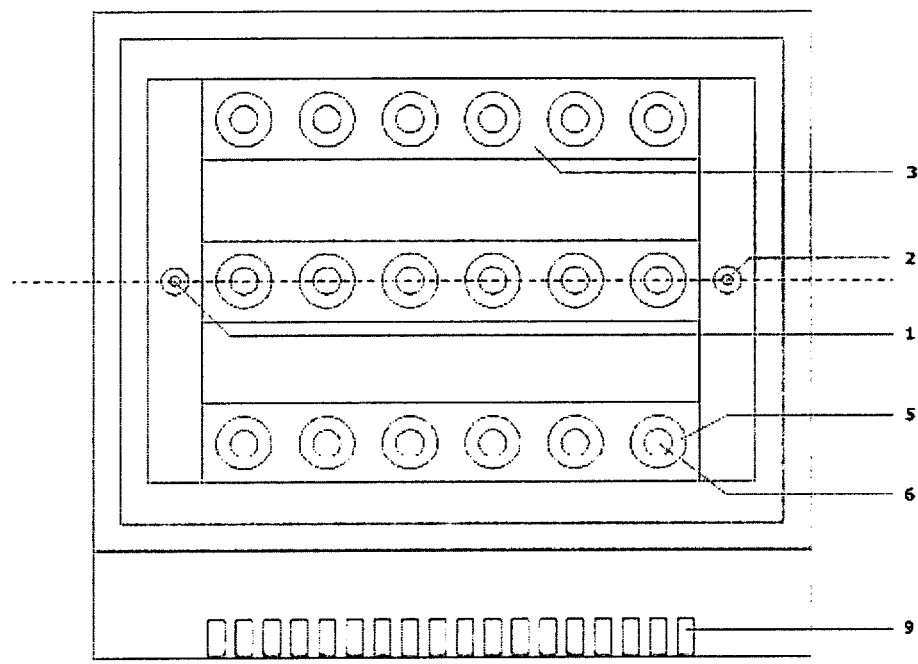
FIG. 4A-B show a non-limiting example of a cell-based sensor device of the present disclosure.
Figure 4B:
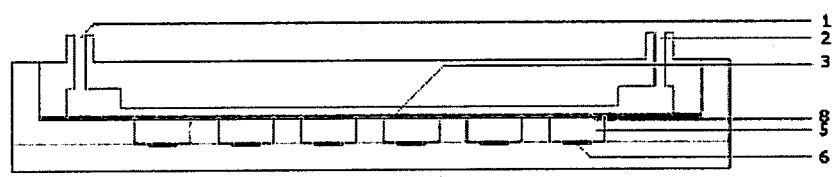

FIGS. 4A-B provide schematic illustrations (top and side views, respectively) of one non-limiting example of a cell-based sensor device of the present disclosure comprising a 3×6 grid of individual chambers or microwells within which one or more cells are compartmentalized. Cell culture medium enters the device through medium inlet 1, is delivered to cells in the microwells 5 via microfluidic channels 3, and exits the device via medium outlet 2. Each microwell 5 comprises an active electrode region 6, e.g., one or more electrodes that collectively constitute the microelectrode array component of the individual cell-based sensor device, as illustrated in FIG. 1. The device may comprise an anti-shear stress membrane 8, as well as a contact for complementary electronics 9. In some embodiments, a plurality of these cell-based sensor devices may be used to fabricate a sensor panel of the present disclosure, wherein the sensor panel comprises an array or grid of cell-based sensor devices. In some embodiments, the individual cell-based sensor devices within a sensor panel may all be in fluid communication with each other. In some embodiments, only a subset of the individual cell-based sensor devices within a sensor panel may be in fluid communication with each other. In some embodiments, none of the individual cell-based sensor devices within a sensor panel may be in fluid communication with each other.

In some embodiments, a sensor panel may comprise two individual cell-based sensor devices. In some embodiments, a sensor panel may comprise any number of individual cell-based sensor devices in the range from about 2 to about 100. In some embodiments, the number of cell-based sensor devices in the sensor panel may be at least 2, at least 5, at least 10, at least 20, at least 30, at least 40, at least 50, at least 60, at least 70, at least 80, at least 90, or at least 100. In some embodiments, the number of cell-based sensor devices in the sensor panel may be at most 100, at most 90, at most 80, at most 70, at most 60, at most 50, at most 40, at most 30, at most 20, at most 10, at most 5, or at most 2. Any of the lower and upper values described in this paragraph may be combined to form a range included within the present disclosure, for example, the number of cell-based sensor devices in the sensor panel may range from about 5 to about 20. Those of skill in the art will recognize that number of cell-based sensor devices in the sensor panel may have any value within this range, e.g., 25.

In some embodiments, the individual cell-based sensor devices may be randomly distributed across a substantially planar substrate or support component that defines the architecture of the sensor panel. In some embodiments, the individual cell-based sensor devices may be regularly arrayed across a substantially planar substrate or support component. In some embodiments, the individual cell-based sensor device may be arrayed in circular, spiral, triangular, rectangular, or square array patterns (or any other regular geometric pattern). For example, the individual cell-based sensor devices may be arrayed as a 2×2 array, a 3×3 array, a 4×4 array, a 5×5 array, a 6×6 array, a 7×7 array, an 8×8 array, a 9×9 array, or a 10×10 array, etc. In some embodiments, the individual cell-based sensor devices may be positioned on a non-planar, three-dimensional support structure, e.g., on the faces of a cubical, rectangular cuboid, or spherical structure, or on the face(s) of any other regular or free-form three-dimensional structure.

In some embodiments, each individual cell-based sensor device may comprise a processor for processing the patterns of electrical signals detected by plurality of electrodes in each device. In some embodiments, the sensor panel may comprise a processor for processing the patterns of electrical signals detected by the plurality of electrodes in all cell-based sensor devices of the panel. In many embodiments, the processor for each individual cell-based sensor device or for the sensor panel may also provide a time-stamp for the electrical signal data collected by each cell-based sensor device in the panel. As noted above for the cell-based sensor devices, in some embodiments, machine learning-based processing of the patterns of electrical signals recorded by the plurality of electrodes in each of the cell-based sensor devices of the panel may be used to improve the sensitivity and/or specificity of the sensor panel for detection of specific compounds or mixtures of compounds, while correcting for systematic detection biases due, e.g., to differences in compound solubility in the cell culture medium, and minimizing signal cross-talk between the individual cell-based sensor devices. Examples of suitable machine learning-based algorithms and training data sets will be described in more detail below.

As with the individual cell-based sensor devices described above, in some embodiments the sensor panels may further comprise one or more additional components for use in regulating the microenvironment of the cells within the sensor device and maintaining cell viability. Examples include, but are not limited to, heating elements, cooling elements, temperature sensors, pH sensors, gas sensors (e.g., $O_2$ sensors, $CO_2$ sensors), glucose sensors, optical sensors, electrochemical sensors, opto-electric sensors, piezoelectric sensors, magnetic stirring/mixing components (e.g., micro stir bars or magnetic beads that are driven by an external magnetic field), etc., or any combination thereof. In some embodiments, the sensor panels of the present disclosure may further comprise additional components or features, e.g., transparent optical windows, microlens components, or light-guiding features to facilitate microscopic observation or spectroscopic monitoring techniques, inlet and outlet ports for making connections to perfusion systems, electrical connections for connecting electrodes or sensors to external processors or power supplies, etc. In some embodiments, the disclosed sensor panels may further comprise a controller (separately or in addition to the processors discussed above) configured to control heating and/or cooling elements, and/or to send instructions to and/or read data from one or more sensors.

Air sampling devices: In some embodiments, the devices, systems and methods disclosed herein may comprise air sampling devices, or the use thereof, for facilitating transport of compounds, e.g., volatile compounds, from air into one or more cell-based sensor devices, e.g, into the one or more cell-based sensor devices of a sensor panel array that constitutes a detection system of the present disclosure. In general, these air sampling devices may employ any of a variety of strategies for enhancing transport of compounds from air into the cell-based sensor device, as will be discussed in more detail below.

Strategy A—increasing the surface area of the liquid/gas interface: One approach to facilitating the transfer of volatile compounds from a gas, e.g., air, to a liquid, e.g., the cell culture medium bathing the cell in the cell-based sensor devices of the present disclosure, is to design air sampling and/or sensor devices that provide a liquid/gas interface having a large surface area across which diffusion may take place. Examples of suitable approaches include, but are not limited to, the use of semipermeable membrane-based devices, gas perfusion chambers, atomization, or any combination thereof.

Devices comprising a semi-permeable gas exchange membrane: In some embodiments, cell culture medium may be perfused through an air-sampling device, e.g., a structure or panel, having a high surface area-to-volume ratio that is integrated with or positioned upstream of the cell-based sensor device or sensor panel. In some embodiments, the air-sampling device may consist of a series of microchannels that collectively present a large surface area for diffusion, where the liquid/gas interface is mediated by a semi-permeable gas exchange membrane (e.g., a PTFE membrane that has been engineered to be permeable to the volatile compound of interest but impermeable to the culture medium) that constitutes one boundary wall of the series of microchannels, thereby allowing for the exchange of volatile compounds between the air and the perfused medium. In some embodiments, the semi-permeable gas exchange membrane may comprise a hydrophobic or hydrophilic PTFE membrane of thickness ranging between about 10 micrometers to about 100 micrometers. In some embodiments, the thickness of the hydrophobic or hydrophilic PTFE membrane may be at least 10, at least 20, at least 30, at least 40, at least 50, at least 60, at least 70, at least 80, at least 90, or at least 100 micrometers. In some embodiments, the thickness of the hydrophobic or hydrophilic PTFE membrane may be at most 100, at most 90, at most 80, at most 70, at most 60, at most 50, at most 40, at most 30, at most 20, or at most 10 micrometers. Any of the lower and upper values described in this paragraph may be combined to form a range included within the present disclosure, for example, the thickness of the hydrophobic or hydrophilic PTFE membrane may range from about 20 to about 80 micrometers. Those of skill in the art will recognize that the thickness of the hydrophobic or hydrophilic PTFE membrane may have any value within this range, e.g., about 95 micrometers.

Figures 5A, 5B:
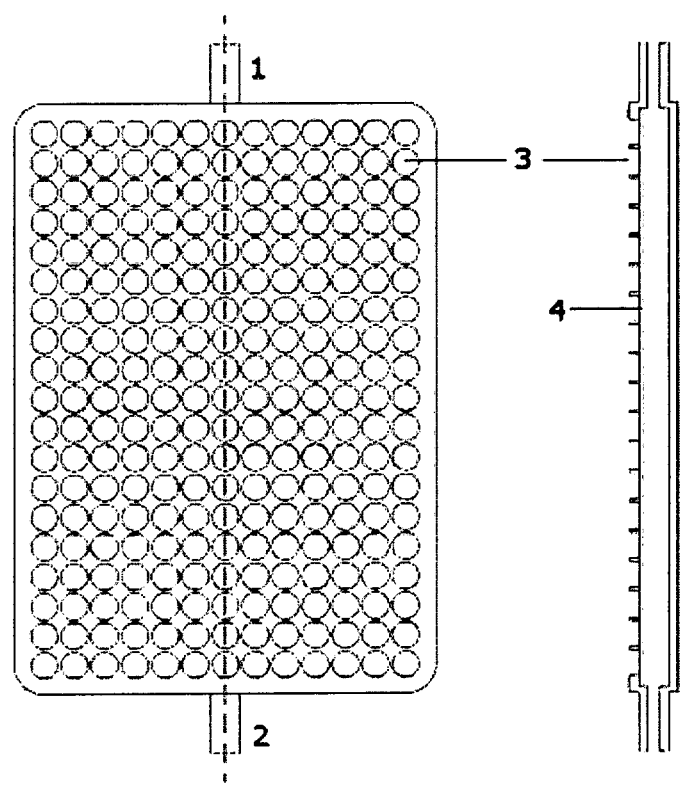
FIGS. 5A-B show a non-limiting example of an air-sampling device comprising microfluidic channels and a semi-permeable gas exchange membrane.

FIGS. 5A-B provide non-limiting schematic illustrations (top and side views, respectively) of an air-sampling device comprising a semi-permeable gas exchange membrane. Cell culture medium flows into the device via liquid inlet 1 and exits via liquid outlet 2. Openings 3 in a surface of the device allow gas or air samples to access the semi-permeable gas exchange membrane 4 and collectively provide for a large surface area in which volatile compounds may diffuse across the membrane and dissolve in the medium. The compound-containing culture medium is then transferred to a cell-based sensor device or sensor panel positioned downstream, e.g., by means of a microfluidics-based perfusion system.

Figure 6A:
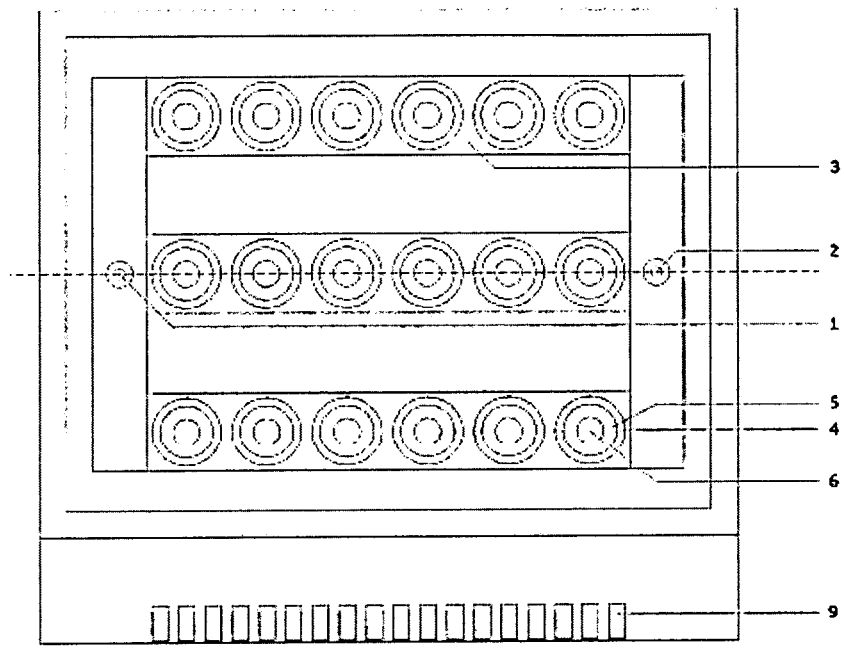
FIGS. 6A-B show a non-limiting example of a cell-based sensor device comprising an integrated gas exchange membrane.
Figure 6B:
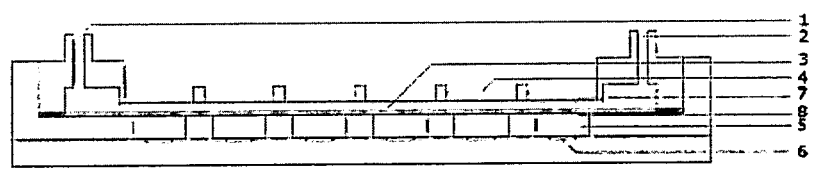

FIGS. 6A-B provide non-limiting schematic illustrations of a cell-based sensor device comprising an integrated semi-permeable gas exchange membrane. FIG. 6A provides a top view of the device. FIG. 6B provides is a side view of the device. In this example, the cell culture medium enters the device via liquid inlet 1, is delivered to the cells in microwells 5 via microfluidic channels 3, and exits via liquid outlet 2. Gas exchange occurs within openings 4 centered on the microwells 5 across semi-permeable membrane 7. The active electrode region is indicated as 6. The device also comprises an anti-shear stress membrane 8, and a contact for complementary electronics 9. In some embodiments, the layer of culture medium positioned between the cells (e.g., neurons) and the surface of the semi-permeable membrane may be no deeper than about 10 microns, about 20 microns, about 30 microns, about 40 microns, about 50 microns, about 100 microns, about 200 microns, about 300 microns, about 400 microns, or about 500 microns to minimize the path length that the volatile compound may need to traverse to reach the requisite receptors, e.g., odorant receptors, while still providing the cell layer with enough nutrients for long-term survival. New medium may be constantly perfused at a slow rate into the sensor device to introduce fresh nutrients and proteins, while old medium flows out to remove waste products, such as carbon dioxide, as well as dissolved compounds or particulates from previous exposures to a gas or air sample. In some embodiments, a plurality of such cell-based sensor devices may be arrayed to form a sensor panel. In some embodiments, by keeping all of the microelectrode array-based sensor devices on one panel in the same medium bath, the stability of the system may be increased and the ability of the medium to buffer any potentially deleterious changes in pH, dissolved oxygen concentration, and temperature may be improved.

In some embodiments, e.g., those in which a semipermeable gas exchange membrane is incorporated into an air sampling device or integrated directly with a cell-based sensor device or sensor panel, the surface area-to-volume ratio for the semi-permeable membrane and the volume of liquid medium in contact with the semi-permeable membrane at a given instant may be greater than $1\ cm^{-1}$, $10\ cm^{-1}$, $100\ cm^{-1}$, or $1{,}000\ cm^{-1}$. The use of higher surface area-to-volume ratios in the device may facilitate efficient gas exchange and dissolution of volatile compounds into the cell culture medium.

Devices comprising a gas perfusion chamber: In some embodiments, the gas or air containing the volatile compounds of interest may be injected into cell culture medium contained using a micro bubbler within a small mixing chamber that is part of an air-sampling device positioned upstream of the cell-based sensor device or sensor panel. In some embodiments, a gas perfusion chamber and microbubbler may be directly integrated with a cell-based sensor device or sensor panel of the present disclosure.

Figure 7:
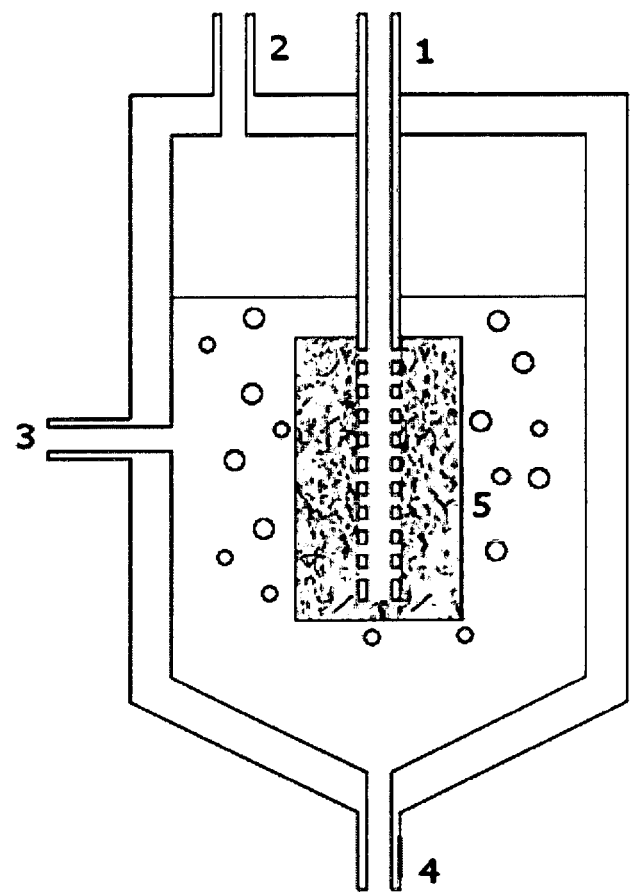
FIG. 7 shows an non-limiting example of an air sampling device comprising a gas perfusion chamber with a micro bubbler.

FIG. 7 provides a non-limiting schematic illustration of an air-sampling device comprising a perfusion chamber. The gas or air sample enters the device at gas inlet 1 and is forced to permeate through porous matrix 5 of the micro bubbler positioned in a small volume of cell culture medium entering the device via liquid inlet 3, thereby generating very fine bubbles that collectively comprise a large aggregate gas/liquid interfacial surface area and promote diffusive transfer of volatile compounds within the gas or air sample into the cell culture medium. The gas or air sample exits the device via gas outlet 2, and the loaded culture medium exits the device via liquid outlet 4 to be delivered, after appropriate degassing, to a cell-based sensor device or sensor panel located downstream from the perfusion chamber.

Devices comprising an atomizer: In some embodiments, the gas or air containing the volatile compounds of interest may be injected into a small mixing chamber within the air-sampling device where it is atomized using ultrasonic frequencies in a technique commonly used in cool gas stream humidification. The resultant vapor may then be recondensed and injected into the culture medium that flows into the cell-based sensor device or sensor panel. In some embodiments, the mixing chamber and atomizer may be directly integrated with a cell-based sensor device or sensor panel of the present disclosure.

Figure 8:
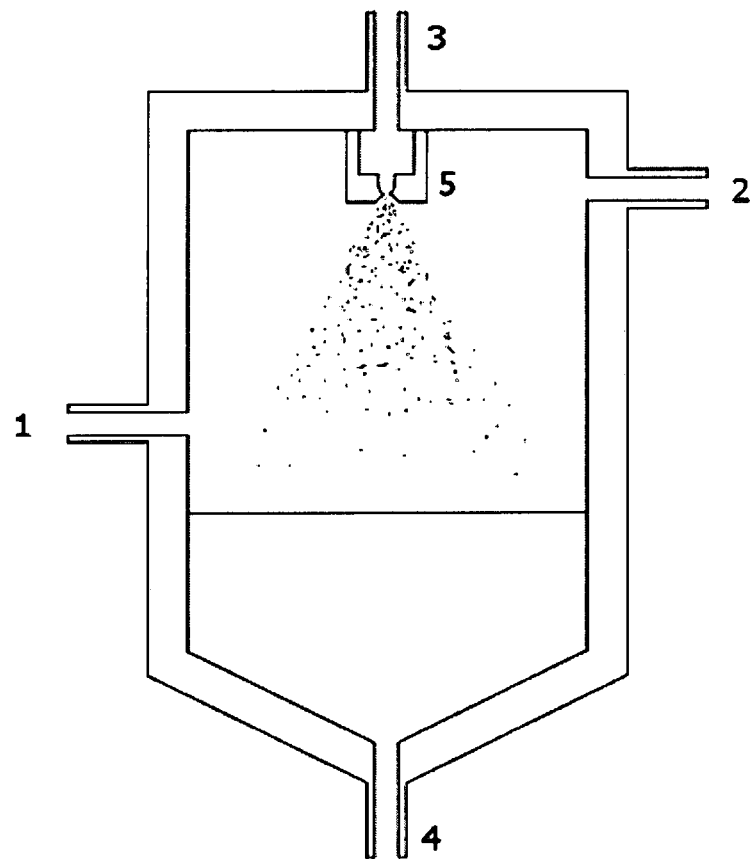
FIG. 8 shows a non-limiting example of an air sampling device comprising an atomizer.

FIG. 8 provides a non-limiting schematic illustration of an air-sampling device comprising an atomizer. A gas or air sample comprising volatile compounds of interest enters the device via gas inlet 1 and exits via gas outlet 2. Culture medium enters the device via liquid inlet 3, and is forced through spray nozzle 5 that vibrates at ultrasonic frequencies to create a fine mist or vapor. The gas or air sample mixes with the vapor, which collectively comprises a large aggregate gas/liquid interfacial surface area and promotes diffusive transfer of volatile compounds within the gas or air sample into the vapor, following which the vapor is then condensed and the compound-loaded medium then exits the device via liquid outlet 4.

Strategy B—increasing the solubility of volatile compounds: Another example of an approach to facilitate the transfer of volatile compounds from a gas, e.g., air, to a liquid, e.g., the cell culture medium bathing the cell in the cell-based sensor devices of the present disclosure, is to utilize methods for increasing the solubility of the compounds in the cell culture medium. Examples of suitable approaches include, but are not limited to, the use of a pressurized gas phase, heating the liquid phase, increasing the air velocity or pressure over the surface of a gas exchange membrane (e.g., by the inclusion of a fan), or any combination thereof.

Devices comprising a pressurized gas phase: In some embodiments, the gas or air sample may be compressed and placed in contact with the cell culture medium within a closed mixing chamber that is part of an air-sampling device positioned upstream of a cell-based sensor device or sensor panel. Pressurization of the gas or air sample serves to increase the partial pressure of volatile compounds, thereby increasing the solubility of the volatile compounds in the cell culture solution according to Henry's law. The mixture may then be depressurized and delivered to the cell-based sensor device or sensor panel.

Devices comprising a heated liquid phase: In some embodiments, the cell culture medium in which the volatile compounds are to be solubilized can be heated within an air-sampling device to increase the solubility of the compounds. The cell culture medium may then be cooled again to the specified temperature (e.g., 37 degrees C.) before reintroduction to a cell-based sensor device or sensor panel.

Devices comprising a dedicated solvent: In some embodiments, the volatile compounds may be dissolved in a liquid phase solvent that is different from the cell culture medium. For example, many organic volatiles may be far more soluble in polar, aprotic solvents like DMSO or acetone than in typical aqueous solutions used in cell culture. Gas or air samples comprising the volatile compounds of interest may be mixed with a solvent within an air-sampling device positioned upstream of a cell-based sensor device or sensor panel. In some embodiments, the loaded solvent may then be neutralized with another solution to create a nontoxic, biocompatible suspension prior to re-introduction into the stream of culture medium entering the cell-based sensor device or sensor panel.

In some embodiments, air-sampling devices of the present disclosure may utilize any combination of the strategies and approaches outline above to create a number of different final system configurations.

Detection systems: Also disclosed herein are detection systems which comprise two or more of the cell-based sensor panels described above, where the detection systems provide a means for monitoring the air in a given space (e.g., an outdoor environment or an indoor/enclosed environment) for the presence of volatile compounds, e.g., volatile markers or taggants of explosive materials. In most embodiments, the two or more sensor panels of the detection system may be positioned at known locations within or around the environment to be monitored, and time-stamped data for the patterns of electrical signals recorded by each of the sensor devices in each sensor panel may be used, along with the known locations of the sensor devices/panels from which they arose, to both detect the presence of, and identify, a compound of mixture of compounds of interest, but also to locate the position of the source of the compound or mixture of compounds within the space.

In some embodiments, the detection systems of the present disclosure may comprise between 2 and about 200 panels, or more. In some embodiments, the detection system may comprise at least 2 sensor panels, at least 4 sensor panels, at least 6 sensor panels, at least 8 sensor panels, at least 10 sensor panels, at least 15 sensor panels, at least 20 sensor panels, at least 40 sensor panels, at least 60 sensor panels, at least 80 sensor panels, at least 100 sensor panels, or at least 200 sensor panels. In some embodiments, the detection system may comprise at most 200 sensor panels, at most 100 sensor panels, at most 80 sensor panels, at most 60 sensor panels, at most 40 sensor panels, at most 20 sensor panels, at most 15 sensor panels, at most 10 sensor panels, at most 8 sensor panels, at most 6 sensor panels, at most 4 sensor panels, or at most 2 sensor panels. Any of the lower and upper values described in this paragraph may be combined to form a range included within the present disclosure, for example, the number of sensor panels in the detection system may range from about 4 to about 80. Those of skill in the art will recognize that the number of sensor panels in the detection system may have any value within this range, e.g., 152.

In some embodiments, the two or more sensor panels may comprise the same complement of cell-based sensor devices, i.e., a set of cell-based sensor devices designed and/or optimized for detection of the same set of compounds or mixtures of compounds. In some embodiments, the two or more sensor panels may comprise different complements of cell-based sensor devices, i.e., sets of cell-based sensor devices designed and/or optimized for detection of a different set of compounds or mixtures of compounds.

In some embodiments, the detection system may further comprise two or more air sampling devices as described above, wherein each air sampling device is in fluid communication with one of the two or more sensor panels, and wherein each air sampling device is configured to facilitate the transfer compounds present in the air to the culture medium that bathes the cells in each of the chambers in each cell-based sensor device of the corresponding sensor panel.

In some embodiments, a detection system of the present disclosure may comprise a single air sampling device, two air sampling devices, three air sampling device, four air sampling devices, five air sampling devices, or more. In some embodiments, a detection system of the present disclosure may comprise at least one air sampling device for each sensor panel of the system. In some embodiments, a detection system of the present disclosure may comprise two or more air sampling devices for each sensor panel of the system. In some embodiments, detection systems comprising two or more air sampling devices may comprise two or more of the same type of air sampling device, or two or more different types of air sampling devices. Any combination of different air sampling devices may be used in the detection systems of the present disclosure.

In some embodiments, the detection system may comprise a controller comprising one or more processors configured to receive the electrical signals measured by the plurality of electrodes in each cell-based sensor device of the two or more sensor panels. In some embodiments, the controller stores and processes a pattern of electrical signals associated with a compound or mixture of compounds that is generated by at least one of the cell-based sensor devices in each of the two or more sensor panels (which are positioned at known locations) to identify the compound or mixture of compounds and provide a spatial location of a source of the compound or mixture of compounds within an outdoor or indoor (enclosed) environment, as will be discussed in more detail below. In some embodiments, the controller may further provide control signals and data acquisition capabilities for controlling heating elements, cooling elements, cell culture medium perfusion systems, air collection systems (e.g., blowers, fans, etc.), humidity control systems, etc., as well as reading data provided by one or more sensors, e.g., temperature sensors, pH sensors, gas sensors (e.g., $O_2$ sensors, $CO_2$ sensors), glucose sensors, optical sensors, electrochemical sensors, opto-electric sensors, piezoelectric sensors, etc.

In some embodiments, the detection system may further comprise heating systems, cooling systems, cell culture medium perfusion systems, gas perfusion systems, air collection systems (e.g., blowers, fans, etc.), humidity control systems, motion dampening systems, one or more computers and computer memory storage devices, etc.

Triangulation of sensor signals to locate sources of volatile compounds: As noted above, one important feature of the disclosed detection systems is the ability to process time-stamped sensor data provided by two or more sensor panels positioned at known locations within or around the environment to be monitored, and both detect and identify a volatile compound or mixture of volatile compounds of interest as well as identify the location of the source of the volatile compound(s) within the space being monitored. In some embodiments, a detection system comprising two sensor panels positioned at known locations, e.g., along a linear corridor, may be used to detect volatile compound(s) and estimate the position of a stationary source of the compounds (e.g., by monitoring the time difference between detection by the first sensor panel and detection by the second panel), and/or to determine the direction of travel of a moving source (e.g. by monitoring signals over time). In some embodiments, a detection system comprising three or more sensor panels positioned at known locations, e.g., at multiple positions along a linear corridor, or at multiple positions around an enclosed environment such as an airport terminal space, to detect volatile compound(s) and make a more accurate determination of the location of the source of the compound(s) and/or the direction of travel of the source.

In some embodiments, this may require knowledge of the diffusion coefficients in air for the one or more volatile compounds to be detected. The difference between the time that a signal is detected by a first sensor panel and the time(s) it is detected by at least a second sensor panel may then be used, along with the known separation distance(s) for the sensor panels and the diffusion coefficient(s) for the compound(s) detected, to calculate the position of the source relative to the locations of the sensor panels. Furthermore, monitoring of the time-dependent signals arising from each sensor panel permits tracking of any motion of the source.

In some embodiments, the use of triangulation techniques to locate and monitor the position of a source of volatile compound(s) may also require knowledge of the detection sensitivities and response times of the cell-based sensor devices used to monitor the space. This information can then be used to correct estimates for distances between the position of the source and the locations of the sensor panels in order to make a more accurate determination of the position of the source.

In some embodiments, the accuracy of the detection systems for determining the position of the source may be further enhanced through the use of machine learning-based processing of the sensor signals. Machine learning algorithms that have been trained using sensor signal data sets generated using control samples of one or a mixture of known compound(s), samples comprising one or a mixture of known compound(s) at varying concentration levels, and wherein the control samples are positioned at known locations with the space being monitored while collecting the training sensor signal data, may then be used to map a given test sensor signal input data set to an output data set comprising a determination of compound identity, compound mixture identity, estimates of compound concentration(s), location of compound source(s) within the space, or any combination thereof. In some cases, a machine learning approach may also provide improved accuracy for determining a source location within the space where air movement is an issue (e.g., by training the machine learning algorithm under conditions where air movement is controlled but representative of the range of air movements typically observed within the space). Examples of suitable machine learning-based algorithms and training data sets will be described in more detail below.

In some embodiments, the disclosed detection systems may be used to detect and identify volatile compounds or mixtures of compounds in any of a variety of spaces or environments. Examples include, but are not limited to, residential spaces, office spaces, commercial spaces, manufacturing facilities, hospital facilities, airport facilities, and the like. In some embodiments, the disclosed detection systems may be used to detect and identify volatile compounds or mixtures of compounds in outdoor environments, e.g., enclosed courtyards and the like.

In some embodiments, the disclosed detection systems may provide a determination of the spatial location of a source of volatile compound(s) within a monitored space with an accuracy ranging from about 0.001 meters to about 10 meters in any dimension. In some embodiments, the location of the source may be determined to within at least 10 meters, at least 5 meters, at least 1.0 meters, at least 0.1 meters, at least 0.01 meters, or at least 0.001 meters in any dimension.

Machine learning-based sensor signal processing: Any of a variety of machine learning algorithms known to those of skill in the art may be suitable for use in processing the sensor signals generated by the disclosed cell-based sensor devices and systems. Examples include, but are not limited to, supervised learning algorithms, unsupervised learning algorithms, semi-supervised learning algorithms, reinforcement learning algorithms, deep learning algorithms, or any combination thereof. In one preferred embodiment, a support vector machine learning algorithm may be used. In another preferred embodiment, a deep learning machine learning algorithm may be used.

Supervised learning algorithms: In the context of the present disclosure, supervised learning algorithms are algorithms that rely on the use of a set of labeled, paired training data examples (e.g., sets of sensor signal patterns, and the corresponding known compound identities and concentrations for control samples) to infer the relationship between compound identity and sensor signal pattern.

Unsupervised learning algorithms: In the context of the present disclosure, unsupervised learning algorithms are algorithms used to draw inferences from training data sets consisting of sensor signal patterns that are not paired with labeled compound identity data. The most commonly used unsupervised learning algorithm is cluster analysis, which is often used for exploratory data analysis to find hidden patterns or groupings in process data.

Semi-supervised learning algorithms: In the context of the present disclosure, semi-supervised learning algorithms are algorithms that make use of both labeled and unlabeled data for training (typically using a relatively small amount of labeled data with a large amount of unlabeled data).

Reinforcement learning algorithms: In the context of the present disclosure, reinforcement learning algorithms are algorithms which are used, for example, to determine a set of sensor signal processing steps that should be taken so as to maximize a compound identification reward function. Reinforcement learning algorithms are commonly used for optimizing Markov decision processes (i.e., mathematical models used for studying a wide range of optimization problems where future behavior cannot be accurately predicted from past behavior alone, but rather also depends on random chance or probability). Q-learning is an example of a class of reinforcement learning algorithms. Reinforcement learning algorithms differ from supervised learning algorithms in that correct training data input/output pairs are never presented, nor are sub-optimal actions explicitly corrected. These algorithms tend to be implemented with a focus on real-time performance through finding a balance between exploration of possible outcomes (e.g. correct compound identification) based on updated input data and exploitation of past training.

Deep learning algorithms: In the context of the present disclosure, deep learning algorithms are algorithms inspired by the structure and function of the human brain called artificial neural networks (ANNs), and specifically large neural networks comprising multiple hidden layers, that are used to map an input data set (e.g. a sensor signal pattern) to, for example, a determination of compound identity. Artificial neural networks and deep learning algorithms will be discussed in more detail below.

Support vector machine learning algorithms: Support vector machines (SVMs) are supervised learning algorithms that analyze data used for classification and regression analysis. Given a set of training data examples (e.g., a sensor electrical signals), each marked as belonging to one or the other of two categories (e.g., compound detected or compound not detected), an SVM training algorithm builds a linear or non-linear classifier model that assigns new data examples to one category or the other.

Figure 9:
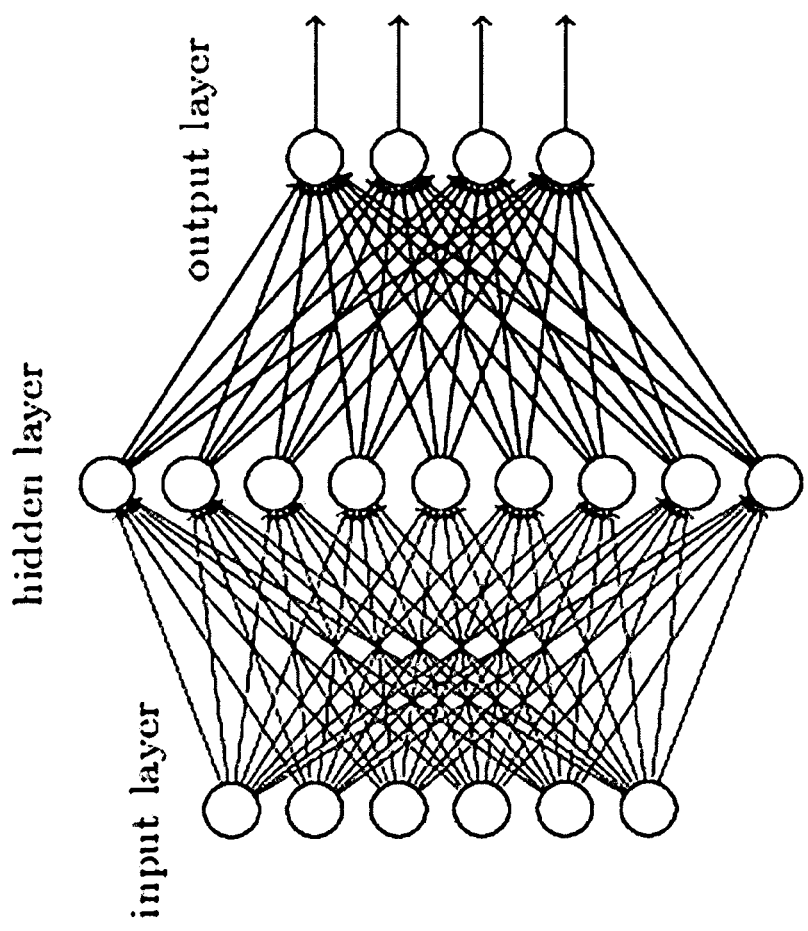
FIG. 9 shows a schematic illustration of an artificial neural network (ANN).
Figure 10:
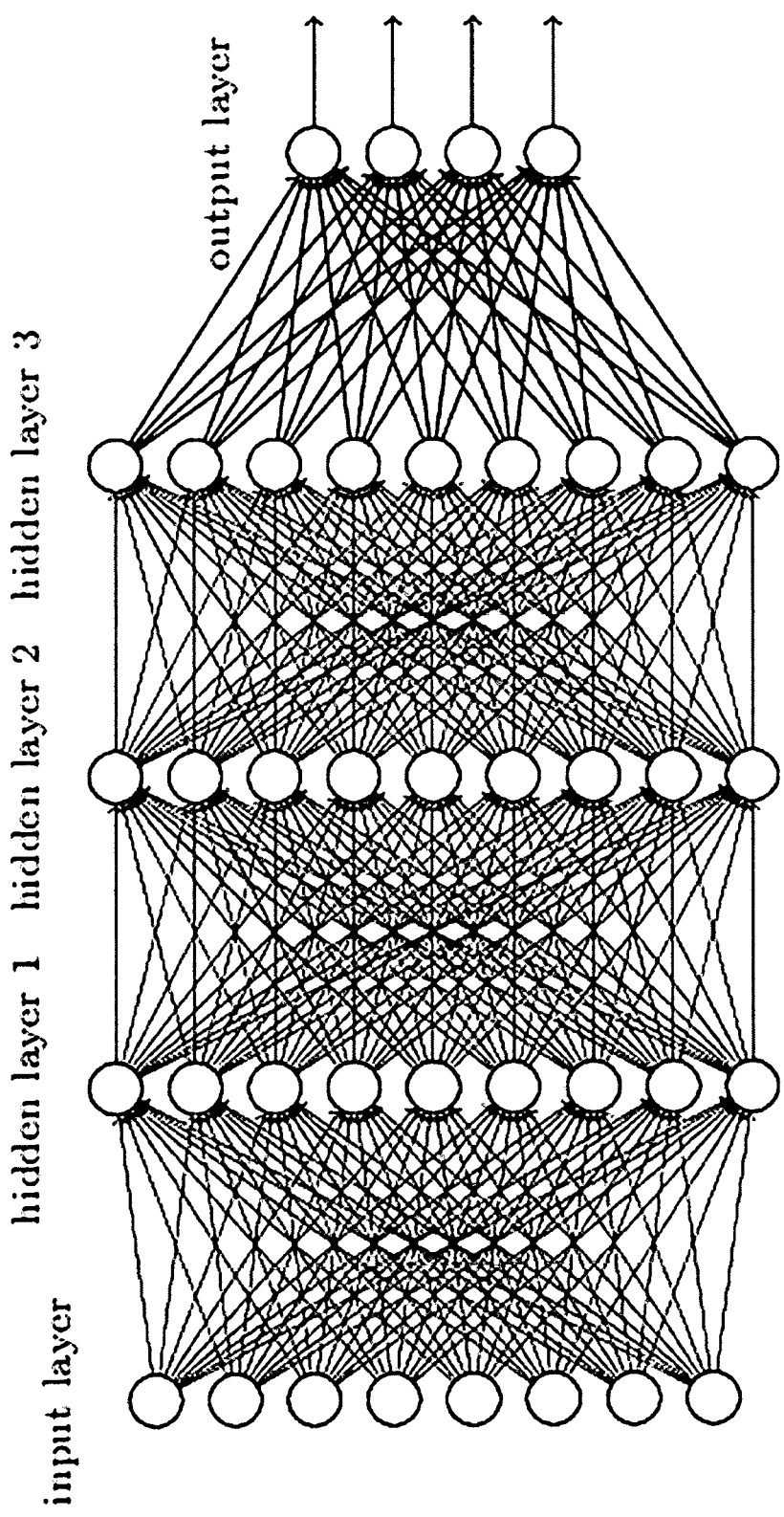
FIG. 10 shows a schematic illustration of a deep learning neural network (DNN).
Figure 11:
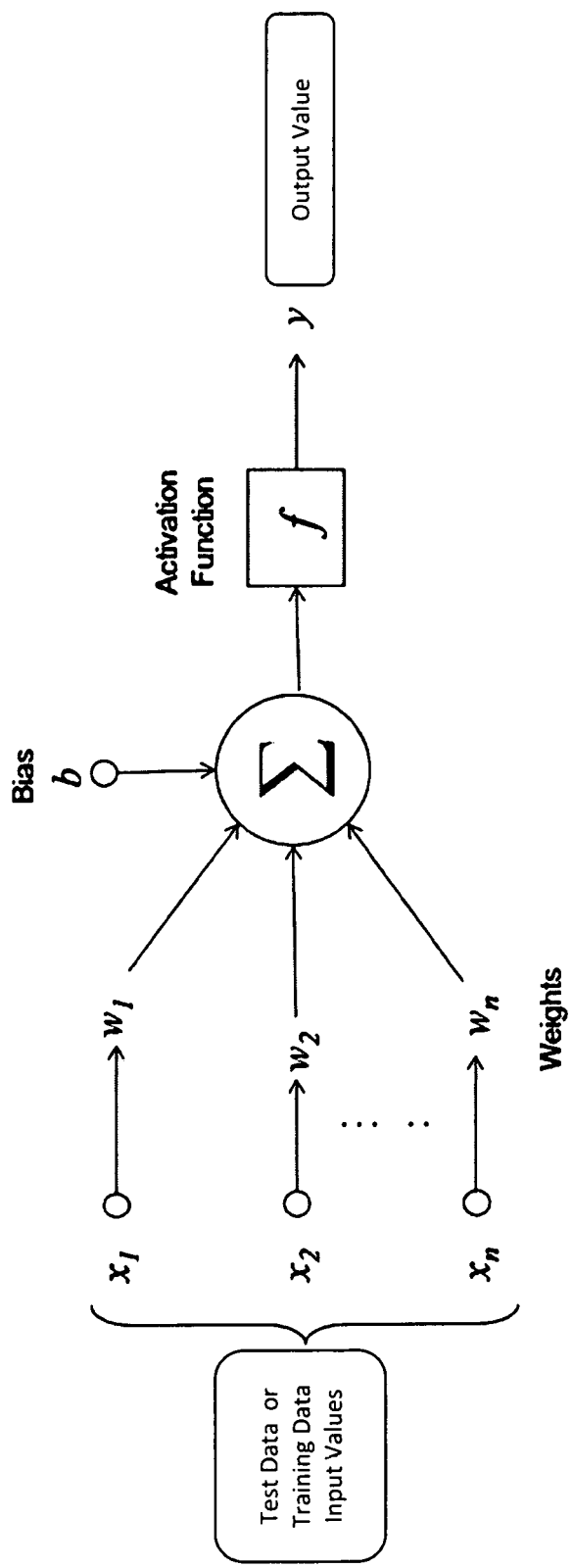
FIG. 11 provides a schematic illustration of the functionality of a node within a layer of an artificial neural network or deep learning neural network.

Artificial neural networks & deep learning algorithms: Artificial neural networks (ANN) are machine learning algorithms that may be trained to map an input data set (e.g., sensor signal patterns) to an output data set (e.g., compound identification, etc.), where the ANN comprises an interconnected group of nodes organized into multiple layers of nodes (FIG. 9). For example, the ANN architecture may comprise at least an input layer, one or more hidden layers, and an output layer. The ANN may comprise any total number of layers, and any number of hidden layers, where the hidden layers function as trainable feature extractors that allow mapping of a set of input data to an output value or set of output values. As used herein, a deep learning algorithm (DNN) is an ANN comprising a plurality of hidden layers, e.g., two or more hidden layers (FIG. 10). Each layer of the neural network comprises a number of nodes (or "neurons"). A node receives input that comes either directly from the input data (e.g., sensor signals or signal patterns) or the output of nodes in previous layers, and performs a specific operation, e.g., a summation operation. In some cases, a connection from an input to a node is associated with a weight (or weighting factor). In some cases, the node may sum up the products of all pairs of inputs, $x_i$, and their associated weights (FIG. 11). In some cases, the weighted sum is offset with a bias, b, as illustrated in FIG. 11. In some cases, the output of a node or neuron may be gated using a threshold or activation function, f, which may be a linear or non-linear function. The activation function may be, for example, a rectified linear unit (ReLU) activation function, a Leaky ReLu activation function, or other function such as a saturating hyperbolic tangent, identity, binary step, logistic, arcTan, softsign, parameteric rectified linear unit, exponential linear unit, softPlus, bent identity, softExponential, Sinusoid, Sinc, Gaussian, or sigmoid function, or any combination thereof.

The weighting factors, bias values, and threshold values, or other computational parameters of the neural network, may be "taught" or "learned" in a training phase using one or more sets of training data. For example, the parameters may be trained using the input data from a training data set and a gradient descent or backward propagation method so that the output value(s) (e.g., a determination of compound identity and/or the position coordinates of the source of the compound) that the ANN computes are consistent with the examples included in the training data set. The parameters may be obtained from a back propagation neural network training process that may or may not be performed using the same computer system hardware as that used for performing the cell-based sensor signal processing methods disclosed herein.

Any of a variety of neural networks known to those of skill in the art may be suitable for use in processing the sensor signals generated by the cell-based sensor devices and systems of the present disclosure. Examples include, but are not limited to, feedforward neural networks, radial basis function networks, recurrent neural networks, or convolutional neural networks, and the like. In some embodiments, the disclosed sensor signal processing methods may employ a pre-trained ANN or deep learning architecture. In some embodiments, the disclosed sensor signal processing methods may employ an ANN or deep learning architecture wherein the training data set is continuously updated with real-time detection system sensor data generated for control samples by a single local detection system, from a plurality of local detection systems, or from a plurality of geographically-distributed detection systems that are connected through the internet.

In general, the number of nodes used in the input layer of the ANN or DNN (which may enable input of data from multiple electrodes, cell-based sensor devices, or sensor panels) may range from about 10 to about 100,000 nodes. In some instances, the number of nodes used in the input layer may be at least 10, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000, at least 20,000, at least 30,000, at least 40,000, at least 50,000, at least 60,000, at least 70,000, at least 80,000, at least 90,000, or at least 100,000. In some instances, the number of node used in the input layer may be at most 100,000, at most 90,000, at most 80,000, at most 70,000, at most 60,000, at most 50,000, at most 40,000, at most 30,000, at most 20,000, at most 10,000, at most 9000, at most 8000, at most 7000, at most 6000, at most 5000, at most 4000, at most 3000, at most 2000, at most 1000, at most 900, at most 800, at most 700, at most 600, at most 500, at most 400, at most 300, at most 200, at most 100, at most 50, or at most 10. Those of skill in the art will recognize that the number of nodes used in the input layer may have any value within this range, for example, about 512 nodes.

In some instance, the total number of layers used in the ANN or DNN (including input and output layers) may range from about 3 to about 20. In some instance the total number of layer may be at least 3, at least 4, at least 5, at least 10, at least 15, or at least 20. In some instances, the total number of layers may be at most 20, at most 15, at most 10, at most 5, at most 4, or at most 3. Those of skill in the art will recognize that the total number of layers used in the ANN may have any value within this range, for example, 8 layers.

In some instances, the total number of learnable or trainable parameters, e.g., weighting factors, biases, or threshold values, used in the ANN or DNN may range from about 1 to about 10,000. In some instances, the total number of learnable parameters may be at least 1, at least 10, at least 100, at least 500, at least 1,000, at least 2,000, at least 3,000, at least 4,000, at least 5,000, at least 6,000, at least 7,000, at least 8,000, at least 9,000, or at least 10,000. Alternatively, the total number of learnable parameters may be any number less than 100, any number between 100 and 10,000, or a number greater than 10,000. In some instances, the total number of learnable parameters may be at most 10,000, at most 9,000, at most 8,000, at most 7,000, at most 6,000, at most 5,000, at most 4,000, at most 3,000, at most 2,000, at most 1,000, at most 500, at most 100 at most 10, or at most 1. Those of skill in the art will recognize that the total number of learnable parameters used may have any value within this range, for example, about 2,200 parameters.

ANN or DNN training data sets: The input data for training of the ANN or deep learning algorithm may comprise a variety of input values depending whether the machine learning algorithm is used for processing sensor signal data for a single cell-based sensor device, a sensor panel, or a detection system of the present disclosure. For processing sensor signals generated by individual cell-based sensor devices or sensor panels, the input data of the training data set may comprise single timepoint data or multi-timepoint (i.e., kinetic) data for the electrical signals (e.g., voltages or currents) recorded by one or more electrodes in one or more cell-based sensor devices, or in one or more sensor panels, along with the compound identities and concentrations of control samples to which the sensor devices or panels have been exposed. For processing sensor signals generated by the disclosed detection systems, the input data of the training data set may comprise single timepoint or kinetic data for the electrical signals recorded by one or more electrodes in one or more cell-based sensor devices of each panel, along with the time-stamp data associated with the electrical signal data, the position coordinates for the known locations of the sensor panels, and the compound identities, diffusion coefficients, concentrations, and position coordinates for the known locations of the control samples to which the sensor panels of the detection system have been exposed. In general, the ANN or deep learning algorithm may be trained using one or more training data sets comprising the same or different sets of input and paired output (e.g., compound identity and/or source location) data.

Distributed data processing systems and cloud-based training databases: In some embodiments, the machine learning-based methods for cell-based sensor signal processing disclosed herein may be used for processing sensor data on one or more computer systems that reside at a single physical/geographical location. In some embodiments, they may be deployed as part of a distributed system of computers that comprises two or more computer systems residing at two or more physical/geographical locations. Different computer systems, or components or modules thereof, may be physically located in different workspaces and/or worksites (i.e., in different physical/geographical locations), and may be linked via a local area network (LAN), an intranet, an extranet, or the internet so that training data and/or sensor data from, e.g., air samples, to be processed may be shared and exchanged between the sites.

In some embodiments, training data may reside in a cloud-based database that is accessible from local and/or remote computer systems on which the machine learning-based sensor signal processing algorithms are running. As used herein, the term "cloud-based" refers to shared or sharable storage of electronic data. The cloud-based database and associated software may be used for archiving electronic data, sharing electronic data, and analyzing electronic data. In some embodiments, training data generated locally may be uploaded to a cloud-based database, from which it may be accessed and used to train other machine learning-based detection systems at the same site or a different site. In some embodiments, sensor device and system test results generated locally may be uploaded to a cloud-based database and used to update the training data set in real time for continuous improvement of sensor device and detection system test performance.

Processors and computer systems: The present disclosure provides computer control systems that are programmed to implement methods of the disclosure. The computer system may be programmed or otherwise configured to direct electrodes to measure one or more electrical signals, to receive one or more electrical signals from one or more electrodes, to generate a pattern of electrical signals, to store patterns of electrical signals or electrical signals in a database, to compare a pattern of electrical signals to a pattern stored in a database, or any combination thereof. The computer system may regulate various aspects of data collection, data analysis, and data storage, of the present disclosure, such as, for example, directing electrical signal measurements, comparing of patterns based of electrical signals measured, generating patterns based on electrical signal data, any combinations thereof, and others. The computer system may be an electronic device of a user or a computer system that is remotely located with respect to the electronic device. The electronic device can be a mobile electronic device.

In some embodiments, the hardware and software code of the computer system may be built around a field-programmable gate array (FPGA) architecture. Unlike microprocessors, which process a fixed set of instructions using a corresponding hard-wired block of logic gates, an FPGA doesn't have any hard-wired logic blocks. Rather, the logic blocks are programmed by the user, which constitutes the "programming" of an FPGA (the code is essentially a hardware change). FPGAs have the advantage of being much faster than microprocessors for performing specific sets of instructions.

Figure 12:
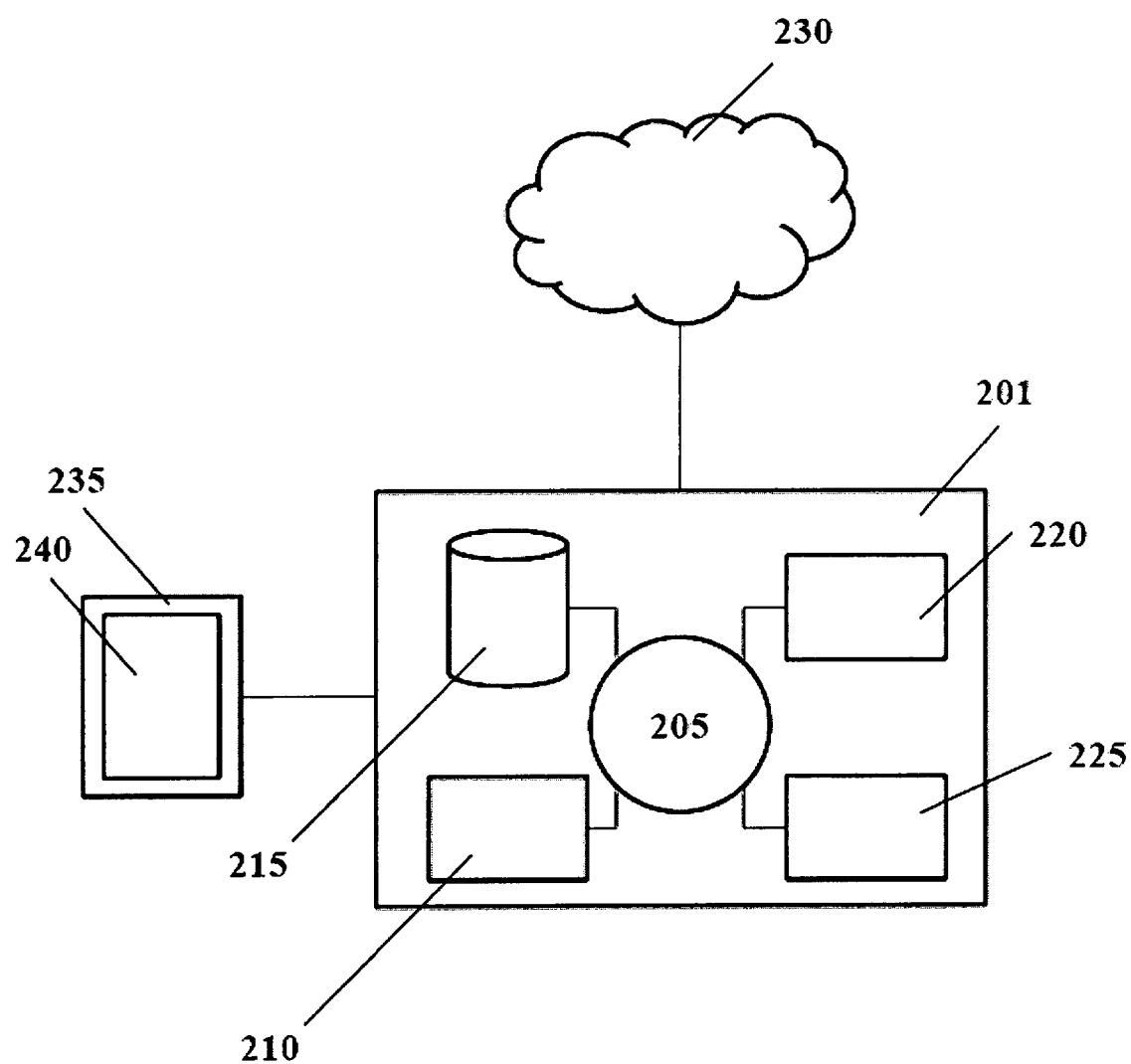
FIG. 12 shows a computer control system that is programmed or otherwise configured to implement the methods provided herein.
Figure 13A:
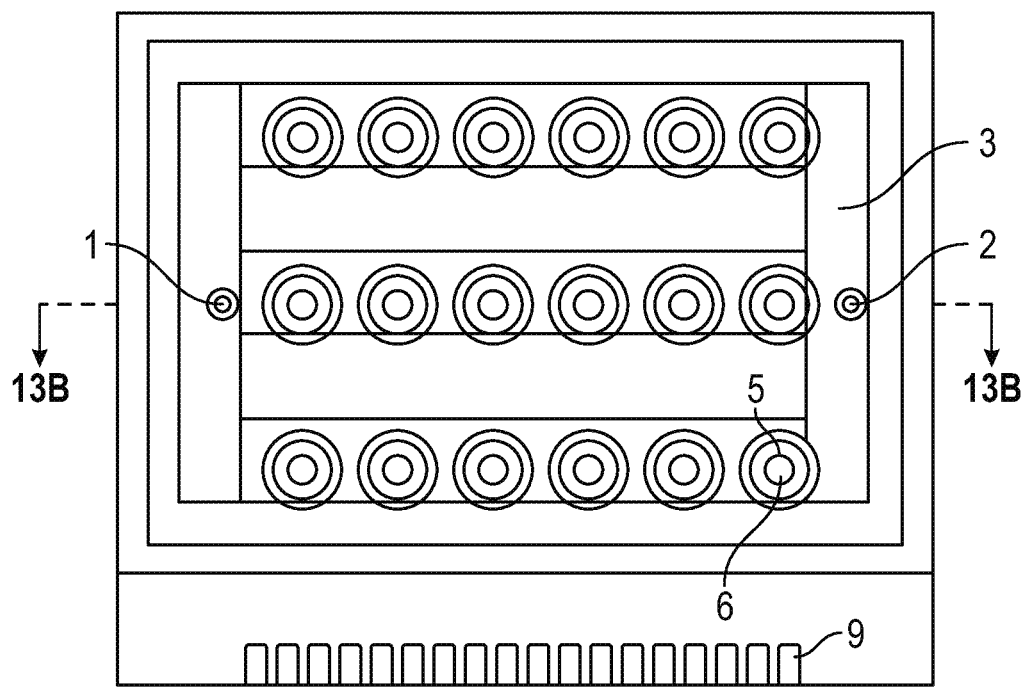
FIGS. 13A-B show a non-limiting example of a cell-based sensor device comprising an integrated, texturized semi-permeable gas exchange membrane.
Figure 13B:
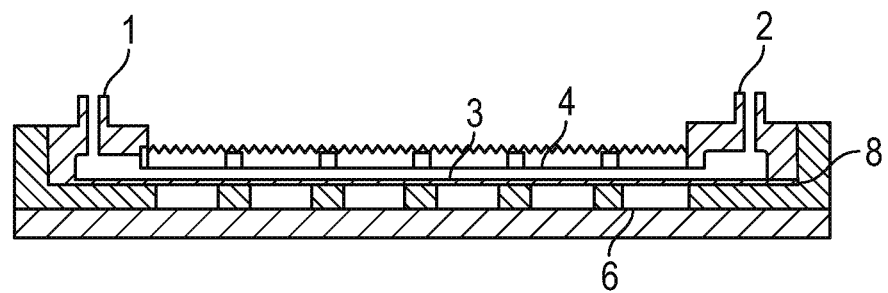
Figure 14:
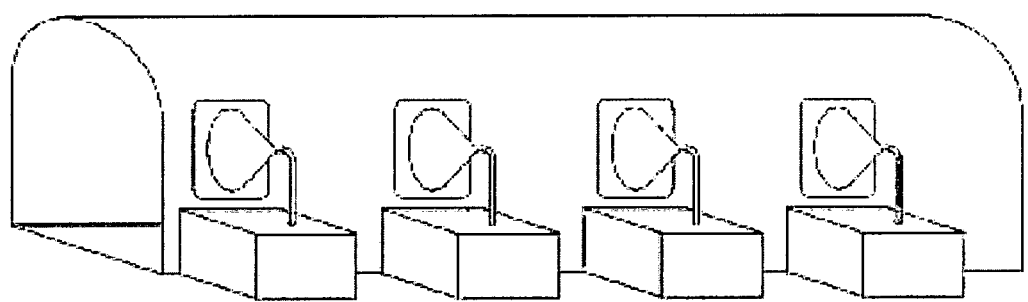
FIG. 14 shows an overview of a "smart tunnel" system configuration, including the four stage detection system and built-in neural sensor panels.
Figure 15:
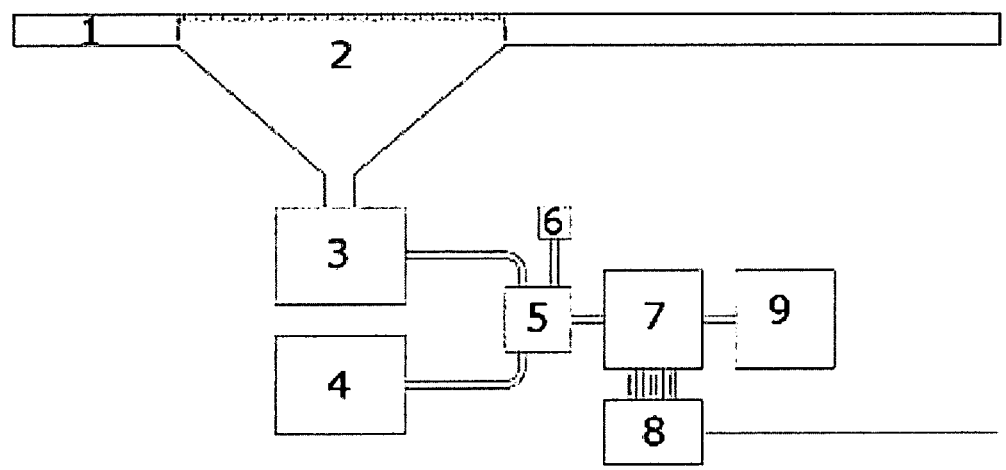
FIG. 15 shows a non-limiting schematic illustration of one of the four detection stages of the "smart tunnel" system configuration illustrated in FIG. 14.

In some embodiments, the computer system may comprise a central processing unit (CPU). FIG. 12 shows a computer system that may include a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user (e.g., portable PC, tablet PC, Smart phones). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display 235 that comprises a user interface (UI) 240 for providing, for example, a confirmation of a presence or a likelihood of a presence of a compound, such as a volatile compound. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 205. The algorithm can, for example, generate a pattern based on electrical signals received from one or more electrodes, such as a matrix of electrical signals, compare a pattern generated by the control system to one or more patterns stored in a database of the system, make a confirmation of a presence or a likelihood of a presence of a compound in sample, or any combination thereof, and others.

Applications: The cell-based sensor devices and detection systems disclosed herein may be applied to a variety of sensing applications, and in particular, to volatile compound sensing applications. Examples include, but are not limited to, monitoring produce to determine the degree of ripeness of fruit; to detect spoilage in vegetables or other food products; to detect and diagnose disease states in patients (e.g., diabetic patients); to detect the presence of airborne toxic compounds in residential, office, or commercial spaces; or to detect taggants or volatile markers for explosive materials, e.g., in airport facilities. In some cases, the disclosed sensor devices and detection systems may be used for detecting a specific odorant such as TNT and related compounds (e.g., precursor compounds, degradation products, etc.).

EXAMPLES

These examples are provided for illustrative purposes only and not to limit the scope of the claims provided herein.

Example 1 Cell-Based Sensors for Detecting a Range of Odorants, Representing a State, Such as a Ripeness State of a Single Piece of Fruit or a Batch of Fruit In some embodiments, the disclosed cell-based sensor devices and systems may be used to detect a range of odorants associated with, for example, the ripeness state of fruit. Table 1a comprises a list of odorant compounds that are produced by fruit. Table 1b comprises a list of insect odorant receptors that may bind one or more of the compounds in Table 1a.

In some embodiments of the disclosed sensor devices and systems, the cells in the sensor devices or panels may be engineered to express one or more of the insect odorant receptors listed in Table 1b. In some cases, a cell may express multiple copies of a single odorant receptor. In some cases, each cell of an array of cells may express multiple copies of a single odorant receptor. In some cases, different cells may express multiple copies of a different odorant receptor. A cell-based sensor array may comprise cells where each odorant receptor may recognize one or more of the compounds in Table 1a, and thus may detect a single odorant compound or a mixture of the odorant compounds.

In some embodiments, an air-sampling device may be used in conjunction with a sensor device or sensor panel, where the air-sampling device collects an air sample from the air that is in close proximity to the fruit and facilitates transfer of any odorant compounds contained therein into the sensor device or panel using any of the air-sampling device mechanisms described above. For example, in some cases, a cell-based sensor device may comprise a semipermeable membrane such that the odorants pass through the membrane and diffuse into the liquid medium covering the neurons on the detection device. Upon binding to the odorant receptor, one or more G-protein-coupled signaling pathways are activated inside the cell, and an action potential may be triggered. In some cases, at least one cell in each element (e.g., chamber) of an array is in contact with or in close proximity to an electrode. In some cases, at least once cell in each element of an array may at least partially engulf an electrode, e.g., a three dimensional electrode. In some cases, multiple cells in each element of an array are in contact with, in close proximity to, or at least partially engulf an electrode. In these cases, an electrical impulse generated by one or more cells of the array may be directed to a signal detector by the one or more electrodes.

An electrode may be wired such that the binding of an odorant to a particular cell results in a unique signal (based on its location in the array) such that the processor or computer used to read data from the array of electrodes may compute which cell has bound an odorant. This permits mapping back to the odorant receptor since each cell uniquely expresses a single odorant receptor. Through the decoding of odorant receptors that have generated electrical signals, one may obtain a pattern of receptors that have been activated. In some cases, a particular odorant or set of odorants may yield a particular pattern of receptor activation.

Furthermore, because the electrodes may permit measurement of sub-threshold signals (this is true for all embodiments of the disclosed sensor devices and systems described above), quantitative information may be derived from a cell, thereby yielding information related to odorant concentration. By running standard control samples across the array, a database may be generated to determine how well different compounds may be binding across the array. Furthermore, for each of these controls, detection may be performed based on a serial dilution curve, thereby allowing a pattern of electrical signals to be mapped back to the identity and concentration of a compound from an unknown sample.

That is, the pattern of compound binding and receptor activation across the array may be more than just on/off, but may also capture information related to odorant concentration levels. Thus, one can map back from the results of a test sample and may determine the identity and/or concentration of the odorant in the test sample.

In the case of multiple types of odorants binding to multiple cells on the array, a more complex signal pattern or fingerprint may be recorded for the particular mixture, since the signal pattern or fingerprint may encode compound identity information and relative concentration information with overlapping effects.

In some embodiments, the use of machine learning algorithms may be used to process sensor signals, e.g., for distinguishing between a real binding/activation event and background noise, and/or for interpreting the electrical signal pattern or fingerprint in order to improve the accuracy of compound identification or concentration determination.

TABLE 1a

Odorant compounds produced by fruit or plants.

| Compound Name | CAS # |
| --- | --- |
| alpha-ionone | 127-41-3 |
| alpha-phellandrene | 99-83-2 |
| alpha-pinene | 7785-70-8 |
| benzaldehyde | 100-52-7 |
| beta-ionone | 14901-07-6 |
| beta-pinene | 18172-67-3 |
| butyric acid | 107-92-6 |
| caryophyllen | 87-44-5 |
| damascenone | 23726-93-4 |
| delta-decalactone | 705-86-2 |
| e-2-hexenal | 6728-26-3 |
| ethyl butyrate | 105-54-4 |
| gamma-decalactone | 706-14-9 |
| geranial | 5392-40-5 |
| geraniol | 106-24-1 |
| hexanoic acid | 142-62-1 |
| hexyl acetate | 142-92-7 |
| limonene | 138-86-3 |
| linalool | 78-70-6 |
| mesifuran | 4077-47-8 |
| methyl anthranilate | 134-20-3 |
| methyl butyrate | 623-42-7 |
| neral | 5392-40-5 |
| nerolidol | 7212-44-4 |
| raspberry ketone | 5471-51-2 |

TABLE 1b

Odorant receptors for fruit-specific volatile compounds.

| Odorant | CAS # | Organism | Literature code | GenBank ID | Literture Indication | Reference |
| --- | --- | --- | --- | --- | --- | --- |
| limonene | 138-86-3 | *Apolygus lucorum* (Meyer-Dür) | AlucOR46 | NM_001190564.1 | Tuned to six plant volatiles: (S)-(−)- Limonene, (R)-(+)-Limonene, (E)-2- Hexenal, (E)-3-Hexenol, 1-Heptanol, and (1R)-(−)-Myrtenol | Zhang Z, Zhang M, Yan S, Wang G, Liu Y. A Female-Biased Odorant Receptor from *Apolygus lucorum* (Meyer-Dür) Tuned to Some Plant Odors. Int J Mol Sci. 2016 Jul. 28; 17(8). pii: E1165. doi: 10.3390/ijms17081165. PubMed PMID: 27483241; PubMed Central PMCID: PMC5000588. |
| limonene | 138-86-3 | *Megoura viciae* and *Nasonovia ribisnigri* | OBP3 from *M. viciae* | KT750882.1 | (E)-β-farnesene (−)-α-pinene, β-pinene, and limonene | Northey T, Venthur H, De Biasio F, Chauviac F X, Cole A, Ribeiro K A Junior, Grossi G, Falabella P, Field L M, Keep N H, Zhou J J. Crystal Structures and |

TABLE 1b-continued

Odorant receptors for fruit-specific volatile compounds.

| Odorant | CAS # | Organism | Literature code | GenBank ID | Literture Indication | Reference |
|---|---|---|---|---|---|---|
| | | | | | | Binding Dynamics of Odorant-Binding Protein 3 from two aphid species *Megoura viciae* and *Nasonovia ribisnigri*. Sci Rep. 2016 Apr. 22; 6: 24739. doi: 10.1038/srep24739. PubMed PMID: 27102935; PubMed Central PMCID: PMC4840437. |
| limonene | 138-86-3 | *Marucavitrata* Fabricius (Lepidoptera: Crambidae) | MvitGOBP1-2 | NP_001140185.1 | MvitGOBP1-2 had different binding affinities with 17 volatile odorant molecules including butanoic acid butyl ester, limonene, 4-ethylpropiophenone, 1H indol-4-ol, butanoic acid octyl ester, and 2 methyl-3-phenylpropanal | Zhou J, Zhang N, Wang P, Zhang S, Li D, Liu K, Wang G, Wang X, Ai H. Identification of Host-Plant Volatiles and Characterization of Two Novel General Odorant-Binding Proteins from the Legume Pod Borer, *Maruca vitrata* Fabricius (Lepidoptera: Crambidae). PLoS One. 2015 Oct. 30; 10(10): e0141208. doi: 10.1371/journal.pone.0141208. eCollection 2015. PubMed PMID: 26517714; PubMed Central PMCID: PMC4627759. |
| limonene | 138-86-3 | Vinegar fly *Drosophila melanogaster* | Odorant receptor Or19a | NP_525013.2 | Single dedicated olfactory pathway determines oviposition fruit substrate choic | Dweck H K, Ebrahim S A, Kromann S, Bown D, Hillbur Y, Sachse S, Hansson B S, Stensmyr M C. Olfactory preference for egg laying on citrus substrates in *Drosophila*. Curr Biol. 2013 Dec. 16; 23(24): 2472-80. doi: 10.1016/j.cub.2013.10.047. Epub 2013 Dec. 5. PubMed PMID: 24316206. |
| linalool | 78-70-6 | *Bombyx mori* | BmorOR-19 | NP_001091785.1 | Tuned to the detection of the plant odor linalool | Groβe-Wilde E, Stieber R, Forstner M, Krieger J, Wicher D, Hansson B S. Sex-specific odorant receptors of the tobacco hornworm *manduca sexta*. Front Cell Neurosci. 2010 Aug. 3; 4. pii: 22. doi: 10.3389/fncel.2010.00022. eCollection 2010. PubMed PMID: 20725598; PubMed Central PMCID: PMC2922936. |

TABLE 2

Examples of odorant receptors.

| Gene Name | Accession Number |
|---|---|
| odorant receptor family 7 subfamily D member 4 P79L variant [*Homo sapiens*] | ABV66285.1 |
| odorant receptor family 7 subfamily D member 4 S84N variant [*Homo sapiens*] | ABV66284.1 |
| odorant receptor family 7 subfamily D member 4 WM variant [*Homo sapiens*] | ABV66283.1 |
| odorant receptor family 7 subfamily D member 4 RT variant [*Homo sapiens*] | ABV66282.1 |
| odorant receptor HOR3'beta5 [*Homo sapiens*] | AAG42368.1 |
| odorant receptor HOR3'beta4 [*Homo sapiens*] | AAG42367.1 |
| odorant receptor HOR3'beta3 [*Homo sapiens*] | AAG42366.1 |
| odorant receptor HOR3'beta2 [*Homo sapiens*] | AAG42365.1 |
| odorant receptor HOR3'beta1 [*Homo sapiens*] | AAG42364.1 |
| olfactory receptor 7D4 [*Homo sapiens*] | NP_001005191.1 |
| HOR 5'Beta1 [*Homo sapiens*] | AAD29426.2 |
| HOR 5'Beta3 [*Homo sapiens*] | AAD29425.2 |
| F20722_2 [*Homo sapiens*] | AAC14389.1 |
| olfactory receptor 2J3 [*Homo sapiens*] | NP_001005216.2 |

TABLE 2-continued

Examples of odorant receptors.

| Gene Name | Accession Number |
|---|---|
| olfactory receptor 2H1 [*Homo sapiens*] | NP_001304951.1 |
| olfactory receptor 2H1 [*Homo sapiens*] | NP_001304943.1 |
| olfactory receptor 2H1 [*Homo sapiens*] | NP_112145.1 |
| olfactory receptor 11A1 [*Homo sapiens*] | NP_039225.1 |
| olfactory receptor 51B4 [*Homo sapiens*] | NP_149419.2 |
| olfactory receptor 51B2 [*Homo sapiens*] | NP_149420.4 |
| olfactory receptor 2J2 [*Homo sapiens*] | NP_112167.2 |
| olfactory receptor 2H2 [*Homo sapiens*] | NP_009091.3 |
| olfactory receptor 10G4 [*Homo sapiens*] | NP_001004462.1 |
| olfactory receptor 12D2 [*Homo sapiens*] | NP_039224.2 |
| olfactory receptor 2F1 [*Homo sapiens*] | NP_036501.2 |
| olfactory receptor 51M1 [*Homo sapiens*] | NP_001004756.2 |
| olfactory receptor 51I1 [*Homo sapiens*] | NP_001005288.1 |
| olfactory receptor 52D1 [*Homo sapiens*] | NP_001005163.1 |
| olfactory receptor 51I2 [*Homo sapiens*] | NP_001004754.1 |
| olfactory receptor 51B5 [*Homo sapiens*] | NP_001005567.2 |
| olfactory receptor 3A1 [*Homo sapiens*] | NP_002541.2 |
| olfactory receptor 51B6 [*Homo sapiens*] | NP_001004750.1 |
| olfactory receptor 5V1 [*Homo sapiens*] | NP_110503.3 |
| olfactory receptor 12D3 [*Homo sapiens*] | NP_112221.1 |
| olfactory receptor 10C1 [*Homo sapiens*] | NP_039229.3 |
| putative olfactory receptor 2B3 [*Homo sapiens*] | NP_001005226.1 |
| OR1F12, partial [*Homo sapiens*] | ADA83722.1 |
| OR12D3, partial [*Homo sapiens*] | ADA83721.1 |
| OR1F12, partial [*Homo sapiens*] | ADA83720.1 |
| F20722_1 [*Homo sapiens*] | AAC14388.1 |
| olfactory receptor [*Homo sapiens*] | CAD31042.1 |
| olfactory receptor [*Homo sapiens*] | CAD31041.1 |
| olfactory receptor [*Homo sapiens*] | CAD31040.1 |
| olfactory receptor [*Homo sapiens*] | CAD31039.1 |
| olfactory receptor [*Homo sapiens*] | CAD31038.1 |
| olfactory receptor [*Homo sapiens*] | CAD31037.1 |
| Olfactory receptor 51B4; Odorant receptor HOR5'beta1 | Q9Y5P0.3 |
| Olfactory receptor 51B2; Odorant receptor HOR5'beta3; Olfactory receptor 51B1 | Q9Y5P1.4 |
| Olfactory receptor 7D4; OR19-B; Odorant receptor family subfamily D member 4RT; Olfactory receptor OR19-7 | Q8NG98.1 |
| Olfactory receptor 1D2; Olfactory receptor 17-4; OR17-4; Olfactory receptor OR17-6; Olfactory receptor-like protein HGMP07E | P34982.2 |
| Olfactory receptor 12D3; Hs6M1-27; Olfactory receptor OR6-27 | Q9UGF7.1 |
| Olfactory receptor 5V1; Hs6M1-21; Olfactory receptor OR6-26 | Q9UGF6.1 |
| Olfactory receptor 11A1; Hs6M1-18; Olfactory receptor 11A2; Olfactory receptor OR6-30 | Q9GZK7.1 |
| Olfactory receptor 2H1; Hs6M1-16; OLFR42A-9004.14/9026.2; Olfactory receptor 2H6; Olfactory receptor 2H8; Olfactory receptor 6-2; OR6-2; Olfactory receptor OR6-32 | Q9GZK4.1 |
| Olfactory receptor 2J3; Hs6M1-3; Olfactory receptor OR6-16; OR6-6; Olfactory receptor 6-6 | O76001.1 |
| Receptor expression-enhancing protein 1 | Q9H902.1 |
| Receptor expression-enhancing protein 2 | Q9BRK0.2 |
| Olfactory receptor 5H8; Olfactory receptor 5H8 pseudogene; Olfactory receptor OR3-7 | P0DN80.1 |
| Olfactory receptor 13C7 | P0DN81.1 |
| Olfactory receptor 12D1; Olfactory receptor 12D1 pseudogene | P0DN82.1 |
| Putative olfactory receptor 8G3 pseudogene; Olfactory receptor OR11-297 | P0DMU2.1 |
| Putative olfactory receptor 13C6; Olfactory receptor, family 13, subfamily C, member 6 pseudogene; Olfactory receptor, family 13, subfamily C, member 7 pseudogene; Putative olfactory receptor 13C7 | Q8NH95.2 |
| Olfactory receptor 8G5; Olfactory receptor 8G6; Olfactory receptor OR11-298 | Q8NG78.2 |
| Olfactory receptor 51M1; Odorant receptor HOR5'beta7; Olfactory receptor OR11-40 | Q9H341.4 |
| Olfactory receptor 52E5 327 aa protein | Q8NH55.2 |
| Olfactory receptor 4A5; Olfactory receptor OR11-111 | Q8NH83.4 |
| Olfactory receptor 5K1; HTPCRX10; Olfactory receptor OR3-8 | Q8NHB7.2 |
| Olfactory receptor 2C1; OLFmf3; Olfactory receptor 2C2; Olfactory receptor OR16-1; Olfactory receptor OR16-2 | O95371.3 |
| Olfactory receptor 8B3; Olfactory receptor OR11-311 | Q8NGG8.3 |
| Olfactory receptor 4M2; Olfactory receptor OR15-3 | Q8NGB6.2 |
| Olfactory receptor 2H2; Hs6M1-12; Olfactory receptor 2H3; Olfactory receptor-like protein FAT11 | O95918.2 |
| Olfactory receptor 52L1; Olfactory receptor OR11-50 | Q8NGH7.4 |
| Olfactory receptor 2A14; OST182; Olfactory receptor 2A6; Olfactory receptor OR7-12 | Q96R47.4 |
| Olfactory receptor 10C1; Hs6M1-17; Olfactory receptor 10C2 | Q96KK4.3 |
| Olfactory receptor 8S1 | Q8NH09.2 |
| Olfactory receptor 8J1; Olfactory receptor OR11-183 | Q8NGP2.2 |

TABLE 2-continued

Examples of odorant receptors.

| Gene Name | Accession Number |
|---|---|
| Olfactory receptor 6Q1; Olfactory receptor OR11-226 317 aa protein | Q8NGQ2.2 |
| Olfactory receptor 4S2; Olfactory receptor OR11-137 | Q8NH73.2 |
| Olfactory receptor 52N4; Olfactory receptor OR11-64 | Q8N |
| Olfactory receptor 52K1; Olfactory receptor OR11-8 | Q8NGK4.2 |
| Olfactory receptor 52J3; Olfactory receptor OR11-32 | Q8NH60.2 |
| Olfactory receptor 52E2 | Q8NGJ4.2 |
| Olfactory receptor 52A1; HPFH1OR; Odorant receptor HOR3'beta4; Olfactory receptor OR11-319 | Q9UKL2.2 |
| Olfactory receptor 51V1; Odorant receptor HOR3'beta1; Olfactory receptor 51 A12; Olfactory receptor OR11-36 | Q9H2C8.2 |
| Olfactory receptor 51B5; Odorant receptor HOR5'beta5; Olfactory receptor OR11-37 | Q9H339.2 |
| Olfactory receptor 10A4; HP2; Olfactory receptor-like protein JCG5 | Q9H209.2 |
| Olfactory receptor 10J1; Olfactory receptor OR1-26; Olfactory receptor-like protein HGMP07J | P30954.2 |
| Olfactory receptor 4D1; Olfactory receptor 4D3; Olfactory receptor TPCR16 | Q15615.3 |
| Olfactory receptor 12D2; Hs6M1-20; Olfactory receptor OR6-28 | P58182.2 |
| Olfactory receptor 10AC1; Olfactory receptor OR7-5 | Q8NH08.2 |
| Putative olfactory receptor 3A4; Olfactory receptor 17-24; OR17-24; Olfactory receptor 3A5 | P47883.4 |
| Olfactory receptor 56A4; Olfactory receptor OR11-49 | Q8NGH8.2 |
| Olfactory receptor 52E8; Olfactory receptor OR11-54 | Q6IFG1.3 |
| Olfactory receptor 2A25; Olfactory receptor 2A27 | A4D2G3.2 |
| Olfactory receptor 4K17; Olfactory receptor OR14-29 | Q8NGC6.3 |
| Olfactory receptor 1L1; Olfactory receptor 1L2; Olfactory receptor 9-C; OR9-C; Olfactory receptor OR9-27 | Q8NH94.3 |
| Olfactory receptor 4A15; Olfactory receptor OR11-118 | Q8NGL6.3 |
| Olfactory receptor 13D1; Olfactory receptor OR9-15 | Q8NGV5.3 |
| Olfactory receptor 8B2; Olfactory receptor OR11-309 | Q96RD0.3 |
| Olfactory receptor 2T1; Olfactory receptor 1-25; OR1-25; Olfactory receptor OR1-61 | O43869.3 |
| Olfactory receptor 6K3; Olfactory receptor OR1-18 | Q8NGY3.2 |
| Olfactory receptor 4K15; Olfactory receptor OR14-20 | Q8NH41.2 |
| Olfactory receptor 2T4; Olfactory receptor OR1-60 | Q8NH00.2 |
| Olfactory roocptor 1L6; Olfactory receptor 1L7; Olfactory receptor OR9-30 | Q8NGR2.2 |
| Olfactory receptor 13A1; Olfactory receptor OR10-3 | Q8NGR1.2 |
| Olfactory receptor 56B1; Olfactory receptor OR11-65 | Q8N |
| Olfactory receptor 2AK2; Olfactory receptor 2AK1; Olfactory receptor OR1-47 335 aa protein | Q8NG84.2 |
| Olfactory receptor 3A3; Olfactory receptor 17-201; OR17-201; Olfactory receptor 3A6; Olfactory receptor 3A7; Olfactory receptor 3A8; Olfactory receptor OR17-22 | P47888.3 |
| Olfactory receptor 3A2; Olfactory receptor 17-228; OR17-228; Olfactory recentor OR17-14 | P47893.3 |
| Olfactory receptor 10R2; Olfactory receptor OR1-8 | Q8NGX6.3 |
| Olfactory receptor 52H1; Olfactory receptor OR11-45 | Q8NGJ2.3 |
| Olfactory receptor 5T2; Olfactory receptor OR11-177 | Q8NGG2.3 |
| Olfactory receptor 6S1; Olfactory receptor OR14-37 | Q8NH40.2 |
| Olfactory receptor 6K6; Olfactory receptor OR1-21 | Q8NGW6.2 |
| Olfactory receptor 5H6; Olfactory receptor OR3-11 | Q8NGV6.2 |
| Olfactory receptor 2D3; Olfactory receptor OR11-89 | Q8NGH3.2 |
| Olfactory receptor 1S2; Olfactory receptor OR11-231 | Q8NGQ3.2 |
| Olfactory receptor 52R1; Olfactory receptor OR11-22 315 aa protein | Q8NGF1.2 |
| Olfactory receptor 51F2; Olfactory receptor OR11-23 | Q8NH61.2 |
| Olfactory receptor 10S1; Olfactory receptor OR11-279 | Q8NGN2.2 |
| Olfactory receptor 52B2; Olfactory receptor OR11-70 | Q96RD2.3 |
| Olfactory receptor 52I2; Olfactory receptor OR11-12 | Q8NH67.3 |
| Olfactory receptor 52B6; Olfactory receptor OR11-47 | Q8NGF0.3 |
| Putative olfactory receptor 52L2; Olfactory receptor OR11-74 | Q8NGH6.3 |
| Olfactory receptor 2C3; Olfactory receptor 2C4; Olfactory receptor 2C5; Olfactory receptor OR1-30 | Q8N628.3 |
| Olfactory receptor 5T3; Olfactory receptor OR11-178 | Q8NGG3.3 |
| Olfactory receptor 9K2; Olfactory receptor OR12-2 | Q8NGE7.2 |
| Olfactory receptor 7G1; Olfactory receptor 19-15; OR19-15; Olfactory receptor OR19-8 | Q8NGA0.2 |
| Olfactory receptor 4N4; Olfactory receptor OR15-1; Olfactory receptor OR15-5 | Q8N0Y3.2 |
| Olfactory receptor 2K2; HTPCRH06; Olfactory receptor OR9-17 | Q8NGT1.2 |
| Olfactory receptor 1S1; Olfactory receptor OR11-232 | Q8NH92.2 |
| Olfactory receptor 1N2; Olfactory receptor OR9-23 | Q8NGR9.2 |
| Olfactory receptor 52K2; Olfactory receptor OR11-7 | Q8NGK3.2 |
| Olfactory receptor 13C3; Olfactory receptor OR9-8 | Q8NGS6.2 |
| Olfactory receptor 4A47; Olfactory receptor OR11-113 309 aa protein | Q6IF82.2 |
| Olfactory receptor 11H1; Olfactory receptor OR22-1 | Q8NG94.3 |
| Olfactory receptor 5H2; Olfactory receptor OR3-10 | Q8NGV7.3 |
| Olfactory receptor 9G4; Olfactory receptor OR11-216 | Q8NGQ1.2 |

TABLE 2-continued

Examples of odorant receptors.

| Gene Name | Accession Number |
|---|---|
| Olfactory receptor 8A1; OST025; Olfactory receptor OR11-318 | Q8NGG7.2 |
| Olfactory receptor 4C13; Olfactory receptor OR11-260 | Q8NGP0.2 |
| Olfactory receptor 1A1; Olfactory receptor 17-7; OR17-7; Olfactory receptor OR17-11 | Q9P1Q5.2 |
| Olfactory receptor 5AU1; Olfactory receptor OR14-38 | Q8NGC0.2 |
| Olfactory receptor 52N5; Olfactory receptor OR11-62 | Q8NH56.2 |
| Olfactory receptor 11G2; Olfactory receptor OR14-34 | Q8NGC1.2 |
| Olfactory receptor 2D2; HB2; Olfactory receptor 11-610; OR11-610; Olfactory receptor 2D1; Olfactory receptor OR11-88 | Q9H210.4 |
| Olfactory receptor 51B6; Odorant receptor HOR5'beta6 | Q9H340.2 |
| Olfactory receptor 14K1; Olfactory receptor 5AY1; Olfactory receptor OR1-39 | Q8NGZ2.2 |
| Putative olfactory receptor 9A1; HSHTPRX06 | Q8NGU1.2 |
| Olfactory receptor 14A2; Olfactory receptor 5AX1; Olfactory receptor OR1-31 | Q96R54.2 |
| Olfactory receptor 56A5 | P0C7T3.1 |
| Olfactory receptor 2T7; OST723; olfactory receptor OR1-44 | P0C7T2.1 |
| Putative olfactory receptor 2W5 320 aa protein | A6NFU9.1 |
| Olfactory receptor 52W1; Olfactory receptor OR11-71 | Q6IF63.2 |
| Olfactory receptor 11H12 | B2RN74.1 |
| Olfactory receptor 51JI; Odorant receptor HOR5'beta8; Olfactory receptor 51J2 | Q9H342.2 |
| Olfactory receptor 9G9 | P0C7N8.1 |
| Olfactory receptor 8U9 | P0C7N5.1 |
| Olfactory receptor 8U8 | P0C7N1.1 |
| Olfactory receptor 11H7; Olfactory receptor OR14-32 | Q8NGC8.2 |
| Olfactory receptor 1P1; Olfactory receptor 17-208; OR17-208; Olfactory receptor OR17-9 | Q8NH06.2 |
| Olfactory receptor 1E3; Olfactory receptor 17-210; OR17-210; Olfactory receptor OR17-7 | Q8WZA6.2 |
| Olfactory receptor 8J2 | Q8NGG1.2 |
| Olfactory receptor 5G3; Olfactory receptor 5G6; Olfactory receptor OR11-213 | P0C626.1 |
| Olfactory receptor 4Q2; olfactory receptor OR14-21 | P0C623.1 |
| Olfactory receptor 4E1; Olfactory receptor OR14-43 | P0C645.1 |
| Olfactory receptor 4A8; Olfactory receptor OR11-110 | P0C604.1 |
| Olfactory receptor 5AL1; Olfactory receptor OR11-184 | P0C617.1 |
| Olfactory receptor 5AC1; Olfactory receptor OR3-2 307 aa protein | P0C628.1 |
| Olfactory receptor 52Z1 | P0C646.1 |
| Olfactory receptor 10J4 | P0C629.1 |
| Olfactory receptor 4K3; Olfactory receptor OR14-14 | Q96R72.3 |
| Olfactory receptor 2T6; OST703; Olfactory receptor 2T9 | Q8NHC8.2 |
| Olfactory receptor 1B1; Olfactory receptor 9-B; OR9-B; Olfactory receptor OR9-26 | Q8NGR6.2 |
| Olfactory receptor 10X1; Olfactory receptor OR1-14 | Q8NGY0.2 |
| Olfactory receptor 51F1 319 aa protein | A6NGY5.1 |
| Olfactory receptor 2V1 | Q8NHB1.2 |
| Olfactory receptor 4C45 | A6NMZ5.1 |
| Olfactory receptor 52A4 | A6NMU1.1 |
| Olfactory receptor 5K4 | A6NMS3.1 |
| Olfactory receptor 2AG2 | A6NM03.1 |
| Olfactory receptor 5H14 | A6NHG9.1 |
| Olfactory receptor 2T8 | A6NH00.1 |
| Olfactory receptor 6C68 | A6NDL8.2 |
| Olfactory receptor 6C6 | A6NF89.1 |
| Olfactory receptor 5K3 | A6NET4.1 |
| Olfactory receptor 5H1; HTPCRX14 | A6NKK0.1 |
| Olfactory receptor 5B21 | A6NL26.1 |
| Olfactory receptor 6C76 | A6NM76.1 |
| Olfactory receptor 6C75 | A6NL08.1 |
| Olfactory receptor 6C74 | A6NCV1.1 |
| Olfactory receptor 6C70 | A6NIJ9.1 |
| Olfactory receptor 6C65 | A6NJZ3.1 |
| Olfactory receptor 5H15 | A6NDH6.1 |
| Olfactory receptor 14I1; Olfactory receptor 5BU1 | A6ND48.1 |
| Olfactory receptor 4C46 | A6NHA9.1 |
| Olfactory receptor 2AT4; Olfactory receptor OR11-265 | A6NND4.1 |
| Olfactory receptor 4F21 | O95013.2 |
| Olfactory receptor 2M5 | A3KFT3.1 |
| Olfactory receptor 2A7; Olfactory receptor OR7-18 | Q96R45.3 |
| Olfactory receptor 3A1; Olfactory receptor 17-40; OR17-40; Olfactory receptor OR17-15 | P47881.2 |
| Olfactory receptor 2J1; Hs6M1-4; Olfactory receptor 6-5; OR6-5 | Q9GZK6.2 |
| Olfactory receptor 5K2; Olfactory receptor OR3-9 | Q8NHB8.3 |
| Olfactory receptor 4D9; Olfactory receptor OR11-253 | Q8NGE8.3 |
| Olfactory receptor 10A2; HP4; Olfactory receptor OR11-86 | Q9H208.2 |
| Olfactory receptor 7C2; Olfactory receptor 19-18; OR19-18; Olfactory receptor 7C3; Olfactory receptor OR19-22 | O60412.4 |

TABLE 2-continued

Examples of odorant receptors.

| Gene Name | Accession Number |
|---|---|
| Olfactory receptor 5M3; Olfactory receptor OR11-191 | Q8NGP4.2 |
| Olfactory receptor 10V1; Olfactory receptor OR11-256 | Q8N |
| Olfactory receptor 2A5; Olfactory receptor 2A26; Olfactory receptor 2A8; Olfactory receptor 7-138/7-141; OR7-138; OR7-141 | Q96R48.2 |
| Olfactory receptor 1Q1; OST226; Olfactory receptor 1Q2; Olfactory receptor 1Q3; Olfactory receptor 9-A; 0R9-A; Olfactory receptor OR9-25; Olfactory receptor TPCR106 | Q15612.3 |
| Olfactory receptor 6C3; HSA8 | Q9NZP0.2 |
| Olfactory receptor 6C2; HSA3 | Q9NZP2.2 |
| Olfactory receptor 6C1; OST267 | Q96RD1.2 |
| Olfactory receptor 2T3 | Q8NH03.2 |
| Olfactory receptor 2M2; OST423 | Q96R28.2 |
| Olfactory receptor 5AC2; HSA1 | Q9NZP5.2 |
| Olfactory receptor 6B2; Olfactory receptor OR2-1 | Q6IFH4.2 |
| Olfactory receptor 2A2; Olfactory receptor 2A17; Olfactory receptor OR7-11 | Q6IF42.2 |
| Olfactory receptor 4C16; Olfactory receptor OR11-135 | Q8NGL9.2 |
| Olfactory receptor 2W3; Olfactory receptor 2W8; Olfactory receptor OR1-49 | Q7Z3T1.2 |
| Olfactory receptor 8G1; Olfactory receptor OR11-281; Olfactory receptor TPCR25 | Q15617.2 |
| Olfactory receptor 52A5; Odorant receptor HOR3'beta5; Olfactory receptor OR11-33 | Q9H2C5.1 |
| Olfactory receptor 5W2; Olfactory receptor 5W3; Olfactory receptor OR11-155 | Q8NH69.1 |
| Olfactory receptor 8U1 | Q8NH10.1 |
| Olfactory receptor 2T10; Olfactory receptor OR1-64 | Q8NGZ9.1 |
| Olfactory receptor 2AJ1 | Q8NGZ0.1 |
| Olfactory receptor 52M1; Olfactory receptor OR11-11 | Q8NGK5.1 |
| Olfactory receptor 9Q2 | Q8NGE9.1 |
| Olfactory receptor 2L3 | Q8NG85.1 |
| Olfactory receptor 10K2; Olfactory receptor OR1-4 | Q6IF99.1 |
| Olfactory receptor 2T2; Olfactory receptor OR1-43 | Q6IF00.1 |
| Olfactory receptor 2T5; Olfactory receptor OR1-62 | Q6IEZ7.1 |
| Olfactory receptor 4F3/4F16/4F29; Olfactory receptor OR1-1 | Q6IEY1.1 |
| Olfactory receptor 4C11; Olfactory receptor OR11-136 | Q6IEV9.1 |
| Olfactory receptor 5M10; Olfactory receptor OR11-207 | Q6IEU7.1 |
| Olfactory receptor 2G6 | Q5TZ20.1 |
| Olfactory receptor 10J3 | Q5JRS4.1 |
| Olfactory receptor 2B11 | Q5JQS5.1 |
| Putative olfactory receptor 2W6; Olfactory receptor OR6-3; Putative olfactory receptor 2W7 | Q8NHA6.1 |
| Olfactory receptor 10G6; Olfactory receptor OR11-280 | Q8NH81.1 |
| Putative olfactory receptor 10D3; HTPCRX09; Olfactory receptor OR11-293 | Q8NH80.1 |
| Olfactory receptor 11H2; Olfactory receptor OR14-1 | Q8NH07.1 |
| Olfactory receptor 2AP1; Olfactory receptor OR12-9 | Q8NGE2.1 |
| Olfactory receptor 4C5; Olfactory receptor OR11-99 | Q8NGB2.1 |
| Olfactory receptor 7E24; Olfactory receptor OR19-14 | Q6IFN5.1 |
| Olfactory receptor 8G2; Olfactory receptor 8G4; Olfactory receptor OR11-292; Olfactory receptor TPCR120 | Q6IF36.1 |
| Olfactory receptor 2T27; Olfactory receptor OR1-67 | Q8NH04.1 |
| Olfactory receptor 5T1; Olfactory receptor OR11-179 | Q8NG75.1 |
| Olfactory receptor 4D11 | Q8N |
| Olfactory receptor 4D10; Olfactory receptor OR11-251 | Q8N |
| Olfactory receptor 2T12; Olfactory receptor OR1-57 | Q8NG77.1 |
| Olfactory receptor 51D1; Olfactory receptor OR11-14 | Q8NGF3.1 |
| Olfactory receptor 2T33; Olfactory receptor OR1-56 | Q8NG76.1 |
| Olfactory receptor 1C1; Olfactory receptor OR1-42; Olfactory receptor TPCR27 | Q15619.4 |
| Olfactory receptor 52B4; Olfactory receptor OR11-3 | Q8NGK2.2 |
| Olfactory receptor 5R1; Olfactory receptor OR11-185 | Q8NH85.1 |
| Olfactory receptor 2V2; Olfactory receptor 2V3; Olfactory receptor OR5-3 | Q96R30.3 |
| Olfactory receptor 2M4; HTPCRX18; OST710; Olfactory receptor OR1-55; Olfactory receptor TPCR100 | Q96R27.2 |
| Olfactory receptor 2T34; Olfactory receptor OR1-63 | Q8NGX1.1 |
| Olfactory receptor 6A2; Olfactory receptor 11-55; OR11-55; Olfactory receptor 6A1; Olfactory receptor OR11-83; hP2 olfactory receptor | O95222.2 |
| Olfactory receptor 10W1; Olfactory receptor OR11-236 | Q8NGF6.1 |
| Olfactory receptor 10P1; Olfactory receptor 10P2; Olfactory receptor 10P3; Olfactory receptor OR12-7 | Q8NGE3.1 |
| Olfactory receptor 14C36; Olfactory receptor 5BF1; Olfactory receptor OR1-59 | Q8NHC7.1 |
| Olfactory receptor 10AG1; Olfactory receptor OR11-160 | Q8NH19.1 |
| Olfactory receptor 2T11; Olfactory receptor OR1-65 | Q8NH01.1 |
| Olfactory receptor 5M11 | Q96RB7.2 |
| Putative olfactory receptor 1F2; OLFmf2 | Q96R84.2 |
| Olfactory receptor 4F4; HS14a-1-A; Olfactory receptor OR19-3 | Q96R69.2 |
| Olfactory receptor 4C12; Olfactory receptor OR11-259 | Q96R67.2 |

TABLE 2-continued

Examples of odorant receptors.

| Gene Name | Accession Number |
|---|---|
| Olfactory receptor 5B2; OST073; Olfactory receptor OR11-240 | Q96R09.3 |
| Olfactory receptor 51E1; D-GPCR; G-protein coupled receptor 164; Olfactory receptor 52A3; Prostate-overexpressed G protein-coupled receptor; Prostate-specific G protein-coupled receptor 2 | Q8TCB6.1 |
| Putative olfactory receptor 14L1; Putative olfactory receptor 5AV1 | Q8NHC6.1 |
| Olfactory receptor 14A16; Olfactory receptor 5AT1; Olfactory receptor OR1-45 | Q8NHC5.1 |
| Olfactory receptor 10J5; Olfactory receptor OR1-28 | Q8NHC4.1 |
| Olfactory receptor IF12; Hs6M1-35P | Q8NHA8.1 |
| Olfactory receptor 2AE1; Olfactory receptor 2AE2 | Q8NHA4.1 |
| Olfactory receptor 1L3; Olfactory receptor 9-D; OR9-D; Olfactory receptor OR9-28 | Q8NH93.1 |
| Olfactory receptor 5AK2 | Q8NH90.1 |
| Putative olfactory receptor 5AK3 | Q8NH89.1 |
| Olfactory receptor 9G1; Olfactory receptor 9G5; Olfactory receptor OR11-114 | Q8NH87.1 |
| Olfactory receptor 6X1; Olfactory receptor OR11-270 | Q8NH79.1 |
| Olfactory receptor 56B4; Olfactory receptor OR11-67 | Q8NH76.1 |
| Olfactory receptor 10A6; Olfactory receptor OR11-96 | Q8NH74.1 |
| Olfactory receptor 4C6; Olfactory receptor OR11-138 | Q8NH72.1 |
| Olfactory receptor 4A16; Olfactory receptor OR11-117 | Q8NH70.1 |
| Olfactory receptor 51A7; Olfactory receptor OR11-27 | Q8NH64.1 |
| Olfactory receptor 51H1; Olfactory receptor OR11-25 | Q8NH63.1 |
| Putative olfactory receptor 52P1 | Q8NH57.2 |
| Olfactory receptor 56A3; Olfactory receptor 56A6 | Q8NH54.2 |
| Olfactory receptor 52N1; Olfactory receptor OR11-61 | Q8NH53.1 |
| Olfactory receptor 8K3; Olfactory receptor OR11-181 | Q8NH51.1 |
| Olfactory receptor 8K5; Olfactory receptor OR11-174 | Q8NH50.1 |
| Olfactory receptor 4X1; Olfactory receptor OR11-104 | Q8NH49.1 |
| Olfactory receptor 5B3; Olfactory receptor 5B13; Olfactory receptor OR11-239 | Q8NH48.1 |
| Olfactory receptor 4L1; Olfactory receptor 4L2; Olfactory receptor OR14-28 | Q8NH43.1 |
| Olfactory receptor 4K13; Olfactory receptor OR14-27 | Q8NH42.1 |
| Olfactory receptor 4C3; Olfactory receptor OR11-98 | Q8NH37.2 |
| Olfactory receptor 4F5 | Q8NH21.1 |
| Olfactory receptor 4Q3; Olfactory receptor 4Q4; Olfactory receptor OR14-3 | Q8NH05.1 |
| Olfactory receptor 2T29 315 aa protein | Q8NH02.2 |
| Olfactory receptor 6F1; Olfactory receptor OR1-38 | Q8NGZ6.1 |
| Olfactory receptor 2G2; Olfactory receptor OR1-32 | Q8NGZ5.1 |
| Olfactory receptor 2G3; Olfactory receptor OR1-33 309 aa protein | Q8NGZ4.1 |
| Olfactory receptor 13G1; Olfactory receptor OR1-37 | Q8NGZ3.1 |
| Olfactory receptor 2L8; Olfactory receptor OR1-46 | Q8NGY9.1 |
| Putative olfactory receptor 10J6 | Q8NGY7.1 |
| Olfactory receptor 6N2; Olfactory receptor OR1-23 | Q8NGY6.1 |
| Olfactory receptor 6N1 | Q8NGY5.1 |
| Olfactory receptor 6K2; Olfactory receptor OR1-17 | Q8NGY2.1 |
| Olfactory receptor 10Z1; Olfactory receptor OR.1-15 | Q8NGY1.1 |
| Olfactory receptor 6P1; Olfactory receptor OR1-12 | Q8NGX9.1 |
| Olfactory receptor 6Y1; Olfactory receptor 6Y2; Olfactory receptor OR1-11 | Q8NGX8.1 |
| Olfactory receptor 10K1; Olfactory receptor OR1-6 | Q8NGX5.1 |
| Olfactory receptor 10T2; Olfactory receptor OR1-3 | Q8NGX3.1 |
| Olfactory receptor 11L1 | Q8NGX0.1 |
| Olfactory receptor 2Y1; Olfactory receptor OR5-2 | Q8NGV0.1 |
| Putative olfactory receptor 2I1; Putative olfactory receptor 2I2; Putative olfactory receptor 2I3; Putative olfactory receptor 2I4 | Q8NGU4.1 |
| Olfactory receptor 9A4; Olfactory receptor OR7-1 | Q8NGU2.1 |
| Olfactory receptor 2A1/2A42; Olfactory receptor OR7-16; Olfactory receptor OR7-19 | Q8NGT9.2 |
| Olfactory receptor 9A2; Olfactory receptor OR7-2 | Q8NGT5.1 |
| Olfactory receptor 13J1; Olfactory receptor OR9-2 | Q8NGT2.1 |
| Olfactory receptor 13C9; Olfactory receptor OR9-13 | Q8NGT0.1 |
| Olfactory receptor 13C2; Olfactory receptor OR9-12 | Q8NGS9.1 |
| Olfactory receptor 13C5; Olfactory receptor OR9-11 | Q8NGS8.1 |
| Olfactory receptor 13C8 | Q8NGS7.1 |
| Olfactory receptor 13F1; Olfactory receptor OR9-6 | Q8NGS4.1 |
| Olfactory receptor 1J1; Olfactory receptor OR9-18 | Q8NGS3.1 |
| Olfactory receptor 1J2; HSA5; HTPCRX15; OST044; Olfactory receptor 1J3; Olfactory receptor 1J5; Olfactory receptor OR9-19 | Q8NGS2.1 |
| Olfactory receptor 1J4; HTPCRX01; Olfactory receptor OR9-21 | Q8NGS1.1 |
| Olfactory receptor 1N1; Olfactory receptor 1-26; OR1-26; Olfactory receptor 1N3; Olfactory receptor OR9-22 | Q8NGS0.1 |
| Olfactory receptor 1L8; Olfactory receptor OR9-24 | Q8NGR8.1 |
| Olfactory receptor 1L4; OST046; Olfactory receptor 1L5; Olfactory receptor 9-E; OR9-E; Olfactory receptor OR9-29 | Q8NGR5.1 |
| Olfactory receptor 5C1; Olfactory receptor 5C2; Olfactory receptor 9-F; OR9-F | Q8NGR4.1 |
| Olfactory receptor 1K1 | Q8NGR3.1 |
| Olfactory receptor 9I1; Olfactory receptor OR11-228 | Q8NGQ6.1 |

TABLE 2-continued

Examples of odorant receptors.

| Gene Name | Accession Number |
|---|---|
| Olfactory receptor 9Q1 | Q8NGQ5.1 |
| Olfactory receptor 10Q1; Olfactory receptor OR11-233 | Q8NGQ4.1 |
| Olfactory receptor 5M1; OST050; Olfactory receptor OR11-208 | Q8NGP8.1 |
| Olfactory receptor 5M8; Olfactory receptor OR11-194 | Q8NGP6.1 |
| Olfactory receptor 5M9; Olfactory receptor OR11-190 | Q8NGP3.1 |
| Putative olfactory receptor 4A4; Olfactory receptor OR11-107 | Q8NGN8.1 |
| Putative olfactory receptor 10D4 | Q8NGN7.1 |
| Olfactory receptor 10G7; Olfactory receptor OR11-283 | Q8NGN6.1 |
| Olfactory receptor 10G8; Olfactory receptor OR11-282 | Q8NGN5.1 |
| Olfactory receptor 10G9; Olfactory receptor 10G10 | Q8NGN4.1 |
| Olfactory receptor 10G4; Olfactory receptor OR11-278 | Q8NGN3.1 |
| Olfactory receptor 6T1; Olfactory receptor OR11-277 | Q8NGN1.1 |
| Olfactory receptor 4D5; Olfactory receptor OR11-276 | Q8NGN0.1 |
| Olfactory receptor 8D4; Olfactory receptor OR11-275 | Q8NGM9.1 |
| Olfactory receptor 6M1; Olfactory receptor OR11-271 | Q8NGM8.1 |
| Olfactory receptor 4C15; Olfactory receptor OR11-127; Olfactory receptor OR11-134 | Q8NGM1.1 |
| Olfactory receptor 4P4; Olfactory receptor 4P3 | Q8NGL7.1 |
| Olfactory receptor 5D13; Olfactory receptor OR11-142; Olfactory receptor OR11-148 | Q8NGL4.2 |
| Olfactory receptor 5D14; Olfactory receptor OR11-141; Olfactory receptor OR11-150 | Q8NGL3.1 |
| Olfactory receptor 5L1; OST262; Olfactory receptor OR11-151 | Q8NGL2.1 |
| Olfactory receptor 5D18; Olfactory receptor OR11-143; Olfactory receptor OR11-152 | Q8NGL1.1 |
| Olfactory receptor 5L2; HTPCRX16; Olfactory receptor OR11-153 | Q8NGL0.1 |
| Olfactory receptor 5D16; Olfactory receptor OR11-154 | Q8NGK9.1 |
| Olfactory receptor 5211; Olfactory receptor OR11-13 | Q8NGK6.2 |
| Olfactory receptor 51G1; Olfactory receptor 51G3; Olfactory receptor OR11-29 | Q8NGK1.1 |
| Olfactory receptor 51G2; Olfactory receptor OR11-28 | Q8NGK0.1 |
| Olfactory receptor 51T1; Olfactory receptor OR11-26 | Q8NGJ9.1 |
| Olfactory receptor 51S1; Olfactory receptor OR11-24 | Q8NGJ8.1 |
| Olfactory receptor 51A2 | Q8NGJ7.1 |
| Olfactory receptor 51A4 | Q8NGJ6.1 |
| Olfactory receptor 51LI; Olfactory receptor OR11-31 | Q8NGJ5.1 |
| Olfactory receptor 52E1 | Q8NGJ3.1 |
| Olfactory receptor 4D6; Olfactory receptor OR11-250 | Q8NGJ1.1 |
| Olfactory receptor 5A1; OST181; Olfactory receptor OR11-249 | Q8NGJ0.1 |
| Olfactory receptor 5AN1; Olfactory receptor OR11-244 | Q8N |
| Putative olfactory receptor 56B2 | Q8N |
| Olfactory receptor 52N2; Olfactory receptor OR11-57 | Q8N |
| Olfactory receptor 52E4; Olfactory receptor OR11-55 | Q8NGH9.1 |
| Olfactory receptor 8B12; Olfactory receptor OR11-317 | Q8NGG6.1 |
| Olfactory receptor 8K1; Olfactory receptor OR11-182 | Q8NGG5.1 |
| Olfactory receptor 8H1; Olfactory receptor OR11-180 | Q8NGG4.1 |
| Olfactory receptor 8J3; Olfactory receptor OR11-173 | Q8NGG0.1 |
| Olfactory receptor 4X2; Olfactory receptor OR11-105 | Q8NGF9.1 |
| Olfactory receptor 4B1; OST208; Olfactory receptor OR11-106 | Q8NGF8.1 |
| Olfactory receptor 5B17; Olfactory receptor 5B20; Olfactory receptor OR11-237 | Q8NGF7.1 |
| Olfactory receptor 10A7; Olfactory receptor OR12-6 | Q8NGE5.1 |
| Olfactory receptor 4K14; Olfactory receptor OR14-22 | Q8NGD5.1 |
| Olfactory receptor 4K1; Olfactory receptor OR14-19 | Q8NGD4.1 |
| Olfactory receptor 4K5; Olfactory receptor OR14-16 | Q8NGD3.1 |
| Olfactory receptor 4K2; Olfactory receptor OR14-15 | Q8NGD2.1 |
| Olfactory receptor 4N2; Olfactory receptor OR14-13; Olfactory receptor OR14-8 | Q8NGD1.1 |
| Olfactory receptor 4M1; Olfactory receptor OR14-7 | Q8NGD0.1 |
| Olfactory receptor 11H4; Olfactory receptor OR14-36 | Q8NGC9.1 |
| Olfactory receptor 11H6; Olfactory receptor OR14-35 | Q8NGC7.1 |
| Olfactory receptor 6J1; Olfactory receptor 6J2 | Q8NGC5.1 |
| Olfactory receptor 10G3; Olfactory receptor OR14-40 | Q8NGC4.1 |
| Olfactory receptor 10G2 | Q8NGC3.1 |
| Olfactory receptor 4E2; Olfactory receptor OR14-42 | Q8NGC2.1 |
| Olfactory receptor 4F6; Olfactory receptor 4F12; Olfactory receptor OR15-15 | Q8NGB9.1 |
| Olfactory receptor 4F15; Olfactory receptor OR15-14 | Q8NGB8.1 |
| Olfactory receptor 4S1; Olfactory receptor OR11-100 | Q8NGB4.1 |
| Olfactory receptor 4F17; Olfactory receptor 4F11; Olfactory receptor 4F18; Olfactory receptor 4F19 | Q8NGA8.1 |
| Olfactory receptor 10H5; Olfactory receptor OR19-25; Olfactory receptor OR19-26 | Q8NGA6.1 |
| Olfactory receptor 10H4; Olfactory receptor OR19-28 | Q8NGA5.1 |
| Putative olfactory receptor 7A2; Putative olfactory receptor 7A7 | Q8NGA2.1 |
| Olfactory receptor 1M1; Olfactory receptor 19-6; OR19-6; Olfactory receptor OR19-5 | Q8NGA1.1 |

TABLE 2-continued

Examples of odorant receptors.

| Gene Name | Accession Number |
| --- | --- |
| Olfactory receptor 7G2; OST260; Olfactory receptor 19-13; OR19-13; Olfactory receptor OR19-6 | Q8NG99.1 |
| Olfactory receptor 2Z1; Olfactory receptor 2Z2; Olfactory receptor OR19-4 | Q8NG97.1 |
| Olfactory receptor 7G3; OST085; Olfactory receptor OR19-9 | Q8NG95.1 |
| Olfactory receptor 13H1; Olfactory receptor ORX-1 | Q8NG92.1 |
| Olfactory receptor 8H2; Olfactory receptor OR11-171 | Q8N162.1 |
| Olfactory receptor 6V1; Olfactory receptor OR7-3 | Q8N148.1 |
| Olfactory receptor 8H3; Olfactory receptor OR11-172 | Q8N146.1 |
| Olfactory receptor 5AS1; Olfactory receptor OR11-168 | Q8N127.1 |
| Olfactory receptor 8I2; Olfactory receptor OR11-170 | Q8N0Y5.1 |
| Putative olfactory receptor 2B8; Hs6M1-29P | P59922.1 |
| Olfactory receptor 5J2; Olfactory receptor OR11-266 | Q8NH18.1 |
| Olfactory receptor 2A12; Olfactory receptor OR7-10 | Q8NGT7.1 |
| Olfactory receptor 2M7; Olfactory receptor OR1-58 | Q8NG81.1 |
| Olfactory receptor 2L5; Olfactory receptor 2L11; Olfactory receptor OR1-53 | Q8NG80.1 |
| Olfactory receptor 2L13; Olfactory receptor 2L14 | Q8N349.1 |
| Olfactory receptor 51Q1 | Q8NH59.2 |
| Olfactory receptor 2L2; HTPCRH07; Olfactory receptor 2L12; Olfactory receptor 2L4 | Q8NH16.1 |
| Olfactory receptor 2T35; Olfactory receptor OR1-66 | Q8NGX2.1 |
| Olfactory receptor 6B3; Olfactory receptor OR2-2 | Q8NGW1.1 |
| Olfactory receptor 6C4; Olfactory receptor OR12-10 | Q8NGE1.1 |
| Olfactory receptor 10AD1; Olfactory receptor OR12-1 | Q8NGE0.1 |
| Olfactory receptor 2M3; Olfactory receptor 2M6; Olfactory receptor OR1-54 | Q8NG83.1 |
| Olfactory receptor 1D4; Olfactory receptor 17-30; OR17-30 | P47884.3 |
| Olfactory receptor 7D2; HTPCRH03; Olfactory receptor 19-4; OR19-4; Olfactory receptor OR19-10 | Q96RA2.2 |
| Olfactory receptor 13C4; Olfactory receptor OR9-7 | Q8NGS5.1 |
| Olfactory receptor 5AR1; Olfactory receptor OR11-209 | Q8NGP9.1 |
| Olfactory receptor 5A2; Olfactory receptor OR11-248 | Q8N |
| Olfactory receptor 5AP2 | Q8NGF4.1 |
| Olfactory receptor 4N5; Olfactory receptor OR14-33 | Q8IXE1.1 |
| Olfactory receptor 52E6; Olfactory receptor OR11-58 | Q96RD3.2 |
| Olfactory receptor 8B4; Olfactory receptor OR11-315 | Q96RC9.2 |
| Olfactory receptor 5B12; Olfactory receptor 5B16; Olfactory receptor OR11-241 | Q96R08.2 |
| Olfactory receptor 5P3; Olfactory receptor OR11-94; Olfactory receptor-like protein JCG1 | Q8WZ94.1 |
| Olfactory receptor 5P2; Olfactory receptor-like protein JCG3 | Q8WZ92.1 |
| Olfactory receptor 8D1; OST004; Olfactory receptor 8D3; Olfactory receptor OR11-301; Olfactory receptor-like protein JCG9 | Q8WZ84.1 |
| Olfactory receptor 52D1; Odorant receptor HOR5'beta14; Olfactory receptor OR11-43 | Q9H346.1 |
| Olfactory receptor 51I2; Odorant receptor HOR5'beta12; Olfactory receptor OR11-38 | Q9H344.1 |
| Olfactory receptor 51I1; Odorant receptor HOR5'beta11; Olfactory receptor OR11-39 | Q9H343.1 |
| Olfactory receptor 10H1; Olfactory receptor OR19-27 | Q9Y4A9.1 |
| Olfactory receptor 2W1; Hs6M1-15; Olfactory receptor OR6-13 | Q9Y3N9.1 |
| Olfactory receptor 14J1; Hs6M1-28; Olfactory receptor 5U1; Olfactory receptor OR6-25 | Q9UGF5.1 |
| Olfactory receptor 2S2; Olfactory receptor OR9-3 | Q9NQN1.2 |
| Olfactory receptor 10A5; HP3; Olfactory receptor 10A1; Olfactory receptor 11-403; OR11-403; Olfactory receptor-like protein JCG6 | Q9H207.1 |
| Olfactory receptor 2AG1; HT3; Olfactory receptor 2AG3; Olfactory receptor OR11-79 | Q9H205.2 |
| Olfactory receptor 8D2; Olfactory receptor OR11-303; Olfactory receptor-like protein JCG2 | Q9GZM6.1 |
| Olfactory receptor 2B2; Hs6M1-10; Olfactory receptor 2B9; Olfactory receptor 6-1; OR6-1 | Q9GZK3.1 |
| Olfactory receptor 7A5; Olfactory receptor OR19-17; Olfactory receptor TPCR92 | Q15622.2 |
| Olfactory receptor 8B8; Olfactory receptor TPCR85; Olfactory-like receptor JCG8 | Q15620.2 |
| Olfactory receptor 10A3; HTPCRX12; Olfactory receptor OR11-97 | P58181.1 |
| Olfactory receptor 4D2; B-lymphocyte membrane protein BC2009; Olfactory receptor OR17-24 | P58180.1 |
| Olfactory receptor 2B6; Hs6M1-32; Olfactory receptor 2B1; Olfactory receptor 2B5; Olfactory receptor 5-40; OR5-40; Olfactory receptor 6-31; OR6-31; Olfactory receptor OR6-4 | P58173.1 |
| Olfactory receptor 1D5; Olfactory receptor 17-31; OR17-31 | P58170.1 |
| Olfactory receptor 5F1; Olfactory receptor 11-10; OR11-10; Olfactory receptor OR11-167 | O95221.2 |
| Olfactory receptor 2A4; Olfactory receptor 2A10; Olfactory receptor OR6-37 | O95047.1 |
| Olfactory receptor 6B1; Olfactory receptor 7-3; OR7-3; Olfactory receptor OR7-9 | O95007.1 |

TABLE 2-continued

Examples of odorant receptors.

| Gene Name | Accession Number |
|---|---|
| Olfactory receptor 2F2; Olfactory receptor 7-1; OR7-1; Olfactory receptor OR7-6 | O95006.1 |
| Olfactory receptor 7A10; OST027; Olfactory receptor OR19-18 | O76100.1 |
| Olfactory receptor 2J2; Hs6M1-6; Olfactory receptor 6-8; OR6-8; Olfactory receptor OR6-19 | O76002.1 |
| Putative olfactory receptor 2B3; Hs6M1-1; Olfactory receptor OR6-14; OR6-4; Olfactory receptor 6-4 | O76000.1 |
| Olfactory receptor 1I1; Olfactory receptor 19-20; OR19-20 | O60431.1 |
| Olfactory receptor 10H3; Olfactory receptor OR19-24 | O60404.1 |
| Olfactory receptor 10H2; Olfactory receptor OR19-23 | O60403.1 |
| Olfactory receptor 7A17 | O14581.1 |
| Olfactory receptor 2F1; Olfactory receptor 2F3; Olfactory receptor 2F4; Olfactory receptor 2F5; Olfactory receptor-like protein OLF3 | Q13607.2 |
| Olfactory receptor 1G1; Olfactory receptor 17-209; OR17-209; Olfactory receptor 1G2; Olfactory receptor OR17-8 | P47890.2 |
| Olfactory receptor 1E2; Olfactory receptor 17-93/17-135/17-136; OR17-135; OR17-136; OR17-93; Olfactory receptor 1E4 | P47887.2 |
| Olfactory receptor 1A2; Olfactory receptor 17-6; OR17-6; Olfactory receptor OR17-10 | Q9Y585.1 |
| Olfactory receptor 7C1; Olfactory receptor 7C4; Olfactory receptor OR19-16; Olfactory receptor TPCR86 | O76099.1 |
| Olfactory receptor 1F1; Olfactory receptor 16-35; OR16-35; Olfactory receptor 1F10; Olfactory receptor 1F4; Olfactory receptor 1F5; Olfactory receptor 1F6; Olfactory receptor 1F7; Olfactory receptor 1F8; Olfactory receptor 1F9; Olfactory receptor OR16-4 | O43749.1 |
| Olfactory receptor 5I1; Olfactory receptor OR11-159; Olfactory receptor-like protein OLF1 | Q13606.1 |
| Olfactory receptor 1E1; Olfactory receptor 13-66; OR13-66; Olfactory receptor 17-2/17-32; OR17-2; OR17-32; Olfactory receptor 1E5; Olfactory receptor 1E6; Olfactory receptor 5-85; OR5-85; Olfactory receptor OR17-18; Olfactory receptor-like protein HGMP07I | P30953.1 |
| Olfactory receptor 56A1; Olfactory receptor OR11-75 | Q8NGH5.3 |
| putative odorant receptor 71a [Talaromyces marneffei PM1] | KFX53697.1 |
| hypothetical protein XK86_18365 [Hafnia alvei] | KKI42162.1 |
| hypothetical protein PAST3_12155 [Propionibacterium acnes HL201PA1] | KFC15621.1 |
| hypothetical protein Odosp 2381 [Odoribacter splanchnicus DSM 20712] | ADY33373.1 |
| hypothetical protein LLB_1684 [Le Glonella longbeachae D-4968] | EEZ96489.1 |
| hypothetical protein cypCar_00040615 [Cyprinus carpio] | KTG44310.1 |
| hypothetical protein cypCar_00022850 [Cyprinus carpio] | KTF94953.1 |
| hypothetical protein cypCar_00047049 [Cyprinus carpio] | KTF88600.1 |
| hypothetical protein cypCar_00047378 [Cyprinus carpio] | KTF77827.1 |
| hypothetical protein cypCar_00040594 [Cyprinus carpio] | KTF73152.1 |

TABLE 3

Odorant receptors.

| Gene Name | Accession Number |
|---|---|
| odorant receptor [Ostrinia nubilalis] 333 aa protein | BAJ61939.1 GI: 319918821 |
| odorant receptor, partial [Ostrinia nubilalis] 419 aa protein | BAJ61937.1 GI: 319918818 |
| odorant receptor, partial [Ostrinia nubilalis] 314 aa protein | BAJ61935.1 GI: 319918814 |
| odorant receptor [Ostrinia nubilalis] 422 aa protein | BAJ61934.1 GI: 319918812 |
| odorant receptor [Ostrinia nubilalis] 408 aa protein | BAJ61933.1 GI: 319918810 |
| odorant receptor [Ostrinia nubilalis] 424 aa protein | BAJ61932.1 GI: 319918808 |
| odorant receptor [Ostrinia nubilalis] 424 aa protein | BAJ61929.1 GI: 319918797 |
| odorant receptor [Ostrinia nubilalis] 425 aa protein | BAJ61928.1 GI: 319918796 |
| odorant receptor, partial [Ostrinia nubilalis] 89 aa protein | BAJ61938.1 GI: 319918819 |
| odorant receptor, partial [Ostrinia nubilalis] 136 aa protein | BAJ61936.1 GI: 319918816 |
| odorant receptor, partial [Ostrinia nubilalis × Ostrinia scapulalis] 200 aa protein | BAJ61931.1 GI: 319918803 |
| odorant receptor, partial [Ostrinia nubilalis × Ostrinia scapulalis] 200 aa protein | BAJ61930.1 GI: 319918801 |
| odorant receptor, partial [Ostrinia palustralis] 383 aa protein | BAI66637.3 GI: 310688057 |
| odorant receptor, partial [Ostrinia nubilalis] 380 aa protein | BAI66625.3 GI: 310688051 |
| odorant receptor, partial [Ostrinia zaguliaevi] 412 aa protein | BAJ22892.1 GI: 308522556 |
| odorant receptor, partial [Ostrinia furnacalis] 406 aa protein | BAJ22891.1 GI: 308522554 |
| odorant receptor, partial [Ostrinia scapulalis] 396 aa protein | BAJ22890.1 GI: 308522552 |
| odorant receptor, partial [Ostrinia scapulalis] 406 aa protein | BAJ22889.1 GI: 308522550 |
| odorant receptor, partial [Ostrinia zealis] 408 aa protein | BAI66649.1 GI: 284010028 |
| odorant receptor, partial [Ostrinia zealis] 397 aa protein | BAI66648.1 GI: 284010026 |
| odorant receptor, partial [Ostrinia zealis] 409 aa protein | BAI66647.1 GI: 284010024 |
| odorant receptor, partial [Ostrinia zealis] 407 aa protein | BAI66646.1 GI: 284010022 |

TABLE 3-continued

Odorant receptors.

| Gene Name | Accession Number |
|---|---|
| odorant receptor, partial [Ostrinia zealis] 409 aa protein | BAI66645.1 GI: 284010020 |
| odorant receptor, partial [Ostrinia zealis] 409 aa protein | BAI66644.1 GI: 284010018 |
| odorant receptor, partial [Ostrinia zaguliaevi] 397 aa protein | BAI66642.1 GI: 284010014 |
| odorant receptor, partial [Ostrinia zaguliaevi] 409 aa protein | BAI66640.1 GI: 284010010 |
| odorant receptor, partial [Ostrinia zaguliaevi] 406 aa protein | BAI66639.1 GI: 284010008 |
| odorant receptor, partial [Ostrinia zaguliaevi] 409 aa protein | BAI66638.1 GI: 284010006 |
| odorant receptor, partial [Ostrinia palustralis] 397 aa protein | BAI66636.1 GI: 284010002 |
| odorant receptor, partial [Ostrinia palustralis] 407 aa protein | BAI66635.1 GI: 284010000 |
| odorant receptor, partial [Ostrinia palustralis] 409 aa protein | BAI66634.1 GI: 284009998 |
| odorant receptor, partial [Ostrinia ovalipennis] 408 aa protein | BAI66633.1 GI: 284009996 |
| odorant receptor, partial [Ostrinia ovalipennis] 323 aa protein | BAI66632.1 GI: 284009994 |
| odorant receptor, partial [Ostrinia ovalipennis] 366 aa protein | BAI66631.1 GI: 284009992 |
| odorant receptor, partial [Ostrinia ovalipennis] 406 aa protein | BAI66630.1 GI: 284009990 |
| odorant receptor, partial [Ostrinia nubilalis] 397 aa protein | BAI66627.1 GI: 284009984 |
| odorant receptor, partial [Ostrinia nubilalis] 416 aa protein | BAI66626.1 GI: 284009982 |
| odorant receptor, partial [Ostrinia nubilalis] 407 aa protein | BAI66624.1 GI: 284009978 |
| odorant receptor, partial [Ostrinia nubilalis] 409 aa protein | BAI66623.1 GI: 284009976 |
| odorant receptor, partial [Ostrinia latipennis] 323 aa protein | BAI66621.1 GI: 284009972 |
| odorant receptor, partial [Ostrinia latipennis] 350 aa protein | BAI66620.1 GI: 284009970 |
| odorant receptor, partial [Ostrinia latipennis] 366 aa protein | BAI66619.1 GI: 284009968 |
| odorant receptor, partial [Ostrinia latipennis] 407 aa protein | BAI66618.1 GI: 284009966 |
| odorant receptor, partial [Ostrinia furnacalis] 408 aa protein | BAI66616.1 GI: 284009962 |
| odorant receptor, partial [Ostrinia furnacalis] 396 aa protein | BAI66615.1 GI: 284009960 |
| odorant receptor, partial [Ostrinia furnacalis] 408 aa protein | BAI66614.1 GI: 284009958 |
| odorant receptor, partial [Ostrinia furnacalis] 408 aa protein | BAI66613.1 GI: 284009956 |
| odorant receptor, partial [Ostrinia furnacalis] 407 aa protein | BAI66612.1 GI: 284009954 |
| odorant receptor, partial [Ostrinia furnacalis] 409 aa protein | BAI66611.1 GI: 284009952 |
| odorant receptor [Ostrinia scapulalis] 422 aa protein | BAI66610.1 GI: 284009950 |
| odorant receptor [Ostrinia scapulalis] 408 aa protein | BAI66609.1 GI: 284009948 |
| odorant receptor [Ostrinia scapulalis] 424 aa protein | BAI66608.1 GI: 284009946 |
| odorant receptor [Ostrinia scapulalis] 433 aa protein | BAI66607.1 GI: 284009944 |
| odorant receptor [Ostrinia scapulalis] 422 aa protein | BAI66605.1 GI: 284009940 |
| odorant receptor [Ostrinia scapulalis] 425 aa protein | BAI66604.1 GI: 284009938 |
| odorant receptor, partial [Ostrinia ovalipennis] 304 aa protein | BAI66629.3 GI: 310688055 |
| odorant receptor, partial [Ostrinia nubilalis] 275 aa protein | BAI66628.2 GI: 310688053 |
| odorant receptor, partial [Ostrinia zaguliaevi] 291 aa protein | BAI66643.1 GI: 284010016 |
| odorant receptor, partial [Ostrinia latipennis] 291 aa protein | BAI66622.1 GI: 284009974 |
| odorant receptor, partial [Ostrinia latipennis] 318 aa protein | BAI66617.1 GI: 284009964 |
| Odorant receptor coreceptor; AgOr7; Gustatory and odorant receptor 7 478 aa protein | Q7QCC7.3 GI: 158563992 |
| Odorant receptor coreceptor; Gustatory and odorant receptor 7 478 aa protein | Q178U6.1 GI: 122117922 |
| Putative odorant receptor 19b 387 aa protein | Q8IRZ5.1 GI: 55584079 |
| Putative odorant receptor 69a, isoform A 393 aa protein | Q9VU27.2 GI: 41393542 |
| Putative odorant receptor 69a, isoform B 393 aa protein | P82985.1 GI: 14285634 |
| Putative odorant receptor 65c 410 aa protein | P82984.2 GI: 108935862 |
| Putative odorant receptor 65b 406 aa protein | P82983.2 GI: 108935861 |
| Putative odorant receptor 98b 384 aa protein | Q9VAW0.3 GI: 92090622 |
| Putative odorant receptor 85e 467 aa protein | P81924.3 GI: 54041947 |
| Putative odorant receptor 71a 378 aa protein | Q9VUK5.4 GI: 50403809 |
| Putative odorant receptor 92a 408 aa protein | Q9VDM1.3 GI: 33860192 |
| Putative odorant receptor 83c 397 aa protein | Q9VNK9.2 GI: 14285641 |
| Putative odorant receptor 59c 411 aa protein | Q9W1P7.1 GI: 11387002 |
| Putative odorant receptor 85d 412 aa protein | Q9VHQ2.1 GI: 11386992 |
| Putative odorant receptor 13a [Cerapachys biroi] 194 aa protein | EZA49383.1 GI: 607354771 |
| odorant receptor 300 [Nasonia vitripennis] 395 aa protein | NP_001177714.1 GI: 299782530 |
| odorant receptor 299 [Nasonia vitripennis] 417 aa protein | NP_001177713.1 GI: 299782528 |
| odorant receptor 298 [Nasonia vitripennis] 403 aa protein | NP_001177712.1 GI: 299782526 |
| odorant receptor 289 [Nasonia vitripennis] 398 aa protein | NP_001177710.1 GI: 299782524 |
| odorant receptor 258 [Nasonia vitripennis] 383 aa protein | NP_001177709.1 GI: 299782520 |
| odorant receptor 241 [Nasonia vitripennis] 384 aa protein | NP_001177708.1 GI: 299782517 |
| odorant receptor 216 [Nasonia vitripennis] 406 aa protein | NP_001177707.1 GI: 299782515 |
| odorant receptor 198 [Nasonia vitripennis] 393 aa protein | NP_001177706.1 GI: 299782513 |
| odorant receptor 190 [Nasonia vitripennis] 396 aa protein | NP_001177705.1 GI: 299782511 |
| odorant receptor 160 [Nasonia vitripennis] 402 aa protein | NP_001177703.1 GI: 299782507 |
| odorant receptor 156 [Nasonia vitripennis] 400 aa protein | NP_001177702.1 GI: 299782503 |
| odorant receptor 149 [Nasonia vitripennis] 389 aa protein | NP_001177700.1 GI: 299782500 |
| odorant receptor 96 [Nasonia vitripennis] 385 aa protein | NP_001177699.1 GI: 299782498 |
| odorant receptor 47 [Nasonia vitripennis] 380 aa protein | NP_001177494.1 GI: 299523279 |
| odorant receptor 46 [Nasonia vitripennis] 377 aa protein | NP_001177493.1 GI: 299523277 |
| odorant receptor 45 [Nasonia vitripennis] 372 aa protein | NP_001177492.1 GI: 299523275 |
| odorant receptor 44 [Nasonia vitripennis] 373 aa protein | NP_001177491.1 GI: 299523273 |
| odorant receptor 43 [Nasonia vitripennis] 382 aa protein | NP_001177490.1 GI: 299523271 |
| odorant receptor 37 [Nasonia vitripennis] 410 aa protein | NP_001177488.1 GI: 299523269 |
| odorant receptor 28 [Nasonia vitripennis] 402 aa protein | NP_001177483.1 GI: 299523261 |
| odorant receptor 27 [Nasonia vitripennis] 419 aa protein | NP_001177482.1 GI: 299523255 |

TABLE 3-continued

Odorant receptors.

| Gene Name | Accession Number |
|---|---|
| odorant receptor 26 [Nasonia vitripennis] 408 aa protein | NP_001177481.1 GI: 299523251 |
| odorant receptor 25 [Nasonia vitripennis] 405 aa protein | NP_001177480.1 GI: 299523248 |
| odorant receptor 24 [Nasonia vitripennis] 415 aa protein | NP_001177479.1 GI: 299523246 |
| odorant receptor 22 [Nasonia vitripennis] 397 aa protein | NP_001177477.1 GI: 299523244 |
| odorant receptor 23 [Nasonia vitripennis] 420 aa protein | NP_001177478.1 GI: 299523242 |
| odorant receptor 20 [Nasonia vitripennis] 407 aa protein | NP_001177475.1 GI: 299523240 |
| odorant receptor 21 [Nasonia vitripennis] 409 aa protein | NP_001177476.1 GI: 299523238 |
| odorant receptor 19 [Nasonia vitripennis] 405 aa protein | NP_001177474.1 GI: 299523236 |
| odorant receptor 17 [Nasonia vitripennis] 409 aa protein | NP_001177473.1 GI: 299523231 |
| odorant receptor 16 [Nasonia vitripennis] 408 aa protein | NP_001177472.1 GI: 299523229 |
| odorant receptor 15 [Nasonia vitripennis] 401 aa protein | NP_001177471.1 GI: 299523226 |
| odorant receptor 13 [Nasonia vitripennis] 431 aa protein | NP_001177469.1 GI: 299523217 |
| odorant receptor 12 [Nasonia vitripennis] 410 aa protein | NP_001177468.1 GI: 299523215 |
| odorant receptor 10 [Nasonia vitripennis] 406 aa protein | NP_001177467.1 GI: 299523212 |
| odorant receptor 9 [Nasonia vitripennis] 405 aa protein | NP_001177435.1 GI: 299523119 |
| odorant receptor 8 [Nasonia vitripennis] 399 aa protein | NP_001177434.1 GI: 299523116 |
| odorant receptor 7 [Nasonia vitripennis] 408 aa protein | NP_001177433.1 GI: 299523113 |
| odorant receptor 6 [Nasonia vitripennis] 399 aa protein | NP_001177432.1 GI: 299523110 |
| odorant receptor 5 [Nasonia vitripennis] 428 aa protein | NP_001177431.1 GI: 299523107 |
| odorant receptor 3 [Nasonia vitripennis] 435 aa protein | NP_001177430.1 GI: 299523104 |
| odorant receptor 2 [Nasonia vitripennis] 420 aa protein | NP_001177429.1 GI: 299523100 |
| odorant receptor 159 [Nasonia vitripennis] 399 aa protein | NP_001177423.1 GI: 299523072 |
| odorant receptor 292 [Nasonia vitripennis] 403 aa protein | NP_001177621.1 GI: 299522969 |
| odorant receptor 291 [Nasonia vitripennis] 402 aa protein | NP_001177620.1 GI: 299522967 |
| odorant receptor 286 [Nasonia vitripennis] 413 aa protein | NP_001177619.1 GI: 299522965 |
| odorant receptor 285 [Nasonia vitripennis] 411 aa protein | NP_001177618.1 GI: 299522963 |
| odorant receptor 281 [Nasonia vitripennis] 401 aa protein | NP_001177617.1 GI: 299522961 |
| odorant receptor 279 [Nasonia vitripennis] 403 aa protein | NP_001177616.1 GI: 299522959 |
| odorant receptor 278 [Nasonia vitripennis] 403 aa protein | NP_001177615.1 GI: 299522957 |
| odorant receptor 277 [Nasonia vitripennis] 404 aa protein | NP_001177614.1 GI: 299522955 |
| odorant receptor 273 [Nasonia vitripennis] 407 aa protein | NP_001177612.1 GI: 299522950 |
| odorant receptor 272 [Nasonia vitripennis] 400 aa protein | NP_001177611.1 GI: 299522948 |
| odorant receptor 271 [Nasonia vitripennis] 400 aa protein | NP_001177610.1 GI: 299522946 |
| odorant receptor 269 [Nasonia vitripennis] 408 aa protein | NP_001177609.1 GI: 299522944 |
| odorant receptor 268 [Nasonia vitripennis] 407 aa protein | NP_001177608.1 GI: 299522942 |
| odorant receptor 267 [Nasonia vitripennis] 407 aa protein | NP_001177607.1 GI: 299522940 |
| odorant receptor 264 [Nasonia vitripennis] 409 aa protein | NP_001177605.1 GI: 299522936 |
| odorant receptor 260 [Nasonia vitripennis] 384 aa protein | NP_001177603.1 GI: 299522932 |
| odorant receptor 257 [Nasonia vitripennis] 383 aa protein | NP_001177602.1 GI: 299522930 |
| odorant receptor 256 [Nasonia vitripennis] 386 aa protein | NP_001177601.1 GI: 299522928 |
| odorant receptor 255 [Nasonia vitripennis] 385 aa protein | NP_001177600.1 GI: 299522926 |
| odorant receptor 251 [Nasonia vitripennis] 386 aa protein | NP_001177598.1 GI: 299522922 |
| odorant receptor 250 [Nasonia vitripennis] 381 aa protein | NP_001177597.1 GI: 299522920 |
| odorant receptor 248 [Nasonia vitripennis] 384 aa protein | NP_001177596.1 GI: 299522918 |
| odorant receptor 247 [Nasonia vitripennis] 381 aa protein | NP_001177595.1 GI: 299522916 |
| odorant receptor 245 [Nasonia vitripennis] 384 aa protein | NP_001177594.1 GI: 299522914 |
| odorant receptor 236 [Nasonia vitripennis] 419 aa protein | NP_001177592.1 GI: 299522910 |
| odorant receptor 233 [Nasonia vitripennis] 397 aa protein | NP_001177591.1 GI: 299522908 |
| odorant receptor 232 [Nasonia vitripennis] 399 aa protein | NP_001177590.1 GI: 299522906 |
| odorant receptor 230 [Nasonia vitripennis] 394 aa protein | NP_001177589.1 GI: 299522904 |
| odorant receptor 229 [Nasonia vitripennis] 398 aa protein | NP_001177588.1 GI: 299522902 |
| odorant receptor 226 [Nasonia vitripennis] 399 aa protein | NP_001177586.1 GI: 299522900 |
| odorant receptor 227 [Nasonia vitripennis] 400 aa protein | NP_001177587.1 GI: 299522898 |
| odorant receptor 224 [Nasonia vitripennis] 398 aa protein | NP_001177584.1 GI: 299522896 |
| odorant receptor 225 [Nasonia vitripennis] 396 aa protein | NP_001177585.1 GI: 299522894 |
| odorant receptor 222 [Nasonia vitripennis] 396 aa protein | NP_001177583.1 GI: 299522892 |
| odorant receptor 219 [Nasonia vitripennis] 396 aa protein | NP_001177581.1 GI: 299522890 |
| odorant receptor 221 [Nasonia vitripennis] 403 aa protein | NP_001177582.1 GI: 299522888 |
| odorant receptor 218 [Nasonia vitripennis] 399 aa protein | NP_001177580.1 GI: 299522886 |
| odorant receptor 217 [Nasonia vitripennis] 412 aa protein | NP_001177579.1 GI: 299522884 |
| odorant receptor 207 [Nasonia vitripennis] 397 aa protein | NP_001177577.1 GI: 299522882 |
| odorant receptor 204 [Nasonia vitripennis] 390 aa protein | NP_001177576.1 GI: 299522880 |
| odorant receptor 203 [Nasonia vitripennis] 388 aa protein | NP_001177575.1 GI: 299522878 |
| odorant receptor 202 [Nasonia vitripennis] 390 aa protein | NP_001177574.1 GI: 299522876 |
| odorant receptor 201 [Nasonia vitripennis] 390 aa protein | NP_001177573.1 GI: 299522874 |
| odorant receptor 196 [Nasonia vitripennis] 398 aa protein | NP_001177572.1 GI: 299522872 |
| odorant receptor 194 [Nasonia vitripennis] 406 aa protein | NP_001177570.1 GI: 299522868 |
| odorant receptor 193 [Nasonia vitripennis] 398 aa protein | NP_001177569.1 GI: 299522866 |
| odorant receptor 192 [Nasonia vitripennis] 398 aa protein | NP_001177568.1 GI: 299522864 |
| odorant receptor 191 [Nasonia vitripennis] 392 aa protein | NP_001177567.1 GI: 299522860 |
| odorant receptor 187 [Nasonia vitripennis] 417 aa protein | NP_001177564.1 GI: 299522856 |
| odorant receptor 179 [Nasonia vitripennis] 402 aa protein | NP_001177560.1 GI: 299522848 |
| odorant receptor 173 [Nasonia vitripennis] 393 aa protein | NP_001177557.1 GI: 299522840 |
| odorant receptor 170 [Nasonia vitripennis] 414 aa protein | NP_001177556.1 GI: 299522836 |
| odorant receptor 167 [Nasonia vitripennis] 404 aa protein | NP_001177555.1 GI: 299522833 |
| odorant receptor 166 [Nasonia vitripennis] 406 aa protein | NP_001177554.1 GI: 299522831 |

TABLE 3-continued

Odorant receptors.

| Gene Name | Accession Number |
|---|---|
| odorant receptor 162 [Nasonia vitripennis] 409 aa protein | NP_001177553.1 GI: 299522829 |
| odorant receptor 161 [Nasonia vitripennis] 393 aa protein | NP_001177552.1 GI: 299522827 |
| odorant receptor 158 [Nasonia vitripennis] 400 aa protein | NP_001177551.1 GI: 299522825 |
| odorant receptor 157 [Nasonia vitripennis] 395 aa protein | NP_001177550.1 GI: 299522823 |
| odorant receptor 151 [Nasonia vitripennis] 391 aa protein | NP_001177549.1 GI: 299522821 |
| odorant receptor 147 [Nasonia vitripennis] 395 aa protein | NP_001177548.1 GI: 299522819 |
| odorant receptor 146 [Nasonia vitripennis] 402 aa protein | NP_001177547.1 GI: 299522817 |
| odorant receptor 143 [Nasonia vitripennis] 391 aa protein | NP_001177545.1 GI: 299522815 |
| odorant receptor 142 [Nasonia vitripennis] 395 aa protein | NP_001177544.1 GI: 299522813 |
| odorant receptor 139 [Nasonia vitripennis] 388 aa protein | NP_001177542.1 GI: 299522809 |
| odorant receptor 137 [Nasonia vitripennis] 388 aa protein | NP_001177541.1 GI: 299522807 |
| odorant receptor 135 [Nasonia vitripennis] 386 aa protein | NP_001177540.1 GI: 299522805 |
| odorant receptor 133 [Nasonia vitripennis] 397 aa protein | NP_001177539.1 GI: 299522803 |
| odorant receptor 132 [Nasonia vitripennis] 395 aa protein | NP_001177538.1 GI: 299522801 |
| odorant receptor 128 [Nasonia vitripennis] 367 aa protein | NP_001177536.1 GI: 299522797 |
| odorant receptor 125 [Nasonia vitripennis] 370 aa protein | NP_001177534.1 GI: 299522793 |
| odorant receptor 124 [Nasonia vitripennis] 370 aa protein | NP_001177533.1 GI: 299522788 |
| odorant receptor 118 [Nasonia vitripennis] 395 aa protein | NP_001177531.1 GI: 299522781 |
| odorant receptor 117 [Nasonia vitripennis] 385 aa protein | NP_001177530.1 GI: 299522779 |
| odorant receptor 115 [Nasonia vitripennis] 414 aa protein | NP_001177529.1 GI: 299522777 |
| odorant receptor 111 [Nasonia vitripennis] 397 aa protein | NP_001177526.1 GI: 299522773 |
| odorant receptor 110 [Nasonia vitripennis] 397 aa protein | NP_001177525.1 GI: 299522769 |
| odorant receptor 107 [Nasonia vitripennis] 393 aa protein | NP_001177524.1 GI: 299522767 |
| odorant receptor 103 [Nasonia vitripennis] 394 aa protein | NP_001177522.1 GI: 299522763 |
| odorant receptor 102 [Nasonia vitripennis] 397 aa protein | NP_001177521.1 GI: 299522761 |
| odorant receptor 100 [Nasonia vitripennis] 396 aa protein | NP_001177519.1 GI: 299522759 |
| odorant receptor 101 [Nasonia vitripennis] 404 aa protein | NP_001177520.1 GI: 299522757 |
| odorant receptor 99 [Nasonia vitripennis] 397 aa protein | NP_001177518.1 GI: 299522754 |
| odorant receptor 94 [Nasonia vitripennis] 387 aa protein | NP_001177517.1 GI: 299522752 |
| odorant receptor 93 [Nasonia vitripennis] 390 aa protein | NP_001177516.1 GI: 299522748 |
| odorant receptor 89 [Nasonia vitripennis] 396 aa protein | NP_001177515.1 GI: 299522746 |
| odorant receptor 88 [Nasonia vitripennis] 391 aa protein | NP_001177514.1 GI: 299522744 |
| odorant receptor 86 [Nasonia vitripennis] 385 aa protein | NP_001177512.1 GI: 299522742 |
| odorant receptor 87 [Nasonia vitripennis] 387 aa protein | NP_001177513.1 GI: 299522740 |
| odorant receptor 79 [Nasonia vitripennis] 413 aa protein | NP_001177511.1 GI: 299522738 |
| odorant receptor 78 [Nasonia vitripennis] 402 aa protein | NP_001177510.1 GI: 299522736 |
| odorant receptor 69 [Nasonia vitripennis] 382 aa protein | NP_001177509.1 GI: 299522734 |
| odorant receptor 68 [Nasonia vitripennis] 372 aa protein | NP_001177508.1 GI: 299522732 |
| odorant receptor 66 [Nasonia vitripennis] 376 aa protein | NP_001177506.1 GI: 299522730 |
| odorant receptor 67 [Nasonia vitripennis] 379 aa protein | NP_001177507.1 GI: 299522728 |
| odorant receptor 65 [Nasonia vitripennis] 379 aa protein | NP_001177505.1 GI: 299522726 |
| odorant receptor 64 [Nasonia vitripennis] 381 aa protein | NP_001177504.1 GI: 299522724 |
| odorant receptor 62 [Nasonia vitripennis] 381 aa protein | NP_001177503.1 GI: 299522722 |
| odorant receptor 61 [Nasonia vitripennis] 402 aa protein | NP_001177502.1 GI: 299522720 |
| odorant receptor 60 [Nasonia vitripennis] 412 aa protein | NP_001177501.1 GI: 299522718 |
| odorant receptor 59 [Nasonia vitripennis] 389 aa protein | NP_001177500.1 GI: 299522716 |
| odorant receptor 51 [Nasonia vitripennis] 377 aa protein | NP_001177497.1 GI: 299522710 |
| odorant receptor 31 [Nasonia vitripennis] 400 aa protein | NP_001177485.1 GI: 299507620 |
| odorant receptor 283 [Nasonia vitripennis] 408 aa protein | NP_001164423.2 GI: 289666787 |
| odorant receptor 77 [Nasonia vitripennis] 413 aa protein | NP_001164671.1 GI: 283945552 |
| odorant receptor 76 [Nasonia vitripennis] 417 aa protein | NP_001164670.1 GI: 283945550 |
| odorant receptor 263 [Nasonia vitripennis] 384 aa protein | NP_001164420.2 GI: 283945546 |
| odorant receptor 301 [Nasonia vitripennis] 422 aa protein | NP_001164659.1 GI: 283945514 |
| odorant receptor 1 [Nasonia vitripennis] 475 aa protein | NP_001164465.1 GI: 283436213 |
| odorant receptor 253 [Nasonia vitripennis] 383 aa protein | NP_001164463.1 GI: 283436209 |
| odorant receptor 293 [Nasonia vitripennis] 371 aa protein | NP_001164462.1 GI: 283436207 |
| odorant receptor 98 [Nasonia vitripennis] 395 aa protein | NP_001164458.1 GI: 283436197 |
| odorant receptor 265 [Nasonia vitripennis] 408 aa protein | NP_001164457.1 GI: 283436195 |
| odorant receptor 280 [Nasonia vitripennis] 407 aa protein | NP_001164422.1 GI: 283436107 |
| odorant receptor 243 [Nasonia vitripennis] 382 aa protein | NP_001164417.1 GI: 283436101 |
| odorant receptor 249 [Nasonia vitripennis] 388 aa protein | NP_001164419.1 GI: 283436099 |
| odorant receptor 246 [Nasonia vitripennis] 382 aa protein | NP_001164418.1 GI: 283436097 |
| odorant receptor 168 [Nasonia vitripennis] 401 aa protein | NP_001164416.1 GI: 283436095 |
| odorant receptor 163 [Nasonia vitripennis] 409 aa protein | NP_001164411.1 GI: 283135180 |
| odorant receptor 154 [Nasonia vitripennis] 395 aa protein | NP_001164405.1 GI: 283135167 |
| odorant receptor 141 [Nasonia vitripennis] 392 aa protein | NP_001164404.1 GI: 283135164 |
| odorant receptor 105 [Nasonia vitripennis] 396 aa protein | NP_001164401.1 GI: 283135159 |
| odorant receptor 92 [Nasonia vitripennis] 391 aa protein | NP_001164399.1 GI: 283135153 |
| odorant receptor 85 [Nasonia vitripennis] 392 aa protein | NP_001164398.1 GI: 283135151 |
| odorant receptor 80 [Nasonia vitripennis] 386 aa protein | NP_001164396.1 GI: 283135146 |
| odorant receptor 82 [Nasonia vitripennis] 392 aa protein | NP_001164395.1 GI: 283135140 |
| odorant receptor 81 [Nasonia vitripennis] 387 aa protein | NP_001164394.1 GI: 283135138 |
| odorant receptor 2 [Apis mellifera] 477 aa protein | NP_001128415.1 GI: 201023349 |
| odorant receptor 180 [Nasonia vitripennis] 395 aa protein | NP_001177704.1 GI: 299782509 |
| odorant receptor 276 [Nasonia vitripennis] 403 aa protein | NP_001177613.1 GI: 299522952 |
| odorant receptor 182 [Nasonia vitripennis] 411 aa protein | NP_001177562.1 GI: 299522852 |

TABLE 3-continued

Odorant receptors.

| Gene Name | Accession Number |
|---|---|
| odorant receptor 46a, isoform A-like [Diachasma alloeum] 654 aa protein | XP_015127274.1 GI: 970885192 |
| odorant receptor 130 [Nasonia vitripennis] 395 aa protein | NP_001177640.2 GI: 299782532 |
| odorant receptor 33b-like [Bactrocera oleae] 712 aa protein | XP_014097126.1 GI: 929374155 |
| odorant receptor coreceptor [Ceratitis capitata] 473 aa protein | NP_001266301.1 GI: 525342887 |
| odorant receptor 296 [Nasonia vitripennis] 387 aa protein | NP_001177711.1 GI: 299782522 |
| odorant receptor 153 [Nasonia vitripennis] 389 aa protein | NP_001177701.1 GI: 299782505 |
| odorant receptor 71 [Nasonia vitripennis] 384 aa protein | NP_001177698.1 GI: 299782496 |
| odorant receptor 288 [Nasonia vitripennis] 399 aa protein | NP_001177643.1 GI: 299528645 |
| odorant receptor 58 [Nasonia vitripennis] 393 aa protein | NP_001177639.1 GI: 299528533 |
| odorant receptor 36 [Nasonia vitripennis] 404 aa protein | NP_001177487.1 GI: 299523266 |
| odorant receptor 35 [Nasonia vitripennis] 422 aa protein | NP_001177486.1 GI: 299523264 |
| odorant receptor 14 [Nasonia vitripennis] 405 aa protein | NP_001177470.1 GI: 299523221 |
| odorant receptor 145 [Nasonia vitripennis] 401 aa protein | NP_001177546.1 GI: 299523210 |
| odorant receptor 294 [Nasonia vitripennis] 354 aa protein | NP_001177622.1 GI: 299522971 |
| odorant receptor 266 [Nasonia vitripennis] 407 aa protein | NP_001177606.1 GI: 299522938 |
| odorant receptor 252 [Nasonia vitripennis] 386 aa protein | NP_001177599.1 GI: 299522924 |
| odorant receptor 242 [Nasonia vitripennis] 385 aa protein | NP_001177593.1 GI: 299522912 |
| odorant receptor 195 [Nasonia vitripennis] 400 aa protein | NP_001177571.1 GI: 299522870 |
| odorant receptor 181 [Nasonia vitripennis] 405 aa protein | NP_001177561.1 GI: 299522850 |
| odorant receptor 140 [Nasonia vitripennis] 393 aa protein | NP_001177543.1 GI: 299522811 |
| odorant receptor 129 [Nasonia vitripennis] 395 aa protein | NP_001177537.1 GI: 299522799 |
| odorant receptor 126 [Nasonia vitripennis] 369 aa protein | NP_001177535.1 GI: 299522795 |
| odorant receptor 114 [Nasonia vitripennis] 409 aa protein | NP_001177528.1 GI: 299522775 |
| odorant receptor 113 [Nasonia vitripennis] 393 aa protein | NP_001177527.1 GI: 299522771 |
| odorant receptor 106 [Nasonia vitripennis] 397 aa protein | NP_001177523.1 GI: 299522765 |
| odorant receptor 53 [Nasonia vitripennis] 384 aa protein | NP_001177498.1 GI: 299522712 |
| odorant receptor 262 [Nasonia vitripennis] 385 aa protein | NP_001164460.2 GI: 283945544 |
| odorant receptor 122 [Nasonia vitripennis] 369 aa protein | NP_001164459.1 GI: 283436199 |
| odorant receptor 275 [Nasonia vitripennis] 405 aa protein | NP_001164421.1 GI: 283436105 |
| odorant receptor 41 [Nasonia vitripennis] 397 aa protein | NP_001164391.1 GI: 283135132 |
| odorant receptor 295 [Nasonia vitripennis] 370 aa protein | NP_001177623.1 GI: 299522975 |
| odorant receptor 188 [Nasonia vitripennis] 395 aa protein | NP_001177565.1 GI: 299522858 |
| odorant receptor 175 [Nasonia vitripennis] 393 aa protein | NP_001177558.1 GI: 299522844 |
| odorant receptor 56 [Nasonia vitripennis] 371 aa protein | NP_001177499.1 GI: 299522714 |
| odorant receptor 48 [Nasonia vitripennis] 395 aa protein | NP_001177495.1 GI: 299522708 |
| odorant receptor 38 [Nasonia vitripennis] 414 aa protein | NP_001177489.1 GI: 299528647 |
| odorant receptor 29 [Nasonia vitripennis] 403 aa protein | NP_001177484.1 GI: 299523259 |
| odorant receptor 261 [Nasonia vitripennis] 381 aa protein | NP_001177604.1 GI: 299522934 |
| odorant receptor 189 [Nasonia vitripennis] 395 aa protein | NP_001177566.1 GI: 299522862 |
| odorant receptor 183 [Nasonia vitripennis] 405 aa protein | NP_001177563.1 GI: 299522854 |
| odorant receptor 177 [Nasonia vitripennis] 392 aa protein | NP_001177559.1 GI: 299522846 |
| odorant receptor 119 [Nasonia vitripennis] 391 aa protein | NP_001177532.1 GI: 299522786 |
| odorant receptor 134 [Nasonia vitripennis] 395 aa protein | NP_001177696.1 GI: 299782491 |
| odorant receptor 72 [Nasonia vitripennis] 383 aa protein | NP_001177641.1 GI: 299528641 |
| odorant receptor coreceptor-like [Diuraphis noxia] 167 aa protein | XP_015371514.1 GI: 985412051 |
| odorant receptor 46a, isoform B-like [Diuraphis noxia] 251 aa protein | XP_015367780.1 GI: 985400241 |
| odorant receptor 46a, isoform B-like [Diuraphis noxia] 129 aa protein | XP_015367779.1 GI: 985400239 |
| odorant receptor 22c-like [Diuraphis noxia] 176 aa protein | XP_015367764.1 GI: 985400213 |
| odorant receptor 85b-like [Diuraphis noxia] 219 aa protein | XP_015379800.1 GI: 985390295 |
| odorant receptor coreceptor [Diachasma alloeum] 478 aa protein | XP_015126208.1 GI: 970919070 |
| odorant receptor 46a, isoform B-like [Diachasma alloeum] 391 aa protein | XP_015126084.1 GI: 970918843 |
| putative odorant receptor 65b [Diachasma alloeum] 342 aa protein | XP_015125987.1 GI: 970918672 |
| odorant receptor 13a-like [Diachasma alloeum] 417 aa protein | XP_015125770.1 GI: 970918327 |
| odorant receptor 30a-like [Diachasma alloeum] 160 aa protein | XP_015125618.1 GI: 970918086 |
| odorant receptor 30a-like [Diachasma alloeum] 125 aa protein | XP_015125102.1 GI: 970917269 |
| odorant receptor 30a-like [Diachasma alloeum] 125 aa protein | XP_015125054.1 GI: 970917185 |
| odorant receptor 13a-like [Diachasma alloeum] 395 aa protein | XP_015125011.1 GI: 970917102 |
| odorant receptor 13a-like [Diachasma alloeum] 411 aa protein | XP_015125010.1 GI: 970917100 |
| odorant receptor 13a-like [Diachasma alloeum] 412 aa protein | XP_015125009.1 GI: 970917098 |
| odorant receptor 22c-like [Diachasma alloeum] 417 aa protein | XP_015124997.1 GI: 970917076 |
| odorant receptor 4-like [Diachasma alloeum] 396 aa protein | XP_015124996.1 GI: 970917074 |
| odorant receptor 4-like [Diachasma alloeum] 191 aa protein | XP_015124994.1 GI: 970917070 |
| odorant receptor 22c-like [Diachasma alloeum] 398 aa protein | XP_015124993.1 GI: 970917068 |
| odorant receptor 67c-like isoform X3 [Diachasma alloeum] 350 aa protein | XP_015123023.1 GI: 970913425 |
| odorant receptor 13a-like isoform X1 [Diachasma alloeum] 386 aa protein | XP_015123021.1 GI: 970913421 |
| odorant receptor 46a, isoform A-like [Diachasma alloeum] 386 aa protein | XP_015122891.1 GI: 970913183 |
| odorant receptor Or1-like [Diachasma alloeum] 401 aa protein | XP_015122890.1 GI: 970913181 |
| odorant receptor 13a-like [Diachasma alloeum] 385 aa protein | XP_015122297.1 GI: 970912091 |

TABLE 3-continued

Odorant receptors.

| Gene Name | Accession Number |
| --- | --- |
| odorant receptor coreceptor-like [Diachasma alloeum] 160 aa protein | XP_015122295.1 GI: 970912087 |
| odorant receptor 82a-like [Diachasma alloeum] 281 aa protein | XP_015122294.1 GI: 970912085 |
| odorant receptor 13a-like [Diachasma alloeum] 398 aa protein | XP_015122293.1 GI: 970912083 |
| odorant receptor 67c-like [Diachasma alloeum] 225 aa protein | XP_015122289.1 GI: 970912076 |
| odorant receptor 4-like isoform X2 [Diachasma alloeum] 384 aa protein | XP_015122288.1 GI: 970912074 |
| odorant receptor 4-like isoform X1 [Diachasma alloeum] 390 aa protein | XP_015122287.1 GI: 970912072 |
| odorant receptor 4-like isoform X1 [Diachasma alloeum] 390 aa protein | XP_015122286.1 GI: 970912070 |
| odorant receptor 67c-like [Diachasma alloeum] 389 aa protein | XP_015122278.1 GI: 970912056 |
| odorant receptor 4 [Diachasma alloeum] 102 aa protein | XP_015122277.1 GI: 970912054 |
| odorant receptor 82a-like, partial [Diachasma alloeum] 274 aa protein | XP_015122272.1 GI: 970912046 |
| odorant receptor 4-like [Diachasma alloeum] 378 aa protein | XP_015121583.1 GI: 970910790 |
| odorant receptor 13a-like [Diachasma alloeum] 431 aa protein | XP_015121344.1 GI: 970910338 |
| odorant receptor 13a-like [Diachasma alloeum] 458 aa protein | XP_015121343.1 GI: 970910336 |
| odorant receptor Or2-like [Diachasma alloeum] 413 aa protein | XP_015120978.1 GI: 970909674 |
| odorant receptor 82a-like [Diachasma alloeum] 116 aa protein | XP_015120698.1 GI: 970909157 |
| odorant receptor 13a-like [Diachasma alloeum] 122 aa protein | XP_015120696.1 GI: 970909155 |
| odorant receptor 46a, isoform A-like [Diachasma alloeum] 391 aa protein | XP_015120217.1 GI: 970908285 |
| odorant receptor Or1-like, partial [Diachasma alloeum] 360 aa protein | XP_015119834.1 GI: 970907577 |
| odorant receptor Or2-like [Diachasma alloeum] 193 aa protein | XP_015119359.1 GI: 970906702 |
| odorant receptor 67b-like [Diachasma alloeum] 169 aa protein | XP_015118342.1 GI: 970904876 |
| odorant receptor 22c-like [Diachasma alloeum] 431 aa protein | XP_015118336.1 GI: 970904864 |
| putative odorant receptor 71a [Diachasma alloeum] 302 aa protein | XP_015118334.1 GI: 970904862 |
| odorant receptor 2a-like [Diachasma alloeum] 419 aa protein | XP_015117540.1 GI: 970903392 |
| odorant receptor Or2-like [Diachasma alloeum] 202 aa protein | XP_015117539.1 GI: 970903390 |
| odorant receptor 85f-like [Diachasma alloeum] 392 aa protein | XP_015117537.1 GI: 970903386 |
| putative odorant receptor 85d [Diachasma alloeum] 402 aa protein | XP_015117136.1 GI: 970902641 |
| odorant receptor 22c-like [Diachasma alloeum] 402 aa protein | XP_015117110.1 GI: 970902593 |
| odorant receptor 22c-like [Diachasma alloeum] 266 aa protein | XP_015116846.1 GI: 970902114 |
| odorant receptor 49b-like [Diachasma alloeum] 279 aa protein | XP_015116845.1 GI: 970902112 |
| odorant receptor 13a-like isoform X2 [Diachasma alloeum] 321 aa protein | XP_015115896.1 GI: 970900372 |
| odorant receptor 13a-like isoform X1 [Diachasma alloeum] 325 aa protein | XP_015115895.1 GI: 970900370 |
| odorant receptor 13a-like [Diachasma alloeum] 386 aa protein | XP_015115894.1 GI: 970900368 |
| odorant receptor 46a, isoform B-like [Diachasma alloeum] 399 aa protein | XP_015115875.1 GI: 970900334 |
| odorant receptor 33a-like [Diachasma alloeum] 343 aa protein | XP_015115812.1 GI: 970900224 |
| odorant receptor 13a-like [Diachasma alloeum] 380 aa protein | XP_015115810.1 GI: 970900220 |
| odorant receptor Or1-like [Diachasma alloeum] 390 aa protein | XP_015115473.1 GI: 970899618 |
| odorant receptor 49b-like [Diachasma alloeum] 386 aa protein | XP_015114827.1 GI: 970898436 |
| putative odorant receptor 98b [Diachasma alloeum] 367 aa protein | XP_015114784.1 GI: 970898359 |
| odorant receptor 85b [Diachasma alloeum] 393 aa protein | XP_015114365.1 GI: 970897598 |
| odorant receptor 63a-like [Diachasma alloeum] 383 aa protein | XP_015114103.1 GI: 970897122 |
| odorant receptor 67c-like [Diachasma alloeum] 116 aa protein | XP_015114099.1 GI: 970897116 |
| odorant receptor 82a-like [Diachasma alloeum] 388 aa protein | XP_015114079.1 GI: 970897076 |
| odorant receptor Or2-like [Diachasma alloeum] 379 aa protein | XP_015114021.1 GI: 970896976 |
| odorant receptor Or2-like [Diachasma alloeum] 379 aa protein | XP_015114020.1 GI: 970896974 |
| odorant receptor 82a-like [Diachasma alloeum] 325 aa protein | XP_015112771.1 GI: 970894647 |
| putative odorant receptor 92a [Diachasma alloeum] 152 aa protein | XP_015112770.1 GI: 970894645 |
| odorant receptor 13a-like [Diachasma alloeum] 403 aa protein | XP_015112769.1 GI: 970894643 |
| odorant receptor 82a-like [Diachasma alloeum] 403 aa protein | XP_015112590.1 GI: 970894312 |
| odorant receptor 82a-like [Diachasma alloeum] 403 aa protein | XP_015112589.1 GI: 970894310 |
| odorant receptor 4-like [Diachasma alloeum] 409 aa protein | XP_015112587.1 GI: 970894308 |
| odorant receptor 85c-like [Diachasma alloeum] 411 aa protein | XP_015112586.1 GI: 970894306 |
| odorant receptor 82a-like [Diachasma alloeum] 412 aa protein | XP_015112585.1 GI: 970894304 |
| odorant receptor 67c-like [Diachasma alloeum] 411 aa protein | XP_015112584.1 GI: 970894302 |
| odorant receptor Or2-like [Diachasma alloeum] 415 aa protein | XP_015112582.1 GI: 970894300 |
| odorant receptor 13a-like [Diachasma alloeum] 365 aa protein | XP_015111780.1 GI: 970892852 |
| odorant receptor 13a-like [Diachasma alloeum] 407 aa protein | XP_015111777.1 GI: 970892846 |
| odorant receptor 13a-like [Diachasma alloeum] 163 aa protein | XP_015111079.1 GI: 970891543 |
| odorant receptor 42b-like [Diachasma alloeum] 134 aa protein | XP_015111029.1 GI: 970891451 |
| odorant receptor 59b-like [Diachasma alloeum] 420 aa protein | XP_015110864.1 GI: 970891147 |
| odorant receptor 33c-like [Diachasma alloeum] 428 aa protein | XP_015110846.1 GI: 970891111 |
| odorant receptor 47b-like [Diachasma alloeum] 424 aa protein | XP_015110804.1 GI: 970891036 |
| odorant receptor 33b-like [Diachasma alloeum] 415 aa protein | XP_015110803.1 GI: 970891034 |
| odorant receptor coreceptor-like [Diachasma alloeum] 430 aa protein | XP_015110802.1 GI: 970891032 |

TABLE 3-continued

Odorant receptors.

| Gene Name | Accession Number |
|---|---|
| odorant receptor 33b-like [Diachasma alloeum] 435 aa protein | XP_015110787.1 GI: 970891004 |
| odorant receptor 46a, isoform A-like isoform X2 [Diachasma alloeum] 358 aa protein | XP_015110556.1 GI: 970890577 |
| putative odorant receptor 85d isoform X1 [Diachasma alloeum] 395 aa protein | XP_015110555.1 GI: 970890575 |
| putative odorant receptor 92a [Diachasma alloeum] 249 aa protein | XP_015110532.1 GI: 970890535 |
| odorant receptor 13a-like [Diachasma alloeum] 389 aa protein | XP_015110383.1 GI: 970890261 |
| odorant receptor 4-like [Diachasma alloeum] 231 aa protein | XP_015110343.1 GI: 970890187 |
| odorant receptor 10a-like [Diachasma alloeum] 268 aa protein | XP_015109340.1 GI: 970888368 |
| odorant receptor 4-like [Diachasma alloeum] 278 aa protein | XP_015108894.1 GI: 970887560 |
| odorant receptor 10a-like [Diachasma alloeum] 388 aa protein | XP_015108891.1 GI: 970887554 |
| odorant receptor 4-like [Diachasma alloeum] 126 aa protein | XP_015108890.1 GI: 970887552 |
| odorant receptor 67c-like [Diachasma alloeum] 381 aa protein | XP_015108889.1 GI: 970887550 |
| putative odorant receptor 85e [Diachasma alloeum] 422 aa protein | XP_015108502.1 GI: 970886846 |
| odorant receptor Or1-like isoform X3 [Diachasma alloeum] 425 aa protein | XP_015127537.1 GI: 970885664 |
| odorant receptor Or1-like isoform X2 [Diachasma alloeum] 450 aa protein | XP_015127536.1 GI: 970885662 |
| odorant receptor Or1-like isoform X1 [Diachasma alloeum] 460 aa protein | XP_015127535.1 GI: 970885660 |
| odorant receptor Or1-like [Diachasma alloeum] 350 aa protein | XP_015127275.1 GI: 970885194 |
| odorant receptor 46a, isoform A-like [Diachasma alloeum] 391 aa protein | XP_015127273.1 GI: 970885190 |
| odorant receptor Or2-like [Diachasma alloeum] 416 aa protein | XP_015127033.1 GI: 970884759 |
| odorant receptor 22c-like [Diachasma alloeum] 182 aa protein | XP_015127018.1 GI: 970884735 |
| odorant receptor 49b-like [Diachasma alloeum] 157 aa protein | XP_015127017.1 GI: 970884733 |
| odorant receptor 4-like [Diachasma alloeum] 259 aa protein | XP_015126452.1 GI: 970883704 |
| putative odorant receptor 71a [Diachasma alloeum] 334 aa protein | XP_015126451.1 GI: 970883702 |
| odorant receptor 67a-like [Diachasma alloeum] 316 aa protein | XP_015124669.1 GI: 970883032 |
| odorant receptor 43a-like [Diachasma alloeum] 185 aa protein | XP_015124656.1 GI: 970883030 |
| odorant receptor 4-like [Diachasma alloeum] 388 aa protein | XP_015117493.1 GI: 970881492 |
| odorant receptor 67c-like [Diachasma alloeum] 343 aa protein | XP_015117460.1 GI: 970881486 |
| odorant receptor 13a-like isoform X2 [Diachasma alloeum] 400 aa protein | XP_015117447.1 GI: 970881484 |
| odorant receptor 13a-like [Diachasma alloeum] 401 aa protein | XP_015117410.1 GI: 970881478 |
| odorant receptor coreceptor-like [Diachasma alloeum] 263 aa protein | XP_015116354.1 GI: 970881285 |
| odorant receptor 47a-like [Diachasma alloeum] 204 aa protein | XP_015116327.1 GI: 970881281 |
| putative odorant receptor 98b [Diachasma alloeum] 390 aa protein | XP_015116314.1 GI: 970881279 |
| odorant receptor 4-like [Diachasma alloeum] 338 aa protein | XP_015115419.1 GI: 970881109 |
| odorant receptor Or2-like [Diachasma alloeum] 454 aa protein | XP_015112971.1 GI: 970880651 |
| odorant receptor Or2-like [Diachasma alloeum] 385 aa protein | XP_015112944.1 GI: 970880647 |
| odorant receptor 49b-like [Diachasma alloeum] 427 aa protein | XP_015112917.1 GI: 970880643 |
| odorant receptor 49b-like [Diachasma alloeum] 381 aa protein | XP_015112905.1 GI: 970880641 |
| odorant receptor 13a-like [Plutella xylostella] 424 aa protein | NP_001292415.1 GI: 770075498 |
| odorant receptor 24a-like, partial [Halyomorpha halys] 99 aa protein | XP_014293293.1 GI: 939698236 |
| odorant receptor 59b-like [Halyomorpha halys] 417 aa protein | XP_014293234.1 GI: 939698126 |
| odorant receptor 85b-like [Halyomorpha halys] 399 aa protein | XP_014292083.1 GI: 939695930 |
| odorant receptor 22c-like [Halyomorpha halys] 411 aa protein | XP_014292012.1 GI: 939695795 |
| putative odorant receptor 71a, partial [Halyomorpha halys] 240 aa protein | XP_014291481.1 GI: 939694804 |
| odorant receptor 24a-like [Halyomorpha halys] 127 aa protein | XP_014290811.1 GI: 939693500 |
| odorant receptor 85b-like [Halyomorpha halys] 83 aa protein | XP_014290807.1 GI: 939693494 |
| odorant receptor 85b-like [Halyomorpha halys] 204 aa protein | XP_014290806.1 GI: 939693492 |
| odorant receptor 22c-like [Halyomorpha halys] 420 aa protein | XP_014290805.1 GI: 939693490 |
| odorant receptor 4-like [Halyomorpha halys] 420 aa protein | XP_014290804.1 GI: 939693488 |
| odorant receptor 4-like [Halyomorpha halys] 208 aa protein | XP_014290613.1 GI: 939693125 |
| odorant receptor 43a-like [Halyomorpha halys] 152 aa protein | XP_014290611.1 GI: 939693123 |
| odorant receptor 4-like [Halyomorpha halys] 366 aa protein | XP_014290317.1 GI: 939692579 |
| odorant receptor 49a-like [Halyomorpha halys] 387 aa protein | XP_014289672.1 GI: 939691321 |
| odorant receptor 24a-like [Halyomorpha halys] 419 aa protein | XP_014289234.1 GI: 939690515 |
| odorant receptor 82a-like [Halyomorpha halys] 391 aa protein | XP_014289202.1 GI: 939690459 |
| odorant receptor 82a-like [Halyomorpha halys] 391 aa protein | XP_014289201.1 GI: 939690457 |
| odorant receptor 82a-like [Halyomorpha halys] 391 aa protein | XP_014289200.1 GI: 939690455 |
| odorant receptor 43a-like [Halyomorpha halys] 319 aa protein | XP_014289020.1 GI: 939690118 |
| odorant receptor 67c-like isoform X3 [Halyomorpha halys] 156 aa protein | XP_014288707.1 GI: 939689526 |
| odorant receptor 67c-like isoform X2 [Halyomorpha halys] 319 aa protein | XP_014288705.1 GI: 939689524 |
| odorant receptor 67c-like isoform X1 [Halyomorpha halys] 349 aa protein | XP_014288704.1 GI: 939689522 |
| odorant receptor 24a [Halyomorpha halys] 414 aa protein | XP_014288393.1 GI: 939688944 |
| odorant receptor 24a [Halyomorpha halys] 414 aa protein | XP_014288391.1 GI: 939688942 |
| odorant receptor 4-like [Halyomorpha halys] 378 aa protein | XP_014287492.1 GI: 939686767 |
| putative odorant receptor 71a [Halyomorpha halys] 140 aa protein | XP_014287487.1 GI: 939686757 |

TABLE 3-continued

Odorant receptors.

| Gene Name | Accession Number |
|---|---|
| odorant receptor 85b-like [Halyomorpha halys] 389 aa protein | XP_014287367.1 GI: 939686386 |
| odorant receptor 43b-like [Halyomorpha halys] 389 aa protein | XP_014287042.1 GI: 939685352 |
| odorant receptor 4-like [Halyomorpha halys] 389 aa protein | XP_014287040.1 GI: 939685346 |
| putative odorant receptor 92a [Halyomorpha halys] 373 aa protein | XP_014286385.1 GI: 939683385 |
| odorant receptor coreceptor-like [Halyomorpha halys] 133 aa protein | XP_014285169.1 GI: 939679600 |
| odorant receptor 4-like [Halyomorpha halys] 349 aa protein | XP_014282544.1 GI: 939671925 |
| putative odorant receptor 85d isoform X1 [Halyomorpha halys] 270 aa protein | XP_014282484.1 GI: 939671750 |
| odorant receptor 49a-like isoform X1 [Halyomorpha halys] 175 aa protein | XP_014282386.1 GI: 939671478 |
| odorant receptor 33a-like [Halyomorpha halys] 406 aa protein | XP_014281821.1 GI: 939670017 |
| odorant receptor coreceptor isoform X2 [Halyomorpha halys] 474 aa protein | XP_014279420.1 GI: 939663702 |
| odorant receptor coreceptor isoform X1 [Halyomorpha halys] 474 aa protein | XP_014279419.1 GI: 939663700 |
| odorant receptor 33a-like [Halyomorpha halys] 247 aa protein | XP_014278712.1 GI: 939661914 |
| odorant receptor 67c-like [Halyomorpha halys] 417 aa protein | XP_014278702.1 GI: 939661887 |
| odorant receptor 22c-like [Halyomorpha halys] 426 aa protein | XP_014276985.1 GI: 939657423 |
| odorant receptor 4-like [Halyomorpha halys] 284 aa protein | XP_014276746.1 GI: 939656832 |
| odorant receptor 94a-like [Halyomorpha halys] 339 aa protein | XP_014276741.1 GI: 939656820 |
| odorant receptor 22c-like [Halyomorpha halys] 400 aa protein | XP_014275988.1 GI: 939654773 |
| odorant receptor 24a-like [Halyomorpha halys] 412 aa protein | XP_014275211.1 GI: 939652560 |
| odorant receptor 30a-like [Halyomorpha halys] 389 aa protein | XP_014274900.1 GI: 939651712 |
| odorant receptor 47a-like [Halyomorpha halys] 427 aa protein | XP_014274444.1 GI: 939650476 |
| odorant receptor 67c-like [Halyomorpha halys] 154 aa protein | XP_014272634.1 GI: 939645252 |
| odorant receptor 83a-like [Halyomorpha halys] 416 aa protein | XP_014271039.1 GI: 939640611 |
| odorant receptor 4-like isoform X3 [Halyomorpha halys] 354 aa protein | XP_014270190.1 GI: 939638174 |
| odorant receptor 4-like isoform X2 [Halyomorpha halys] 376 aa protein | XP_014270189.1 GI: 939638171 |
| odorant receptor 4-like isoform X1 [Halyomorpha halys] 408 aa protein | XP_014270188.1 GI: 939638168 |
| odorant receptor 24a-like [Halyomorpha halys] 414 aa protein | XP_014270184.1 GI: 939638154 |
| odorant receptor 24a-like [Halyomorpha halys] 81 aa protein | XP_014294800.1 GI: 939638065 |
| odorant receptor 24a-like [Halyomorpha halys] 134 aa protein | XP_014294799.1 GI: 939638061 |
| odorant receptor 85b-like [Halyomorpha halys] 99 aa protein | XP_014294798.1 GI: 939638059 |
| odorant receptor 24a-like [Halyomorpha halys] 415 aa protein | XP_014294793.1 GI: 939638051 |
| odorant receptor 30a-like [Halyomorpha halys] 415 aa protein | XP_014294791.1 GI: 939638047 |
| odorant receptor 7a-like [Halyomorpha halys] 124 aa protein | XP_014294788.1 GI: 939638038 |
| odorant receptor 24a-like [Halyomorpha halys] 415 aa protein | XP_014294787.1 GI: 939638035 |
| odorant receptor 9a-like [Halyomorpha halys] 382 aa protein | XP_014294442.1 GI: 939637038 |
| odorant receptor Or1-like isoform X1 [Halyomorpha halys] 384 aa protein | XP_014294439.1 GI: 939637034 |
| odorant receptor 85b-like isoform X1 [Halyomorpha halys] 389 aa protein | XP_014293859.1 GI: 939635389 |
| odorant receptor 46a, isoform B-like [Halyomorpha halys] 390 aa protein | XP_014291074.1 GI: 939634209 |
| odorant receptor 49b-like [Halyomorpha halys] 288 aa protein | XP_014281510.1 GI: 939631411 |
| odorant receptor 4-like [Halyomorpha halys] 397 aa protein | XP_014281005.1 GI: 939631291 |
| odorant receptor 85c-like [Halyomorpha halys] 99 aa protein | XP_014280802.1 GI: 939631237 |
| odorant receptor 85b-like [Halyomorpha halys] 99 aa protein | XP_014280790.1 GI: 939631235 |
| odorant receptor 24a-like isoform X1 [Halyomorpha halys] 397 aa protein | XP_014280768.1 GI: 939631231 |
| odorant receptor 7a-like [Halyomorpha halys] 310 aa protein | XP_014280756.1 GI: 939631229 |
| odorant receptor 4-like [Halyomorpha halys] 413 aa protein | XP_014280744.1 GI: 939631227 |
| odorant receptor 82a-like [Halyomorpha halys] 411 aa protein | XP_014280723.1 GI: 939631221 |
| odorant receptor 82a [Halyomorpha halys] 419 aa protein | XP_014280696.1 GI: 939631215 |
| odorant receptor 24a-like [Halyomorpha halys] 417 aa protein | XP_014280623.1 GI: 939631200 |
| odorant receptor 24a-like [Halyomorpha halys] 431 aa protein | XP_014280612.1 GI: 939631197 |
| odorant receptor 49b-like [Halyomorpha halys] 393 aa protein | XP_014275003.1 GI: 939629564 |
| odorant receptor 7a-like [Halyomorpha halys] 123 aa protein | XP_014273506.1 GI: 939629170 |
| odorant receptor 85b-like [Halyomorpha halys] 388 aa protein | XP_014273330.1 GI: 939629125 |
| odorant receptor 85b-like [Halyomorpha halys] 386 aa protein | XP_014272535.1 GI: 939628833 |
| odorant receptor 24a-like [Halyomorpha halys] 409 aa protein | XP_014272447.1 GI: 939628818 |
| odorant receptor 4-like [Halyomorpha halys] 410 aa protein | XP_014294765.1 GI: 939628125 |
| odorant receptor 43b-like [Bactrocera oleae] 255 aa protein | XP_014101582.1 GI: 929382187 |
| odorant receptor 43b-like, partial [Bactrocera oleae] 256 aa protein | XP_014101520.1 GI: 929382078 |
| odorant receptor 88a-like, partial [Bactrocera oleae] 400 aa protein | XP_014101401.1 GI: 929381869 |
| odorant receptor 85c-like, partial [Bactrocera oleae] 277 aa protein | XP_014101291.1 GI: 929381677 |
| odorant receptor 67c-like [Bactrocera oleae] 405 aa protein | XP_014101001.1 GI: 929381148 |
| odorant receptor 43b-like, partial [Bactrocera oleae] 210 aa protein | XP_014100962.1 GI: 929381076 |
| odorant receptor 7a-like [Bactrocera oleae] 471 aa protein | XP_014100884.1 GI: 929380937 |
| odorant receptor 7a-like, partial [Bactrocera oleae] 398 aa protein | XP_014100883.1 GI: 929380935 |
| odorant receptor 59a-like [Bactrocera oleae] 249 aa protein | XP_014100068.1 GI: 929379483 |
| odorant receptor 30a-like [Bactrocera oleae] 403 aa protein | XP_014100035.1 GI: 929379425 |

TABLE 3-continued

Odorant receptors.

| Gene Name | Accession Number |
| --- | --- |
| odorant receptor 88a-like [Bactrocera oleae] 410 aa protein | XP_014099351.1 GI: 929378168 |
| odorant receptor 88a-like [Bactrocera oleae] 404 aa protein | XP_014099350.1 GI: 929378166 |
| odorant receptor 42b-like [Bactrocera oleae] 256 aa protein | XP_014098809.1 GI: 929377189 |
| odorant receptor 63a-like [Bactrocera oleae] 415 aa protein | XP_014098250.1 GI: 929376191 |
| odorant receptor 45a-like [Bactrocera oleae] 365 aa protein | XP_014098074.1 GI: 929375879 |
| odorant receptor 45a-like, partial [Bactrocera oleae] 196 aa protein | XP_014098072.1 GI: 929375875 |
| odorant receptor 45a-like [Bactrocera oleae] 334 aa protein | XP_014098071.1 GI: 929375873 |
| odorant receptor 1a-like [Bactrocera oleae] 388 aa protein | XP_014098069.1 GI: 929375871 |
| odorant receptor 67d-like [Bactrocera oleae] 168 aa protein | XP_014097995.1 GI: 929375735 |
| odorant receptor Or2-like [Bactrocera oleae] 375 aa protein | XP_014097486.1 GI: 929374815 |
| odorant receptor Or2-like [Bactrocera oleae] 331 aa protein | XP_014097484.1 GI: 929374811 |
| odorant receptor 33b-like [Bactrocera oleae] 384 aa protein | XP_014097127.1 GI: 929374157 |
| odorant receptor 63a-like [Bactrocera oleae] 417 aa protein | XP_014096877.1 GI: 929373704 |
| odorant receptor 7a-like [Bactrocera oleae] 392 aa protein | XP_014095883.1 GI: 929371891 |
| odorant receptor 46a, isoform A [Bactrocera oleae] 388 aa protein | XP_014095654.1 GI: 929371469 |
| odorant receptor 49a-like [Bactrocera oleae] 394 aa protein | XP_014095510.1 GI: 929371206 |
| odorant receptor 94a-like [Bactrocera oleae] 337 aa protein | XP_014095326.1 GI: 929370867 |
| odorant receptor 67c [Bactrocera oleae] 404 aa protein | XP_014094968.1 GI: 929370189 |
| odorant receptor 94a-like [Bactrocera oleae] 403 aa protein | XP_014094554.1 GI: 929369423 |
| odorant receptor 94a-like [Bactrocera oleae] 392 aa protein | XP_014094548.1 GI: 929369411 |
| putative odorant receptor 85e [Bactrocera oleae] 450 aa protein | XP_014094455.1 GI: 929369240 |
| odorant receptor 13a [Bactrocera oleae] 456 aa protein | XP_014094420.1 GI: 929369174 |
| odorant receptor 63a-like [Bactrocera oleae] 275 aa protein | XP_014094225.1 GI: 929368815 |
| odorant receptor 63a-like [Bactrocera oleae] 414 aa protein | XP_014094224.1 GI: 929368813 |
| odorant receptor 63a-like [Bactrocera oleae] 357 aa protein | XP_014094223.1 GI: 929368811 |
| odorant receptor 85c-like [Bactrocera oleae] 415 aa protein | XP_014093775.1 GI: 929367999 |
| odorant receptor 85c-like [Bactrocera oleae] 211 aa protein | XP_014093774.1 GI: 929367997 |
| putative odorant receptor 85d [Bactrocera oleae] 420 aa protein | XP_014093772.1 GI: 929367993 |
| odorant receptor 7a [Bactrocera oleae] 396 aa protein | XP_014092478.1 GI: 929365645 |
| odorant receptor 94a-like [Bactrocera oleae] 192 aa protein | XP_014092468.1 GI: 929365629 |
| odorant receptor coreceptor [Bactrocera oleae] 473 aa protein | XP_014092453.1 GI: 929365601 |
| odorant receptor 83a [Bactrocera oleae] 473 aa protein | XP_014092452.1 GI: 929365599 |
| odorant receptor 7a-like [Bactrocera oleae] 394 aa protein | XP_014092042.1 GI: 929364851 |
| odorant receptor 10a [Bactrocera oleae] 402 aa protein | XP_014091911.1 GI: 929364611 |
| odorant receptor 82a [Bactrocera oleae] 398 aa protein | XP_014091900.1 GI: 929364589 |
| odorant receptor 67d-like [Bactrocera oleae] 388 aa protein | XP_014091805.1 GI: 929364416 |
| odorant receptor 67d-like [Bactrocera oleae] 388 aa protein | XP_014091792.1 GI: 929364391 |
| odorant receptor 74a [Bactrocera oleae] 402 aa protein | XP_014091648.1 GI: 929364123 |
| odorant receptor 2a-like [Bactrocera oleae] 393 aa protein | XP_014088938.1 GI: 929359208 |
| odorant receptor 94b-like [Bactrocera oleae] 402 aa protein | XP_014088795.1 GI: 929358946 |
| odorant receptor 43a [Bactrocera oleae] 378 aa protein | XP_014088559.1 GI: 929358514 |
| putative odorant receptor 69a, isoform B [Bactrocera oleae] 414 aa protein | XP_014088528.1 GI: 929358458 |
| putative odorant receptor 69a, isoform A [Bactrocera oleae] 289 aa protein | XP_014088513.1 GI: 929358429 |
| odorant receptor 43b-like [Bactrocera oleae] 337 aa protein | XP_014086206.1 GI: 929354211 |
| odorant receptor 74a-like [Bactrocera oleae] 414 aa protein | XP_014085775.1 GI: 929353423 |
| odorant receptor 35a-like [Bactrocera oleae] 417 aa protein | XP_014103705.1 GI: 929352035 |
| putative odorant receptor 92a [Bactrocera oleae] 250 aa protein | XP_014103608.1 GI: 929351857 |
| odorant receptor 7a-like [Bactrocera oleae] 384 aa protein | XP_014103552.1 GI: 929351755 |
| odorant receptor 2a-like [Bactrocera oleae] 384 aa protein | XP_014103551.1 GI: 929351753 |
| odorant receptor 85a-like [Bactrocera oleae] 254 aa protein | XP_014103550.1 GI: 929351751 |
| odorant receptor 22c [Bactrocera oleae] 400 aa protein | XP_014103181.1 GI: 929351088 |
| odorant receptor 24a [Bactrocera oleae] 397 aa protein | XP_014103094.1 GI: 929350935 |
| odorant receptor 49b-like [Bactrocera oleae] 371 aa protein | XP_014102906.1 GI: 929345515 |
| odorant receptor 47b [Bactrocera oleae] 423 aa protein | XP_014096040.1 GI: 929345200 |
| odorant receptor 59a-like [Bactrocera oleae] 378 aa protein | XP_014097365.1 GI: 929344966 |
| odorant receptor 59a-like [Bactrocera oleae] 380 aa protein | XP_014096236.1 GI: 929344964 |
| odorant receptor 53 [Microplitis mediator] 387 aa protein | AKO90017.1 GI: 861722551 |
| odorant receptor 52 [Microplitis mediator] 406 aa protein | AKO90016.1 GI: 861722548 |
| odorant receptor 51 [Microplitis mediator] 410 aa protein | AKO90015.1 GI: 861722545 |
| odorant receptor 50 [Microplitis mediator] 395 aa protein | AKO90014.1 GI: 861722542 |
| odorant receptor 49 [Microplitis mediator] 393 aa protein | AKO90013.1 GI: 861722539 |
| odorant receptor 48 [Microplitis mediator] 401 aa protein | AKO90012.1 GI: 861722536 |
| odorant receptor 47 [Microplitis mediator] 404 aa protein | AKO90011.1 GI: 861722533 |
| odorant receptor 46 [Microplitis mediator] 423 aa protein | AKO90010.1 GI: 861722530 |
| odorant receptor 45 [Microplitis mediator] 393 aa protein | AKO90009.1 GI: 861722527 |
| odorant receptor 44 [Microplitis mediator] 395 aa protein | AKO90008.1 GI: 861722524 |
| odorant receptor 43 [Microplitis mediator] 377 aa protein | AKO90007.1 GI: 861722521 |
| odorant receptor 42 [Microplitis mediator] 381 aa protein | AKO90006.1 GI: 861722518 |
| odorant receptor 41 [Microplitis mediator] 384 aa protein | AKO90005.1 GI: 861722515 |
| odorant receptor 40 [Microplitis mediator] 406 aa protein | AKO90004.1 GI: 861722506 |
| odorant receptor 39 [Microplitis mediator] 349 aa protein | AKO90003.1 GI: 861722503 |
| odorant receptor 38 [Microplitis mediator] 388 aa protein | AKO90002.1 GI: 861722500 |
| odorant receptor 37 [Microplitis mediator] 384 aa protein | AKO90001.1 GI: 861722497 |
| odorant receptor 36 [Microplitis mediator] 382 aa protein | AKO90000.1 GI: 861722494 |

TABLE 3-continued

Odorant receptors.

| Gene Name | Accession Number |
|---|---|
| odorant receptor 35 [Microplitis mediator] 377 aa protein | AKO89999.1 GI: 861722490 |
| odorant receptor 34 [Microplitis mediator] 395 aa protein | AKO89998.1 GI: 861722487 |
| odorant receptor 33 [Microplitis mediator] 384 aa protein | AKO89997.1 GI: 861722484 |
| odorant receptor 32 [Microplitis mediator] 420 aa protein | AKO89996.1 GI: 861722481 |
| odorant receptor 31 [Microplitis mediator] 375 aa protein | AKO89995.1 GI: 861722478 |
| odorant receptor 30 [Microplitis mediator] 383 aa protein | AKO89994.1 GI: 861722475 |
| odorant receptor 29 [Microplitis mediator] 413 aa protein | AKO89993.1 GI: 861722471 |
| odorant receptor 28 [Microplitis mediator] 402 aa protein | AKO89992.1 GI: 861722468 |
| odorant receptor 27 [Microplitis mediator] 403 aa protein | AKO89991.1 GI: 861722465 |
| odorant receptor 26 [Microplitis mediator] 397 aa protein | AKO89990.1 GI: 861722462 |
| odorant receptor 25 [Microplitis mediator] 376 aa protein | AKO89989.1 GI: 861722459 |
| odorant receptor 24 [Microplitis mediator] 260 aa protein | AKO89988.1 GI: 861722456 |
| odorant receptor 23 [Microplitis mediator] 373 aa protein | AKO89987.1 GI: 861722453 |
| odorant receptor 22 [Microplitis mediator] 369 aa protein | AKO89986.1 GI: 861722450 |
| odorant receptor 21 [Microplitis mediator] 392 aa protein | AKO89985.1 GI: 861722447 |
| odorant receptor 20 [Microplitis mediator] 372 aa protein | AKO89984.1 GI: 861722444 |
| odorant receptor 19 [Microplitis mediator] 396 aa protein | AKO89983.1 GI: 861722441 |
| odorant receptor 18 [Microplitis mediator] 390 aa protein | AKO89982.1 GI: 861722438 |
| odorant receptor 17 [Microplitis mediator] 402 aa protein | AKO89981.1 GI: 861722435 |
| odorant receptor 16 [Microplitis mediator] 378 aa protein | AKO89980.1 GI: 861722432 |
| odorant receptor 15 [Microplitis mediator] 385 aa protein | AKO89979.1 GI: 861722429 |
| odorant receptor 14 [Microplitis mediator] 411 aa protein | AKO89978.1 GI: 861722426 |
| odorant receptor 13a-like [Plutella xylostella] 404 aa protein | NP_001296037.1 GI: 822092756 |
| odorant receptor 83b [Spodoptera litura] 473 aa protein | AFN22085.1 GI: 393757441 |
| odorant receptor 50 [Nasonia vitripennis] 373 aa protein | NP_001177496.1 GI: 299522706 |
| Gustatory and odorant receptor 21a 454 aa protein | Q9VPT1.3 GI: 158523347 |
| Gustatory and odorant receptor 63a 512 aa protein | Q9VZL7.1 GI: 20454944 |
| odorant receptor OR83b, partial [Chilo suppressalis] 338 aa protein | ACJ07125.1 GI: 210108262 |
| odorant receptor OR83b, partial [Sesamia inferens] 275 aa protein | ACJ07124.1 GI: 210108191 |
| odorant receptor coreceptor-like [Diuraphis noxia] 127 aa protein | XP_015378374.1 GI: 985425779 |
| gustatory and odorant receptor 63a-like [Halyomorpha halys] 403 aa protein | XP_014293240.1 GI: 939698138 |
| gustatory and odorant receptor 24-like isoform X2 [Halyomorpha halys] 395 aa protein | XP_014282243.1 GI: 939671105 |
| gustatory and odorant receptor 63a-like [Halyomorpha halys] 374 aa protein | XP_014281820.1 GI: 939670013 |
| gustatory and odorant receptor 63a-like [Halyomorpha halys] 395 aa protein | XP_014281153.1 GI: 939668267 |
| gustatory and odorant receptor 22-like [Halyomorpha halys] 134 aa protein | XP_014272022.1 GI: 939643445 |
| gustatory and odorant receptor 22-like [Halyomorpha halys] 199 aa protein | XP_014271847.1 GI: 939642935 |
| gustatory and odorant receptor 22-like isoform X2 [Halyomorpha halys] 312 aa protein | XP_014271842.1 GI: 939642921 |
| gustatory and odorant receptor 24-like isoform X1 [Halyomorpha halys] 395 aa protein | XP_014271841.1 GI: 939642918 |
| gustatory and odorant receptor 24-like isoform X4 [Halyomorpha halys] 316 aa protein | XP_014271840.1 GI: 939642916 |
| gustatory and odorant receptor 24-like isoform X3 [Halyomorpha halys] 366 aa protein | XP_014271839.1 GI: 939642913 |
| gustatory and odorant receptor 24-like isoform X2 [Halyomorpha halys] 395 aa protein | XP_014271838.1 GI: 939642910 |
| gustatory and odorant receptor 24-like isoform X1 [Halyomorpha halys] 399 aa protein | XP_014271836.1 GI: 939642908 |
| gustatory and odorant receptor 21a-like [Bactrocera oleae] 445 aa protein | XP_014101222.1 GI: 929381551 |
| gustatory and odorant receptor 21a-like, partial [Bactrocera oleae] 367 aa protein | XP_014101212.1 GI: 929381535 |
| gustatory and odorant receptor 21a-like, partial [Bactrocera oleae] 278 aa protein | XP_014101173.1 GI: 929381464 |
| gustatory and odorant receptor 21a-like, partial [Bactrocera oleae] 200 aa protein | XP_014100623.1 GI: 929380462 |
| gustatory and odorant receptor 21a [Bactrocera oleae] 456 aa protein | XP_014097799.1 GI: 929375381 |
| gustatory and odorant receptor 22-like [Bactrocera oleae] 129 aa protein | XP_014097326.1 GI: 929374521 |
| odorant receptor 67c-like, partial [Bactrocera oleae] 235 aa protein | XP_014096202.1 GI: 929372471 |
| gustatory and odorant receptor 63a [Bactrocera oleae] 485 aa protein | XP_014095104.1 GI: 929347538 |
| odorant receptor Or83b [Helicoverpa zea] 472 aa protein | AAX14773.1 GI: 60207120 |
| odorant receptor Or83b [Ceratitis capitata] 473 aa protein | AAX14775.1 GI: 60207191 |
| odorant receptor Or83b [Anopheles gambiae] 478 aa protein | AAX14774.1 GI: 60207155 |
| putative odorant receptor [Bombyx mori] 472 aa protein | BAD69585.1 GI: 55583295 |
| Gustatory and odorant receptor 24 457 aa protein | Q7PYF4.4 GI: 384872698 |
| Gustatory and odorant receptor 22 467 aa protein | Q7PMG3.1 GI: 74799392 |

TABLE 3-continued

Odorant receptors.

| Gene Name | Accession Number |
| --- | --- |
| odorant receptor 7 [Culex pipiens pallens] 480 aa protein | AMQ13062.1 GI: 1005652053 |
| putative odorant receptor [Sesamia inferens] 442 aa protein | AGY14587.2 GI: 670657525 |
| putative odorant receptor [Sesamia inferens] 426 aa protein | AGY14585.2 GI: 670657520 |
| putative odorant receptor [Sesamia inferens] 432 aa protein | AGY14579.2 GI: 670657516 |
| putative odorant receptor [Sesamia inferens] 473 aa protein | AGY14565.1 GI: 550848914 |
| putative odorant receptor SinfOR18, partial [Sesamia inferens] 153 aa protein | AIF79425.1 GI: 665823788 |
| putative odorant receptor SinfOR17, partial [Sesamia inferens] 82 aa protein | AIF79424.1 GI: 665823786 |
| putative odorant receptor, partial [Sesamia inferens] 162 aa protein | AGY14595.1 GI: 550848974 |
| putative odorant receptor [Sesamia inferens] 402 aa protein | AGY14593.1 GI: 550848970 |
| putative odorant receptor, partial [Sesamia inferens] 225 aa protein | AGY14592.1 GI: 550848968 |
| putative odorant receptor, partial [Sesamia inferens] 230 aa protein | AGY14591.1 GI: 550848966 |
| putative odorant receptor, partial [Sesamia inferens] 380 aa protein | AGY14590.1 GI: 550848964 |
| putative odorant receptor, partial [Sesamia inferens] 250 aa protein | AGY14589.1 GI: 550848962 |
| putative odorant receptor, partial [Sesamia inferens] 275 aa protein | AGY14588.1 GI: 550848960 |
| putative odorant receptor, partial [Sesamia inferens] 268 aa protein | AGY14586.1 GI: 550848956 |
| putative odorant receptor, partial [Sesamia inferens] 203 aa protein | AGY14584.1 GI: 550848952 |
| putative odorant receptor, partial [Sesamia inferens] 223 aa protein | AGY14583.1 GI: 550848950 |
| putative odorant receptor, partial [Sesamia inferens] 247 aa protein | AGY14582.1 GI: 550848948 |
| putative odorant receptor, partial [Sesamia inferens] 254 aa protein | AGY14581.1 GI: 550848946 |
| putative odorant receptor, partial [Sesamia inferens] 224 aa protein | AGY14578.1 GI: 550848940 |
| putative odorant receptor, partial [Sesamia inferens] 368 aa protein | AGY14577.1 GI: 550848938 |
| putative odorant receptor, partial [Sesamia inferens] 67 aa protein | AGY14576.1 GI: 550848936 |
| putative odorant receptor, partial [Sesamia inferens] 88 aa protein | AGY14575.1 GI: 550848934 |
| putative odorant receptor, partial [Sesamia inferens] 84 aa protein | AGY14574.1 GI: 550848932 |
| putative odorant receptor, partial [Sesamia inferens] 69 aa protein | AGY14573.1 GI: 550848930 |
| putative odorant receptor, partial [Sesamia inferens] 118 aa protein | AGY14572.1 GI: 550848928 |
| putative odorant receptor, partial [Sesamia inferens] 95 aa protein | AGY14571.1 GI: 550848926 |
| putative odorant receptor, partial [Sesamia inferens] 161 aa protein | AGY14570.1 GI: 550848924 |
| putative odorant receptor, partial [Sesamia inferens] 82 aa protein | AGY14568.1 GI: 550848920 |
| putative odorant receptor, partial [Sesamia inferens] 115 aa protein | AGY14567.1 GI: 550848918 |
| putative odorant receptor, partial [Sesamia inferens] 98 aa protein | AGY14566.1 GI: 550848916 |
| odorant receptor 7 [Plutella xylostella] 424 aa protein | AGK43829.1 GI: 484354001 |
| odorant receptor 6 [Plutella xylostella] 424 aa protein | AGK43828.1 GI: 484353999 |
| odorant receptor 5 [Plutella xylostella] 404 aa protein | AGK43827.1 GI: 484353997 |
| odorant receptor 4 [Plutella xylostella] 402 aa protein | AGK43826.1 GI: 484353995 |
| odorant receptor 3 [Plutella xylostella] 403 aa protein | AGK43825.1 GI: 484353993 |
| odorant receptor 1 [Plutella xylostella] 422 aa protein | AGK43824.1 GI: 484353991 |
| odorant receptor 2 [Cnaphalocrocis medinalis] 473 aa protein | AFG73001.1 GI: 383215098 |
| putative odorant receptor [Bombyx mori] 430 aa protein | BAD69586.1 GI: 55583297 |
| putative odorant receptor, partial [Reticulitermes speratus] 382 aa protein | BAU20249.1 GI: 966774588 |
| putative odorant receptor [Reticulitermes speratus] 199 aa protein | BAU20248.1 GI: 966774586 |
| putative odorant receptor [Reticulitermes speratus] 293 aa protein | BAU20247.1 GI: 966774584 |
| putative odorant receptor, partial [Reticulitermes speratus] 125 aa protein | BAU20246.1 GI: 966774582 |
| putative odorant receptor [Reticulitermes speratus] 481 aa protein | BAU20245.1 GI: 966774580 |
| putative odorant receptor [Reticulitermes speratus] 218 aa protein | BAU20244.1 GI: 966774578 |
| putative odorant receptor, partial [Reticulitermes speratus] 119 aa protein | BAU20243.1 GI: 966774576 |
| putative odorant receptor, partial [Reticulitermes speratus] 240 aa protein | BAU20242.1 GI: 966774574 |
| putative odorant receptor, partial [Reticulitermes speratus] 359 aa protein | BAU20241.1 GI: 966774572 |
| putative odorant receptor co-receptor [Reticulitermes speratus] 472 aa protein | BAU20240.1 GI: 966774570 |
| putative odorant receptor, partial [Reticulitermes speratus] 224 aa protein | BAU20239.1 GI: 966774568 |
| putative odorant receptor, partial [Reticulitermes speratus] 235 aa protein | BAU20238.1 GI: 966774566 |
| putative odorant receptor [Reticulitermes speratus] 491 aa protein | BAU20237.1 GI: 966774564 |
| putative odorant receptor [Reticulitermes speratus] 461 aa protein | BAU20236.1 GI: 966774562 |
| putative odorant receptor, partial [Reticulitermes speratus] 211 aa protein | BAU20235.1 GI: 966774560 |
| putative odorant receptor [Reticulitermes speratus] 406 aa protein | BAU20234.1 GI: 966774558 |
| putative odorant receptor, partial [Reticulitermes speratus] 411 aa protein | BAU20233.1 GI: 966774556 |
| putative odorant receptor, partial [Reticulitermes speratus] 469 aa protein | BAU20232.1 GI: 966774554 |
| putative odorant receptor, partial [Reticulitermes speratus] 334 aa protein | BAU20231.1 GI: 966774552 |
| putative odorant receptor 3, partial [Reticulitermes speratus] 429 aa protein | BAU20230.1 GI: 966774550 |
| putative odorant receptor 2 [Reticulitermes speratus] 153 aa protein | BAU20229.1 GI: 966774548 |

TABLE 3-continued

Odorant receptors.

| Gene Name | Accession Number |
|---|---|
| putative odorant receptor 1, partial [Reticulitermes speratus] 101 aa protein | BAU20228.1 GI: 966774546 |
| putative odorant receptor, partial [Sesamia inferens] 156 aa protein | AGY14594.1 GI: 550848972 |
| putative odorant receptor, partial [Sesamia inferens] 107 aa protein | AGY14580.1 GI: 550848944 |
| putative odorant receptor, partial [Sesamia inferens] 70 aa protein | AGY14569.1 GI: 550848922 |
| putative odorant receptor, partial [Sesamia inferens] 188 aa protein | AGY14564.1 GI: 550848912 |
| Odorant receptor coreceptor; Odorant receptor 83b 486 aa protein | Q9VNB5.2 GI: 14285640 |
| Odorant receptor 22a 397 aa protein | P81909.1 GI: 12643687 |
| Odorant receptor 59b 398 aa protein | Q9W1P8.1 GI: 11387003 |
| Odorant receptor 67a 407 aa protein | Q9VT08.2 GI: 14285630 |
| Odorant receptor 43a 376 aa protein | P81917.2 GI: 12643691 |
| Odorant receptor 22b 397 aa protein | P81910.3 GI: 221222515 |
| Odorant receptor 35a 409 aa protein | Q9V3Q2.3 GI: 48429266 |
| Odorant receptor 67d 391 aa protein | Q9VT92.3 GI: 47117341 |
| Odorant receptor 46a, isoform A 381 aa protein | P81919.4 GI: 39932724 |
| Odorant receptor 85b 390 aa protein | Q9VHQ7.2 GI: 14285638 |
| Odorant receptor 67b 421 aa protein | Q9VT20.2 GI: 14285631 |
| Odorant receptor 46a, isoform B 384 aa protein | Q9V3N2.2 GI: 14285623 |
| Odorant receptor 47a 385 aa protein | P81921.1 GI: 12643694 |
| Odorant receptor 10a 406 aa protein | Q9VYZ1.1 GI: 11387000 |
| Odorant receptor 24a 398 aa protein | P81913.4 GI: 251757500 |
| Odorant receptor 47b 412 aa protein | P81922.2 GI: 47606742 |
| Odorant receptor 30a 377 aa protein | Q9VLE5.4 GI: 41019523 |
| Odorant receptor 45a 378 aa protein | Q9V568.3 GI: 37999962 |
| Odorant receptor 42a 406 aa protein | Q9V9I2.3 GI: 22096371 |
| Odorant receptor 49a 396 aa protein | Q9V6A9.3 GI: 22096370 |
| Odorant receptor 1a 392 aa protein | Q9W5G6.2 GI: 14285651 |
| Odorant receptor 13a 418 aa protein | Q9VXL0.2 GI: 14285650 |
| Odorant receptor 88a 401 aa protein | Q9VFN2.2 GI: 14285649 |
| Odorant receptor 98a 397 aa protein | Q9VAZ3.2 GI: 14285647 |
| Odorant receptor 19a 387 aa protein | Q9I816.2 GI: 14285645 |
| Odorant receptor 83a 453 aa protein | Q9VNB3.2 GI: 14285639 |
| Odorant receptor 85c 389 aa protein | Q9VHQ6.2 GI: 14285637 |
| Odorant receptor 85f 392 aa protein | Q9VHE6.1 GI: 14285636 |
| Odorant receptor 82a 385 aa protein | P82986.1 GI: 14285635 |
| Odorant receptor 63a 420 aa protein | Q9VZW8.2 GI: 14285633 |
| Odorant receptor 67c 404 aa protein | Q9VT90.2 GI: 14285632 |
| Odorant receptor 42b 399 aa protein | Q9V9I4.2 GI: 14285628 |
| Odorant receptor 56a 419 aa protein | Q9V8Y7.2 GI: 14285626 |
| Odorant receptor 65a 417 aa protein | P82982.1 GI: 14285620 |
| Odorant receptor 43b 403 aa protein | P81918.3 GI: 14285618 |
| Odorant receptor 22c 402 aa protein | P81911.2 GI: 14285616 |
| Odorant receptor 49b 375 aa protein | Q9V6H2.1 GI: 12643916 |
| Odorant receptor 59a 397 aa protein | P81923.2 GI: 12643696 |
| Odorant receptor 2a 397 aa protein | O46077.2 GI: 12643564 |
| Odorant receptor 7a 413 aa protein | Q9W3I5.1 GI: 11387005 |
| Odorant receptor 9a 392 aa protein | Q9W2U9.1 GI: 11387004 |
| Odorant receptor 74a 404 aa protein | Q9VVF3.1 GI: 11386999 |
| Odorant receptor 85a 397 aa protein | Q9VHS4.1 GI: 11386993 |
| Odorant receptor 94a 387 aa protein | Q9VCS9.1 GI: 11386991 |
| Odorant receptor 94b 383 aa protein | Q9VCS8.1 GI: 11386990 |
| Odorant receptor 45b 396 aa protein | Q9V589.1 GI: 11386985 |
| Odorant receptor 33c 384 aa protein | P81916.1 GI: 11386980 |
| Odorant receptor 33b 379 aa protein | P81915.1 GI: 11386979 |
| Odorant receptor 33a 378 aa protein | P81914.1 GI: 11386978 |
| Odorant receptor 23a 379 aa protein | P81912.1 GI: 11386977 |
| hypothetical protein X777_04609 [Cerapachys biroi] 397 aa protein | EZA62900.1 GI: 607368794 |
| hypothetical protein X777_04608 [Cerapachys biroi] 399 aa protein | EZA62899.1 GI: 607368793 |
| hypothetical protein X777_07630, partial [Cerapachys biroi] 109 aa protein | EZA62813.1 GI: 607368701 |
| hypothetical protein X777_07612, partial [Cerapachys biroi] 305 aa protein | EZA62796.1 GI: 607368684 |
| hypothetical protein X777_07611 [Cerapachys biroi] 376 aa protein | EZA62795.1 GI: 607368683 |
| hypothetical protein X777_10236 [Cerapachys biroi] 402 aa protein | EZA62605.1 GI: 607368492 |
| hypothetical protein X777_03408 [Cerapachys biroi] 389 aa protein | EZA62373.1 GI: 607368259 |
| hypothetical protein X777_03407 [Cerapachys biroi] 390 aa protein | EZA62372.1 GI: 607368258 |
| hypothetical protein X777_03406 [Cerapachys biroi] 391 aa protein | EZA62371.1 GI: 607368257 |
| hypothetical protein X777_03405 [Cerapachys biroi] 391 aa protein | EZA62370.1 GI: 607368256 |

TABLE 3-continued

Odorant receptors.

| Gene Name | Accession Number |
|---|---|
| hypothetical protein X777_03404 [Cerapachys biroi] 382 aa protein | EZA62369.1 GI: 607368255 |
| hypothetical protein X777_03402 [Cerapachys biroi] 390 aa protein | EZA62368.1 GI: 607368254 |
| hypothetical protein X777_03401 [Cerapachys biroi] 392 aa protein | EZA62367.1 GI: 607368253 |
| hypothetical protein X777_09391 [Cerapachys biroi] 395 aa protein | EZA61770.1 GI: 607367631 |
| hypothetical protein X777_09390 [Cerapachys biroi] 396 aa protein | EZA61769.1 GI: 607367630 |
| hypothetical protein X777_09389 [Cerapachys biroi] 399 aa protein | EZA61768.1 GI: 607367629 |
| hypothetical protein X777_09388 [Cerapachys biroi] 394 aa protein | EZA61767.1 GI: 607367628 |
| hypothetical protein X777_09387 [Cerapachys biroi] 397 aa protein | EZA61766.1 GI: 607367627 |
| hypothetical protein X777_09305 [Cerapachys biroi] 394 aa protein | EZA61684.1 GI: 607367545 |
| hypothetical protein X777_07969 [Cerapachys biroi] 350 aa protein | EZA61634.1 GI: 607367487 |
| hypothetical protein X777_07966 [Cerapachys biroi] 396 aa protein | EZA61633.1 GI: 607367486 |
| hypothetical protein X777_07964 [Cerapachys biroi] 395 aa protein | EZA61631.1 GI: 607367484 |
| hypothetical protein X777_12474 [Cerapachys biroi] 375 aa protein | EZA61376.1 GI: 607367226 |
| hypothetical protein X777_08255 [Cerapachys biroi] 397 aa protein | EZA61043.1 GI: 607366887 |
| hypothetical protein X777_14254, partial [Cerapachys biroi] 255 aa protein | EZA60648.1 GI: 607366483 |
| hypothetical protein X777_13392 [Cerapachys biroi] 417 aa protein | EZA60303.1 GI: 607366132 |
| hypothetical protein X777_16159 [Cerapachys biroi] 396 aa protein | EZA59956.1 GI: 607365776 |
| hypothetical protein X777_16072 [Cerapachys biroi] 382 aa protein | EZA59870.1 GI: 607365690 |
| hypothetical protein X777_00307 [Cerapachys biroi] 382 aa protein | EZA59464.1 GI: 607365266 |
| hypothetical protein X777 00306 [Cerapachys biroi] 382 aa protein | EZA59463.1 GI: 607365265 |
| hypothetical protein X777_00305 [Cerapachys biroi] 379 aa protein | EZA59462.1 GI: 607365264 |
| hypothetical protein X777_00304 [Cerapachys biroi] 379 aa protein | EZA59461.1 GI: 607365263 |
| hypothetical protein X777_00303 [Cerapachys biroi] 380 aa protein | EZA59460.1 GI: 607365262 |
| hypothetical protein X777_00693, partial [Cerapachys biroi] 388 aa protein | EZA58872.1 GI: 607364664 |
| hypothetical protein X777 00565, partial [Cerapachys biroi] 110 aa protein | EZA58870.1 GI: 607364661 |
| hypothetical protein X777_00710, partial [Cerapachys biroi] 374 aa protein | EZA58868.1 GI: 607364658 |
| hypothetical protein X777_00709, partial [Cerapachys biroi] 393 aa protein | EZA58867.1 GI: 607364657 |
| hypothetical protein X777_00705, partial [Cerapachys biroi] 391 aa protein | EZA58866.1 GI: 607364656 |
| hypothetical protein X777_00703, partial [Cerapachys biroi] 390 aa protein | EZA58865.1 GI: 607364655 |
| hypothetical protein X777_00702, partial [Cerapachys biroi] 373 aa protein | EZA58864.1 GI: 607364654 |
| hypothetical protein X777_00701, partial [Cerapachys biroi] 390 aa protein | EZA58863.1 GI: 607364653 |
| hypothetical protein X777_00700, partial [Cerapachys biroi] 390 aa protein | EZA58862.1 GI: 607364652 |
| hypothetical protein X777_14780, partial [Cerapachys biroi] 298 aa protein | EZA58612.1 GI: 607364400 |
| hypothetical protein X777_14779 [Cerapachys biroi] 368 aa protein | EZA58611.1 GI: 607364399 |
| hypothetical protein X777_14777 [Cerapachys biroi] 368 aa protein | EZA58610.1 GI: 607364398 |
| hypothetical protein X777_14776 [Cerapachys biroi] 373 aa protein | EZA58609.1 GI: 607364397 |
| hypothetical protein X777_14775 [Cerapachys biroi] 374 aa protein | EZA58608.1 GI: 607364396 |
| hypothetical protein X777_14774 [Cerapachys biroi] 372 aa protein | EZA58607.1 GI: 607364395 |

TABLE 3-continued

Odorant receptors.

| Gene Name | Accession Number |
|---|---|
| hypothetical protein X777_14773 [Cerapachys biroi] 367 aa protein | EZA58606.1 GI: 607364394 |
| hypothetical protein X777_14772 [Cerapachys biroi] 372 aa protein | EZA58605.1 GI: 607364393 |
| hypothetical protein X777_14770 [Cerapachys biroi] 370 aa protein | EZA58604.1 GI: 607364392 |
| hypothetical protein X777_14769 [Cerapachys biroi] 371 aa protein | EZA58603.1 GI: 607364391 |
| hypothetical protein X777_14768 [Cerapachys biroi] 369 aa protein | EZA58602.1 GI: 607364390 |
| hypothetical protein X777_14767 [Cerapachys biroi] 365 aa protein | EZA58601.1 GI: 607364389 |
| hypothetical protein X777_14766, partial [Cerapachys biroi] 362 aa protein | EZA58600.1 GI: 607364388 |
| hypothetical protein X777_01291 [Cerapachys biroi] 417 aa protein | EZA58334.1 GI: 607364113 |
| hypothetical protein X777_01236 [Cerapachys biroi] 391 aa protein | EZA58279.1 GI: 607364058 |
| hypothetical protein X777_01205 [Cerapachys biroi] 403 aa protein | EZA58248.1 GI: 607364027 |
| hypothetical protein X777 01932, partial [Cerapachys biroi] 212 aa protein | EZA58117.1 GI: 607363890 |
| hypothetical protein X777_01931, partial [Cerapachys biroi] 386 aa protein | EZA58116.1 GI: 607363889 |
| hypothetical protein X777_01929 [Cerapachys biroi] 387 aa protein | EZA58115.1 GI: 607363888 |
| hypothetical protein X777_01925, partial [Cerapachys biroi] 387 aa protein | EZA58113.1 GI: 607363886 |
| hypothetical protein X777_01917, partial [Cerapachys biroi] 388 aa protein | EZA58112.1 GI: 607363885 |
| hypothetical protein X777_01492, partial [Cerapachys biroi] 346 aa protein | EZA58111.1 GI: 607363883 |
| hypothetical protein X777_01491 [Cerapachys biroi] 394 aa protein | EZA58110.1 GI: 607363882 |
| hypothetical protein X777_01490 [Cerapachys biroi] 392 aa protein | EZA58109.1 GI: 607363881 |
| hypothetical protein X777_02093, partial [Cerapachys biroi] 368 aa protein | EZA57554.1 GI: 607363317 |
| hypothetical protein X777_02092 [Cerapachys biroi] 377 aa protein | EZA57553.1 GI: 607363316 |
| hypothetical protein X777_02090 [Cerapachys biroi] 395 aa protein | EZA57552.1 GI: 607363315 |
| hypothetical protein X777_02089 [Cerapachys biroi] 387 aa protein | EZA57551.1 GI: 607363314 |
| hypothetical protein X777_02088 [Cerapachys biroi] 393 aa protein | EZA57550.1 GI: 607363313 |
| hypothetical protein X777_02087 [Cerapachys biroi] 381 aa protein | EZA57549.1 GI: 607363312 |
| hypothetical protein X777_02086 [Cerapachys biroi] 378 aa protein | EZA57548.1 GI: 607363311 |
| hypothetical protein X777_02085 [Cerapachys biroi] 387 aa protein | EZA57547.1 GI: 607363310 |
| hypothetical protein X777_02082 [Cerapachys biroi] 396 aa protein | EZA57546.1 GI: 607363309 |
| hypothetical protein X777_02081 [Cerapachys biroi] 377 aa protein | EZA57545.1 GI: 607363308 |
| hypothetical protein X777_02080 [Cerapachys biroi] 385 aa protein | EZA57544.1 GI: 607363307 |
| hypothetical protein X777_02079 [Cerapachys biroi] 382 aa protein | EZA57543.1 GI: 607363306 |
| hypothetical protein X777_02078 [Cerapachys biroi] 384 aa protein | EZA57542.1 GI: 607363305 |
| hypothetical protein X777_02075 [Cerapachys biroi] 385 aa protein | EZA57540.1 GI: 607363303 |
| hypothetical protein X777_02074 [Cerapachys biroi] 387 aa protein | EZA57539.1 GI: 607363302 |
| hypothetical protein X777_02073 [Cerapachys biroi] 383 aa protein | EZA57538.1 GI: 607363301 |
| hypothetical protein X777_02072 [Cerapachys biroi] 385 aa protein | EZA57537.1 GI: 607363300 |
| hypothetical protein X777_02071 [Cerapachys biroi] 382 aa protein | EZA57536.1 GI: 607363299 |
| hypothetical protein X777_02070 [Cerapachys biroi] 384 aa protein | EZA57535.1 GI: 607363298 |
| hypothetical protein X777_02069, partial [Cerapachys biroi] 367 aa protein | EZA57534.1 GI: 607363297 |

TABLE 3-continued

Odorant receptors.

| Gene Name | Accession Number |
|---|---|
| hypothetical protein X777_02068 [Cerapachys biroi] 384 aa protein | EZA57533.1 GI: 607363296 |
| hypothetical protein X777_02067 [Cerapachys biroi] 384 aa protein | EZA57532.1 GI: 607363295 |
| hypothetical protein X777_02065 [Cerapachys biroi] 379 aa protein | EZA57531.1 GI: 607363294 |
| hypothetical protein X777_01603, partial [Cerapachys biroi] 388 aa protein | EZA56997.1 GI: 607362752 |
| hypothetical protein X777_01602, partial [Cerapachys biroi] 390 aa protein | EZA56996.1 GI: 607362751 |
| hypothetical protein X777_01601, partial [Cerapachys biroi] 389 aa protein | EZA56995.1 GI: 607362750 |
| hypothetical protein X777_01600, partial [Cerapachys biroi] 379 aa protein | EZA56994.1 GI: 607362749 |
| hypothetical protein X777_02369 [Cerapachys biroi] 375 aa protein | EZA56762.1 GI: 607362510 |
| hypothetical protein X777_02368 [Cerapachys biroi] 368 aa protein | EZA56761.1 GI: 607362509 |
| hypothetical protein X777_02340 [Cerapachys biroi] 398 aa protein | EZA56735.1 GI: 607362483 |
| hypothetical protein X777_03347 [Cerapachys biroi] 391 aa protein | EZA56560.1 GI: 607362304 |
| hypothetical protein X777_03346, partial [Cerapachys biroi] 377 aa protein | EZA56559.1 GI: 607362303 |
| hypothetical protein X777_03345 [Cerapachys biroi] 392 aa protein | EZA56558.1 GI: 607362302 |
| hypothetical protein X777_03344 [Cerapachys biroi] 372 aa protein | EZA56557.1 GI: 607362301 |
| hypothetical protein X777_03736, partial [Cerapachys biroi] 383 aa protein | EZA56086.1 GI: 607361821 |
| hypothetical protein X777_04121 [Cerapachys biroi] 383 aa protein | EZA55902.1 GI: 607361626 |
| hypothetical protein X777_04120 [Cerapachys biroi] 383 aa protein | EZA55901.1 GI: 607361625 |
| hypothetical protein X777_03929 [Cerapachys biroi] 388 aa protein | EZA55755.1 GI: 607361477 |
| hypothetical protein X777_03928, partial [Cerapachys biroi] 335 aa protein | EZA55754.1 GI: 607361476 |
| hypothetical protein X777_04285 [Cerapachys biroi] 388 aa protein | EZA55491.1 GI: 607361197 |
| hypothetical protein X777_04264 [Cerapachys biroi] 396 aa protein | EZA55471.1 GI: 607361177 |
| hypothetical protein X777_04263 [Cerapachys biroi] 393 aa protein | EZA55470.1 GI: 607361176 |
| hypothetical protein X777_04768 [Cerapachys biroi] 299 aa protein | EZA55372.1 GI: 607361071 |
| hypothetical protein X777_04767 [Cerapachys biroi] 395 aa protein | EZA55371.1 GI: 607361070 |
| hypothetical protein X777_04765 [Cerapachys biroi] 412 aa protein | EZA55369.1 GI: 607361068 |
| hypothetical protein X777_05311 [Cerapachys biroi] 388 aa protein | EZA55133.1 GI: 607360814 |
| hypothetical protein X777_05310 [Cerapachys biroi] 391 aa protein | EZA55132.1 GI: 607360813 |
| hypothetical protein X777_05285, partial [Cerapachys biroi] 347 aa protein | EZA55110.1 GI: 607360791 |
| hypothetical protein X777_05369 [Cerapachys biroi] 395 aa protein | EZA55090.1 GI: 607360767 |
| hypothetical protein X777_05368 [Cerapachys biroi] 398 aa protein | EZA55089.1 GI: 607360766 |
| hypothetical protein X777_05462 [Cerapachys biroi] 391 aa protein | EZA54938.1 GI: 607360613 |
| hypothetical protein X777_05757 [Cerapachys biroi] 404 aa protein | EZA54481.1 GI: 607360141 |
| hypothetical protein X777_05686, partial [Cerapachys biroi] 347 aa protein | EZA54448.1 GI: 607360105 |
| hypothetical protein X777_05685 [Cerapachys biroi] 394 aa protein | EZA54447.1 GI: 607360104 |
| hypothetical protein X777_05682, partial [Cerapachys biroi] 344 aa protein | EZA54446.1 GI: 607360103 |
| hypothetical protein X777_05679, partial [Cerapachys biroi] 385 aa protein | EZA54444.1 GI: 607360101 |
| hypothetical protein X777_05674, partial [Cerapachys biroi] 346 aa protein | EZA54439.1 GI: 607360096 |
| hypothetical protein X777_05671, partial [Cerapachys biroi] 307 aa protein | EZA54437.1 GI: 607360094 |

TABLE 3-continued

Odorant receptors.

| Gene Name | Accession Number |
|---|---|
| hypothetical protein X777_05670, partial [Cerapachys biroi] 86 aa protein | EZA54436.1 GI: 607360093 |
| hypothetical protein X777_05669 [Cerapachys biroi] 401 aa protein | EZA54435.1 GI: 607360092 |
| hypothetical protein X777_05668 [Cerapachys biroi] 393 aa protein | EZA54434.1 GI: 607360091 |
| hypothetical protein X777_05665 [Cerapachys biroi] 353 aa protein | EZA54432.1 GI: 607360089 |
| hypothetical protein X777_05664 [Cerapachys biroi] 393 aa protein | EZA54431.1 GI: 607360088 |
| hypothetical protein X777_05662 [Cerapachys biroi] 399 aa protein | EZA54429.1 GI: 607360086 |
| hypothetical protein X777_05661 [Cerapachys biroi] 396 aa protein | EZA54428.1 GI: 607360085 |
| hypothetical protein X777_05660 [Cerapachys biroi] 394 aa protein | EZA54427.1 GI: 607360084 |
| hypothetical protein X777_05658 [Cerapachys biroi] 394 aa protein | EZA54426.1 GI: 607360083 |
| hypothetical protein X777_05656, partial [Cerapachys biroi] 347 aa protein | EZA54424.1 GI: 607360081 |
| hypothetical protein X777_05655 [Cerapachys biroi] 396 aa protein | EZA54423.1 GI: 607360080 |
| hypothetical protein X777_05651 [Cerapachys biroi] 394 aa protein | EZA54421.1 GI: 607360078 |
| hypothetical protein X777_05650 [Cerapachys biroi] 394 aa protein | EZA54420.1 GI: 607360077 |
| hypothetical protein X777_05649 [Cerapachys biroi] 395 aa protein | EZA54419.1 GI: 607360076 |
| hypothetical protein X777_05648 [Cerapachys biroi] 394 aa protein | EZA54418.1 GI: 607360075 |
| hypothetical protein X777_07020, partial [Cerapachys biroi] 305 aa protein | EZA53552.1 GI: 607359176 |
| hypothetical protein X777_07019 [Cerapachys biroi] 352 aa protein | EZA53551.1 GI: 607359175 |
| hypothetical protein X777_08120 [Cerapachys biroi] 391 aa protein | EZA52637.1 GI: 607358221 |
| hypothetical protein X777_08119 [Cerapachys biroi] 389 aa protein | EZA52636.1 GI: 607358220 |
| hypothetical protein X777_08118 [Cerapachys biroi] 359 aa protein | EZA52635.1 GI: 607358219 |
| hypothetical protein X777_08117 [Cerapachys biroi] 354 aa protein | EZA52634.1 GI: 607358218 |
| hypothetical protein X777_08040 [Cerapachys biroi] 387 aa protein | EZA52558.1 GI: 607358142 |
| hypothetical protein X777_08039 [Cerapachys biroi] 398 aa protein | EZA52557.1 GI: 607358141 |
| hypothetical protein X777_08037 [Cerapachys biroi] 402 aa protein | EZA52556.1 GI: 607358140 |
| hypothetical protein X777_08034 [Cerapachys biroi] 387 aa protein | EZA52555.1 GI: 607358139 |
| hypothetical protein X777_08033 [Cerapachys biroi] 395 aa protein | EZA52554.1 GI: 607358138 |
| hypothetical protein X777_08032 [Cerapachys biroi] 404 aa protein | EZA52553.1 GI: 607358137 |
| hypothetical protein X777_08610 [Cerapachys biroi] 393 aa protein | EZA52503.1 GI: 607358081 |
| hypothetical protein X777_08609 [Cerapachys biroi] 393 aa protein | EZA52502.1 GI: 607358080 |
| hypothetical protein X777_08608, partial [Cerapachys biroi] 348 aa protein | EZA52501.1 GI: 607358079 |
| hypothetical protein X777_08641 [Cerapachys biroi] 403 aa protein | EZA52498.1 GI: 607358074 |
| hypothetical protein X777_08639 [Cerapachys biroi] 405 aa protein | EZA52497.1 GI: 607358073 |
| hypothetical protein X777_08638 [Cerapachys biroi] 415 aa protein | EZA52496.1 GI: 607358072 |
| hypothetical protein X777_08637 [Cerapachys biroi] 410 aa protein | EZA52495.1 GI: 607358071 |
| hypothetical protein X777_08636 [Cerapachys biroi] 387 aa protein | EZA52494.1 GI: 607358070 |
| hypothetical protein X777_08635 [Cerapachys biroi] 412 aa protein | EZA52493.1 GI: 607358069 |
| hypothetical protein X777_08634, partial [Cerapachys biroi] 296 aa protein | EZA52492.1 GI: 607358068 |
| hypothetical protein X777_08633, partial [Cerapachys biroi] 296 aa protein | EZA52491.1 GI: 607358067 |

TABLE 3-continued

Odorant receptors.

| Gene Name | Accession Number |
|---|---|
| hypothetical protein X777_08535 [Cerapachys biroi] 369 aa protein | EZA52460.1 GI: 607358030 |
| hypothetical protein X777_08647 [Cerapachys biroi] 409 aa protein | EZA52136.1 GI: 607357695 |
| hypothetical protein X777_09139, partial [Cerapachys biroi] 67 aa protein | EZA52127.1 GI: 607357681 |
| hypothetical protein X777_09138 [Cerapachys biroi] 403 aa protein | EZA52126.1 GI: 607357680 |
| hypothetical protein X777_09136 [Cerapachys biroi] 404 aa protein | EZA52125.1 GI: 607357679 |
| hypothetical protein X777_09135 [Cerapachys biroi] 404 aa protein | EZA52124.1 GI: 607357678 |
| hypothetical protein X777_09133 [Cerapachys biroi] 398 aa protein | EZA52123.1 GI: 607357677 |
| hypothetical protein X777_09132 [Cerapachys biroi] 408 aa protein | EZA52122.1 GI: 607357676 |
| hypothetical protein X777_09131 [Cerapachys biroi] 410 aa protein | EZA52121.1 GI: 607357675 |
| hypothetical protein X777_09130 [Cerapachys biroi] 410 aa protein | EZA52120.1 GI: 607357674 |
| hypothetical protein X777_09129 [Cerapachys biroi] 410 aa protein | EZA52119.1 GI: 607357673 |
| hypothetical protein X777_09127 [Cerapachys biroi] 413 aa protein | EZA52118.1 GI: 607357672 |
| hypothetical protein X777_09126 [Cerapachys biroi] 405 aa protein | EZA52117.1 GI: 607357671 |
| hypothetical protein X777_09124 [Cerapachys biroi] 402 aa protein | EZA52116.1 GI: 607357670 |
| hypothetical protein X777_09123 [Cerapachys biroi] 406 aa protein | EZA52115.1 GI: 607357669 |
| hypothetical protein X777_09298, partial [Cerapachys biroi] 316 aa protein | EZA52015.1 GI: 607357565 |
| hypothetical protein X777_08804 [Cerapachys biroi] 397 aa protein | EZA51620.1 GI: 607357154 |
| hypothetical protein X777_08803 [Cerapachys biroi] 395 aa protein | EZA51619.1 GI: 607357153 |
| hypothetical protein X777_08801 [Cerapachys biroi] 394 aa protein | EZA51618.1 GI: 607357152 |
| hypothetical protein X777_08800 [Cerapachys biroi] 395 aa protein | EZA51617.1 GI: 607357151 |
| hypothetical protein X777_08799 [Cerapachys biroi] 394 aa protein | EZA51616.1 GI: 607357150 |
| hypothetical protein X777_08798 [Cerapachys biroi] 394 aa protein | EZA51615.1 GI: 607357149 |
| hypothetical protein X777_08797 [Cerapachys biroi] 394 aa protein | EZA51614.1 GI: 607357148 |
| hypothetical protein X777_08795 [Cerapachys biroi] 397 aa protein | EZA51612.1 GI: 607357146 |
| hypothetical protein X777_08794 [Cerapachys biroi] 395 aa protein | EZA51611.1 GI: 607357145 |
| hypothetical protein X777_08793 [Cerapachys biroi] 353 aa protein | EZA51610.1 GI: 607357144 |
| hypothetical protein X777_08790 [Cerapachys biroi] 394 aa protein | EZA51607.1 GI: 607357141 |
| hypothetical protein X777_08789 [Cerapachys biroi] 394 aa protein | EZA51606.1 GI: 607357140 |
| hypothetical protein X777_08788 [Cerapachys biroi] 394 aa protein | EZA51605.1 GI: 607357139 |
| hypothetical protein X777_08787 [Cerapachys biroi] 390 aa protein | EZA51604.1 GI: 607357138 |
| hypothetical protein X777_08786 [Cerapachys biroi] 394 aa protein | EZA51603.1 GI: 607357137 |
| hypothetical protein X777_08785 [Cerapachys biroi] 394 aa protein | EZA51602.1 GI: 607357136 |
| hypothetical protein X777_08783, partial [Cerapachys biroi] 109 aa protein | EZA51600.1 GI: 607357134 |
| hypothetical protein X777_09662 [Cerapachys biroi] 379 aa protein | EZA51393.1 GI: 607356910 |
| hypothetical protein X777_10267, partial [Cerapachys biroi] 277 aa protein | EZA51181.1 GI: 607356681 |
| hypothetical protein X777_10879 [Cerapachys biroi] 350 aa protein | EZA50908.1 GI: 607356383 |
| hypothetical protein X777_10878 [Cerapachys biroi] 388 aa protein | EZA50907.1 GI: 607356382 |
| hypothetical protein X777_10877 [Cerapachys biroi] 393 aa protein | EZA50906.1 GI: 607356381 |

TABLE 3-continued

Odorant receptors.

| Gene Name | Accession Number |
|---|---|
| hypothetical protein X777_10876 [Cerapachys biroi] 394 aa protein | EZA50905.1 GI: 607356380 |
| hypothetical protein X777_10874 [Cerapachys biroi] 393 aa protein | EZA50904.1 GI: 607356379 |
| hypothetical protein X777_10873 [Cerapachys biroi] 393 aa protein | EZA50903.1 GI: 607356378 |
| hypothetical protein X777_10872 [Cerapachys biroi] 394 aa protein | EZA50902.1 GI: 607356377 |
| hypothetical protein X777_10850 [Cerapachys biroi] 343 aa protein | EZA50881.1 GI: 607356356 |
| hypothetical protein X777_10849 [Cerapachys biroi] 331 aa protein | EZA50880.1 GI: 607356355 |
| hypothetical protein X777_10848 [Cerapachys biroi] 361 aa protein | EZA50879.1 GI: 607356354 |
| hypothetical protein X777_10661, partial [Cerapachys biroi] 286 aa protein | EZA50468.1 GI: 607355920 |
| hypothetical protein X777_10602 [Cerapachys biroi] 409 aa protein | EZA50409.1 GI: 607355861 |
| hypothetical protein X777_11257 [Cerapachys biroi] 393 aa protein | EZA50334.1 GI: 607355781 |
| hypothetical protein X777_11279 [Cerapachys biroi] 393 aa protein | EZA50278.1 GI: 607355719 |
| hypothetical protein X777_11081 [Cerapachys biroi] 365 aa protein | EZA50243.1 GI: 607355683 |
| hypothetical protein X777_11573 [Cerapachys biroi] 368 aa protein | EZA50143.1 GI: 607355570 |
| hypothetical protein X777_11736 [Cerapachys biroi] 398 aa protein | EZA50071.1 GI: 607355491 |
| hypothetical protein X777_11513 [Cerapachys biroi] 402 aa protein | EZA50024.1 GI: 607355443 |
| hypothetical protein X777_11512 [Cerapachys biroi] 373 aa protein | EZA50023.1 GI: 607355442 |
| hypothetical protein X777_11511 [Cerapachys biroi] 399 aa protein | EZA50022.1 GI: 607355441 |
| hypothetical protein X777_11510 [Cerapachys biroi] 400 aa protein | EZA50021.1 GI: 607355440 |
| hypothetical protein X777_11509 [Cerapachys biroi] 422 aa protein | EZA50020.1 GI: 607355439 |
| hypothetical protein X777_11508 [Cerapachys biroi] 410 aa protein | EZA50019.1 GI: 607355438 |
| hypothetical protein X777_11507 [Cerapachys biroi] 410 aa protein | EZA50018.1 GI: 607355437 |
| hypothetical protein X777_11506 [Cerapachys biroi] 405 aa protein | EZA50017.1 GI: 607355436 |
| hypothetical protein X777_11880 [Cerapachys biroi] 394 aa protein | EZA49382.1 GI: 607354770 |
| hypothetical protein X777_11877 [Cerapachys biroi] 400 aa protein | EZA49381.1 GI: 607354769 |
| hypothetical protein X777_12371 [Cerapachys biroi] 478 aa protein | EZA49341.1 GI: 607354726 |
| hypothetical protein X777_12369, partial [Cerapachys biroi] 376 aa protein | EZA49339.1 GI: 607354724 |
| hypothetical protein X777_12360 [Cerapachys biroi] 391 aa protein | EZA49330.1 GI: 607354715 |
| hypothetical protein X777_12504 [Cerapachys biroi] 391 aa protein | EZA49105.1 GI: 607354473 |
| hypothetical protein X777_12787 [Cerapachys biroi] 379 aa protein | EZA49075.1 GI: 607354438 |
| hypothetical protein X777_12783 [Cerapachys biroi] 352 aa protein | EZA49074.1 GI: 607354437 |
| hypothetical protein X777_12649, partial [Cerapachys biroi] 108 aa protein | EZA49046.1 GI: 607354404 |
| hypothetical protein X777_12820 [Cerapachys biroi] 366 aa protein | EZA49011.1 GI: 607354363 |
| hypothetical protein X777_12819 [Cerapachys biroi] 392 aa protein | EZA49010.1 GI: 607354362 |
| hypothetical protein X777_12817 [Cerapachys biroi] 404 aa protein | EZA49009.1 GI: 607354361 |
| hypothetical protein X777_12816 [Cerapachys biroi] 395 aa protein | EZA49008.1 GI: 607354360 |
| hypothetical protein X777_12814 [Cerapachys biroi] 402 aa protein | EZA49006.1 GI: 607354358 |
| hypothetical protein X777_12813 [Cerapachys biroi] 403 aa protein | EZA49005.1 GI: 607354357 |
| hypothetical protein X777_12906 [Cerapachys biroi] 393 aa protein | EZA48943.1 GI: 607354289 |

TABLE 3-continued

Odorant receptors.

| Gene Name | Accession Number |
| --- | --- |
| hypothetical protein X777_12905 [Cerapachys biroi] 395 aa protein | EZA48942.1 GI: 607354288 |
| hypothetical protein X777_12904 [Cerapachys biroi] 393 aa protein | EZA48941.1 GI: 607354287 |
| hypothetical protein X777_12903 [Cerapachys biroi] 393 aa protein | EZA48940.1 GI: 607354286 |
| hypothetical protein X777_12902 [Cerapachys biroi] 393 aa protein | EZA48939.1 GI: 607354285 |
| hypothetical protein X777_12901 [Cerapachys biroi] 395 aa protein | EZA48938.1 GI: 607354284 |
| hypothetical protein X777_12900 [Cerapachys biroi] 394 aa protein | EZA48937.1 GI: 607354283 |
| hypothetical protein X777_12898 [Cerapachys biroi] 394 aa protein | EZA48935.1 GI: 607354281 |
| hypothetical protein X777_12897 [Cerapachys biroi] 394 aa protein | EZA48934.1 GI: 607354280 |
| hypothetical protein X777_12960 [Cerapachys biroi] 391 aa protein | EZA48918.1 GI: 607354259 |
| hypothetical protein X777_14095 [Cerapachys biroi] 393 aa protein | EZA48295.1 GI: 607353550 |
| hypothetical protein X777_14075 [Cerapachys biroi] 403 aa protein | EZA48275.1 GI: 607353530 |
| hypothetical protein X777_14074 [Cerapachys biroi] 395 aa protein | EZA48274.1 GI: 607353529 |
| hypothetical protein X777_14073 [Cerapachys biroi] 400 aa protein | EZA48273.1 GI: 607353528 |
| hypothetical protein X777_14071 [Cerapachys biroi] 398 aa protein | EZA48271.1 GI: 607353526 |
| hypothetical protein X777_14069 [Cerapachys biroi] 395 aa protein | EZA48269.1 GI: 607353524 |
| hypothetical protein X777_14157 [Cerapachys biroi] 393 aa protein | EZA48257.1 GI: 607353504 |
| hypothetical protein X777_14156 [Cerapachys biroi] 393 aa protein | EZA48256.1 GI: 607353503 |
| hypothetical protein X777_14154 [Cerapachys biroi] 294 aa protein | EZA48254.1 GI: 607353501 |
| hypothetical protein X777_14153 [Cerapachys biroi] 393 aa protein | EZA48253.1 GI: 607353500 |
| hypothetical protein X777_14152 [Cerapachys biroi] 390 aa protein | EZA48252.1 GI: 607353499 |
| hypothetical protein X777_14151 [Cerapachys biroi] 393 aa protein | EZA48251.1 GI: 607353498 |
| hypothetical protein X777_14150 [Cerapachys biroi] 393 aa protein | EZA48250.1 GI: 607353497 |
| hypothetical protein X777_14149 [Cerapachys biroi] 390 aa protein | EZA48249.1 GI: 607353496 |
| hypothetical protein X777_14148 [Cerapachys biroi] 422 aa protein | EZA48248.1 GI: 607353495 |
| hypothetical protein X777_14146 [Cerapachys biroi] 397 aa protein | EZA48247.1 GI: 607353494 |
| hypothetical protein X777_14145 [Cerapachys biroi] 397 aa protein | EZA48246.1 GI: 607353493 |
| hypothetical protein X777_14144 [Cerapachys biroi] 400 aa protein | EZA48245.1 GI: 607353492 |
| hypothetical protein X777_14142 [Cerapachys biroi] 392 aa protein | EZA48243.1 GI: 607353490 |
| hypothetical protein X777_14137 [Cerapachys biroi] 395 aa protein | EZA48239.1 GI: 607353486 |
| hypothetical protein X777_14135 [Cerapachys biroi] 370 aa protein | EZA48238.1 GI: 607353485 |
| hypothetical protein X777_14134 [Cerapachys biroi] 393 aa protein | EZA48237.1 GI: 607353484 |
| hypothetical protein X777_14133 [Cerapachys biroi] 393 aa protein | EZA48236.1 GI: 607353483 |
| hypothetical protein X777_14132 [Cerapachys biroi] 393 aa protein | EZA48235.1 GI: 607353482 |
| hypothetical protein X777_14128 [Cerapachys biroi] 393 aa protein | EZA48232.1 GI: 607353479 |
| hypothetical protein X777_14127 [Cerapachys biroi] 392 aa protein | EZA48231.1 GI: 607353478 |
| hypothetical protein X777_14238, partial [Cerapachys biroi] 110 aa protein | EZA48207.1 GI: 607353449 |
| hypothetical protein X777_14325 [Cerapachys biroi] 391 aa protein | EZA48143.1 GI: 607353377 |
| hypothetical protein X777_14324 [Cerapachys biroi] 391 aa protein | EZA48142.1 GI: 607353376 |

TABLE 3-continued

Odorant receptors.

| Gene Name | Accession Number |
|---|---|
| hypothetical protein X777_14322 [Cerapachys biroi] 391 aa protein | EZA48140.1 GI: 607353374 |
| hypothetical protein X777_14321 [Cerapachys biroi] 332 aa protein | EZA48139.1 GI: 607353373 |
| hypothetical protein X777_14320 [Cerapachys biroi] 319 aa protein | EZA48138.1 GI: 607353372 |
| hypothetical protein X777_14319 [Cerapachys biroi] 394 aa protein | EZA48137.1 GI: 607353371 |
| hypothetical protein X777_14318, partial [Cerapachys biroi] 245 aa protein | EZA48136.1 GI: 607353370 |
| hypothetical protein X777_14166 [Cerapachys biroi] 410 aa protein | EZA48057.1 GI: 607353283 |
| hypothetical protein X777_14448 [Cerapachys biroi] 397 aa protein | EZA48027.1 GI: 607353226 |
| hypothetical protein X777_14454, partial [Cerapachys biroi] 110 aa protein | EZA48023.1 GI: 607353220 |
| hypothetical protein X777_15046, partial [Cerapachys biroi] 347 aa protein | EZA47950.1 GI: 607353115 |
| hypothetical protein X777_15045 [Cerapachys biroi] 277 aa protein | EZA47949.1 GI: 607353114 |
| hypothetical protein X777_15044 [Cerapachys biroi] 395 aa protein | EZA47948.1 GI: 607353113 |
| hypothetical protein X777_14494 [Cerapachys biroi] 393 aa protein | EZA47923.1 GI: 607353084 |
| hypothetical protein X777_14493, partial [Cerapachys biroi] 338 aa protein | EZA47922.1 GI: 607353083 |
| hypothetical protein X777_14490 [Cerapachys biroi] 392 aa protein | EZA47921.1 GI: 607353082 |
| hypothetical protein X777_14489 [Cerapachys biroi] 391 aa protein | EZA47920.1 GI: 607353081 |
| hypothetical protein X777_14488 [Cerapachys biroi] 357 aa protein | EZA47919.1 GI: 607353080 |
| hypothetical protein X777_14486 [Cerapachys biroi] 405 aa protein | EZA47917.1 GI: 607353078 |
| hypothetical protein X777_14484, partial [Cerapachys biroi] 367 aa protein | EZA47916.1 GI: 607353077 |
| hypothetical protein X777_15215 [Cerapachys biroi] 400 aa protein | EZA47891.1 GI: 607353036 |
| hypothetical protein X777_15213 [Cerapachys biroi] 396 aa protein | EZA47890.1 GI: 607353035 |
| hypothetical protein X777_15211 [Cerapachys biroi] 400 aa protein | EZA47889.1 GI: 607353034 |
| hypothetical protein X777_15210 [Cerapachys biroi] 402 aa protein | EZA47888.1 GI: 607353033 |
| hypothetical protein X777_15208 [Cerapachys biroi] 395 aa protein | EZA47887.1 GI: 607353032 |
| hypothetical protein X777_15207 [Cerapachys biroi] 391 aa protein | EZA47886.1 GI: 607353031 |
| hypothetical protein X777_15257 [Cerapachys biroi] 367 aa protein | EZA47872.1 GI: 607353013 |
| hypothetical protein X777_15254, partial [Cerapachys biroi] 203 aa protein | EZA47870.1 GI: 607353011 |
| hypothetical protein X777_15516 [Cerapachys biroi] 392 aa protein | EZA47757.1 GI: 607352872 |
| hypothetical protein X777_16325, partial [Cerapachys biroi] 347 aa protein | EZA47405.1 GI: 607352456 |
| hypothetical protein X777_16550 [Cerapachys biroi] 399 aa protein | EZA47250.1 GI: 607352245 |
| hypothetical protein X777_16549, partial [Cerapachys biroi] 387 aa protein | EZA47249.1 GI: 607352244 |
| hypothetical protein X777_16545, partial [Cerapachys biroi] 387 aa protein | EZA47248.1 GI: 607352243 |
| hypothetical protein X777_16583, partial [Cerapachys biroi] 115 aa protein | EZA47246.1 GI: 607352234 |
| hypothetical protein X777_16640, partial [Cerapachys biroi] 381 aa protein | EZA47175.1 GI: 607352154 |
| hypothetical protein X777_16639 [Cerapachys biroi] 388 aa protein | EZA47174.1 GI: 607352153 |
| hypothetical protein X777_16686 [Cerapachys biroi] 390 aa protein | EZA47122.1 GI: 607352100 |
| hypothetical protein X777_16765, partial [Cerapachys biroi] 257 aa protein | EZA47082.1 GI: 607352037 |
| hypothetical protein X777_17009, partial [Cerapachys biroi] 290 aa protein | EZA47033.1 GI: 607351973 |
| hypothetical protein X777_17008 [Cerapachys biroi] 395 aa protein | EZA47032.1 GI: 607351972 |

TABLE 3-continued

Odorant receptors.

| Gene Name | Accession Number |
| --- | --- |
| hypothetical protein X777_17007 [Cerapachys biroi] 395 aa protein | EZA47031.1 GI: 607351971 |
| hypothetical protein X777_17006 [Cerapachys biroi] 357 aa protein | EZA47030.1 GI: 607351970 |
| hypothetical protein X777_17005 [Cerapachys biroi] 394 aa protein | EZA47029.1 GI: 607351969 |
| hypothetical protein X777_17004 [Cerapachys biroi] 394 aa protein | EZA47028.1 GI: 607351968 |
| hypothetical protein X777_17037 [Cerapachys biroi] 392 aa protein | EZA47010.1 GI: 607351937 |
| hypothetical protein X777_16829 [Cerapachys biroi] 394 aa protein | EZA46975.1 GI: 607351833 |
| hypothetical protein X777_16828 [Cerapachys biroi] 377 aa protein | EZA46974.1 GI: 607351832 |
| hypothetical protein X777_16827 [Cerapachys biroi] 395 aa protein | EZA46973.1 GI: 607351831 |
| hypothetical protein X777_16826 [Cerapachys biroi] 396 aa protein | EZA46972.1 GI: 607351830 |
| hypothetical protein X777_16825 [Cerapachys biroi] 390 aa protein | EZA46971.1 GI: 607351829 |
| hypothetical protein X777_16823 [Cerapachys biroi] 390 aa protein | EZA46970.1 GI: 607351828 |
| hypothetical protein X777_16822 [Cerapachys biroi] 390 aa protein | EZA46969.1 GI: 607351827 |
| hypothetical protein X777_00574 [Cerapachys biroi] 394 aa protein | EZA46944.1 GI: 607351788 |
| hypothetical protein X777_00572, partial [Cerapachys biroi] 284 aa protein | EZA46933.1 GI: 607351766 |
| hypothetical protein X777_00683, partial [Cerapachys biroi] 390 aa protein | EZA46927.1 GI: 607351750 |
| hypothetical protein X777_01187 [Cerapachys biroi] 395 aa protein | EZA46822.1 GI: 607351544 |
| hypothetical protein X777_01186 [Cerapachys biroi] 237 aa protein | EZA46821.1 GI: 607351543 |
| hypothetical protein X777_01182 [Cerapachys biroi] 393 aa protein | EZA46818.1 GI: 607351530 |
| hypothetical protein X777_01496, partial [Cerapachys biroi] 310 aa protein | EZA46816.1 GI: 607351520 |
| hypothetical protein X777_01992, partial [Cerapachys biroi] 104 aa protein | EZA46773.1 GI: 607351376 |
| hypothetical protein X777_02013 [Cerapachys biroi] 391 aa protein | EZA46772.1 GI: 607351374 |
| hypothetical protein X777_02041 [Cerapachys biroi] 391 aa protein | EZA46770.1 GI: 607351360 |
| hypothetical protein X777_02040 [Cerapachys biroi] 399 aa protein | EZA46769.1 GI: 607351359 |
| hypothetical protein X777_02038 [Cerapachys biroi] 394 aa protein | EZA46768.1 GI: 607351358 |
| hypothetical protein X777_02037 [Cerapachys biroi] 395 aa protein | EZA46767.1 GI: 607351357 |
| hypothetical protein X777_02036 [Cerapachys biroi] 351 aa protein | EZA46766.1 GI: 607351356 |
| hypothetical protein X777_02035 [Cerapachys biroi] 391 aa protein | EZA46765.1 GI: 607351355 |
| hypothetical protein X777_02034 [Cerapachys biroi] 391 aa protein | EZA46764.1 GI: 607351354 |
| hypothetical protein X777_02033 [Cerapachys biroi] 395 aa protein | EZA46763.1 GI: 607351353 |
| hypothetical protein X777_02154, partial [Cerapachys biroi] 388 aa protein | EZA46750.1 GI: 607351325 |
| hypothetical protein X777_02182, partial [Cerapachys biroi] 115 aa protein | EZA46748.1 GI: 607351315 |
| hypothetical protein X777_02391 [Cerapachys biroi] 395 aa protein | EZA46731.1 GI: 607351243 |
| hypothetical protein X777_02373 [Cerapachys biroi] 392 aa protein | EZA46714.1 GI: 607351226 |
| hypothetical protein X777_02372 [Cerapachys biroi] 313 aa protein | EZA46713.1 GI: 607351225 |
| hypothetical protein X777 03732 [Cerapachys biroi] 243 aa protein | EZA46661.1 GI: 607350938 |
| hypothetical protein X777_04259, partial [Cerapachys biroi] 110 aa protein | EZA46601.1 GI: 607350634 |
| hypothetical protein X777_04309, partial [Cerapachys biroi] 70 aa protein | EZA46600.1 GI: 607350630 |
| hypothetical protein X777_00022, partial [Cerapachys biroi] 114 aa protein | EZA46571.1 GI: 607349175 |

TABLE 3-continued

Odorant receptors.

| Gene Name | Accession Number |
| --- | --- |
| hypothetical protein X777_00149, partial [Cerapachys biroi] 64 aa protein | EZA46447.1 GI: 607348111 |
| hypothetical protein X777_00236, partial [Cerapachys biroi] 230 aa protein | EZA46364.1 GI: 607347729 |
| Odorant receptor Or1; AgOr1 417 aa protein | Q8WTE7.1 GI: 44888255 |
| Odorant receptor Or2; AgOr2 378 aa protein | Q8WTE6.1 GI: 44888254 |
| uncharacterized protein LOC107040665 [Diachasma alloeum] 1186 aa protein | XP_015116341.1 GI: 970881283 |
| uncharacterized protein LOC107038380 [Diachasma alloeum] 1173 aa protein | XP_015112930.1 GI: 970880645 |
| uncharacterized protein LOC107040682 [Diachasma alloeum] 417 aa protein | XP_015116364.1 GI: 970881287 |
| uncharacterized protein LOC107038389 [Diachasma alloeum] 770 aa protein | XP_015112957.1 GI: 970880649 |
| Sensory neuron membrane protein 1; Short = SNMP1Dmel 551 aa protein | Q9VDD3.2 GI: 74868468 |
| General odorant-binding protein lush; Flags: Precursor 153 aa protein | O02372.1 GI: 61214421 |
| uncharacterized protein LOC107171897, partial [Diuraphis noxia] 135 aa protein | XP_015377642.1 GI: 985424240 |
| uncharacterized protein LOC107171052, partial [Diuraphis noxia] 131 aa protein | XP_015376771.1 GI: 985422638 |
| uncharacterized protein LOC107166471 [Diuraphis noxia] 403 aa protein | XP_015370631.1 GI: 985410377 |
| uncharacterized protein LOC107167838 [Diuraphis noxia] 113 aa protein | XP_015372525.1 GI: 985386955 |
| uncharacterized protein LOC107047710 [Diachasma alloeum] 134 aa protein | XP_015125998.1 GI: 970918690 |
| uncharacterized protein LOC107046523 [Diachasma alloeum] 435 aa protein | XP_015124630.1 GI: 970916388 |
| uncharacterized protein LOC107045828 [Diachasma alloeum] 131 aa protein | XP_015123693.1 GI: 970914661 |
| uncharacterized protein LOC107045792 [Diachasma alloeum] 274 aa protein | XP_015123634.1 GI: 970914552 |
| uncharacterized protein LOC107045791 [Diachasma alloeum] 377 aa protein | XP_015123633.1 GI: 970914550 |
| uncharacterized protein LOC107045316 isoform X2 [Diachasma alloeum] 352 aa protein | XP_015123022.1 GI: 970913423 |
| uncharacterized protein LOC107044760 [Diachasma alloeum] 389 aa protein | XP_015122273.1 GI: 970912048 |
| uncharacterized protein LOC107043060 [Diachasma alloeum] 234 aa protein | XP_015119847.1 GI: 970907601 |
| uncharacterized protein LOC107041505 [Diachasma alloeum] 154 aa protein | XP_015117568.1 GI: 970903454 |
| uncharacterized protein LOC107041471 [Diachasma alloeum] 392 aa protein | XP_015117541.1 GI: 970903394 |
| uncharacterized protein LOC107041468 [Diachasma alloeum] 284 aa protein | XP_015117538.1 GI: 970903388 |
| uncharacterized protein LOC107041058 [Diachasma alloeum] 171 aa protein | XP_015116902.1 GI: 970902214 |
| uncharacterized protein LOC107041057 [Diachasma alloeum] 173 aa protein | XP_015116901.1 GI: 970902212 |
| uncharacterized protein LOC107040351 [Diachasma alloeum] 394 aa protein | XP_015115892.1 GI: 970900366 |
| uncharacterized protein LOC107040339 [Diachasma alloeum] 313 aa-protein | XP_015115876.1 GI: 970900336 |
| uncharacterized protein LOC107039160 isoform X3 [Diachasma alloeum] 335 aa protein | XP_015114121.1 GI: 970897155 |
| uncharacterized protein LOC107039160 isoform X2 [Diachasma alloeum] 383 aa protein | XP_015114120.1 GI: 970897153 |
| uncharacterized protein LOC107039160 isoform X1 [Diachasma alloeum] 391 aa protein | XP_015114119.1 GI: 970897151 |
| uncharacterized protein LOC107039144 isoform X2 [Diachasma alloeum] 327 aa protein | XP_015114102.1 GI: 970897120 |
| uncharacterized protein LOC107039144 isoform X1 [Diachasma alloeum] 383 aa protein | XP_015114101.1 GI: 970897118 |
| uncharacterized protein LOC107038269 [Diachasma alloeum] 398 aa protein | XP_015112765.1 GI: 970894635 |
| uncharacterized protein LOC107038076 [Diachasma alloeum] 416 aa protein | XP_015112442.1 GI: 970894044 |
| uncharacterized protein LOC107038024 [Diachasma alloeum] 115 aa protein | XP_015112374.1 GI: 970893921 |
| uncharacterized protein LOC107037155 [Diachasma alloeum] 144 aa protein | XP_015111030.1 GI: 970891453 |
| uncharacterized protein LOC107037131 [Diachasma alloeum] 393 aa protein | XP_015111001.1 GI: 970891401 |

TABLE 3-continued

Odorant receptors.

| Gene Name | Accession Number |
|---|---|
| uncharacterized protein LOC107037008 [Diachasma alloeum] 428 aa protein | XP_015110801.1 GI: 970891030 |
| uncharacterized protein LOC107036995 [Diachasma alloeum] 399 aa protein | XP_015110788.1 GI: 970891006 |
| uncharacterized protein LOC107036721 [Diachasma alloeum] 203 aa protein | XP_015110342.1 GI: 970890185 |
| uncharacterized protein LOC107036608 [Diachasma alloeum] 126 aa protein | XP_015110155.1 GI: 970889843 |
| uncharacterized protein LOC107036569 [Diachasma alloeum] 322 aa protein | XP_015110092.1 GI: 970889731 |
| uncharacterized protein LOC107036562 [Diachasma alloeum] 245 aa protein | XP_015110086.1 GI: 970889719 |
| uncharacterized protein LOC107035960 [Diachasma alloeum] 410 aa protein | XP_015109114.1 GI: 970887963 |
| uncharacterized protein LOC107048689 [Diachasma alloeum] 172 aa protein | XP_015127489.1 GI: 970885577 |
| uncharacterized protein LOC107048383 [Diachasma alloeum] 221 aa protein | XP_015127016.1 GI: 970884731 |
| uncharacterized protein LOC107048083 [Diachasma alloeum] 255 aa protein | XP_015126543.1 GI: 970883864 |
| uncharacterized protein LOC107041464 [Diachasma alloeum] 339 aa protein | XP_015117536.1 GI: 970881499 |
| uncharacterized protein LOC107041401 isoform X1 [Diachasma alloeum] 405 aa protein | XP_015117436.1 GI: 970881482 |
| uncharacterized protein LOC107040856 [Diachasma alloeum] 386 aa protein | XP_015116611.1 GI: 970881336 |
| uncharacterized protein LOC107040848 [Diachasma alloeum] 391 aa protein | XP_015116602.1 GI: 970881334 |
| uncharacterized protein LOC106692217, partial [Halyomorpha halys] 120 aa protein | XP_014293607.1 GI: 939698834 |
| uncharacterized protein LOC106692125, partial [Halyomorpha halys] 120 aa protein | XP_014293519.1 GI: 939698671 |
| uncharacterized protein LOC106691728, partial [Halyomorpha halys] 309 aa protein | XP_014293070.1 GI: 939697820 |
| uncharacterized protein LOC106690974 [Halyomorpha halys] 381 aa protein | XP_014292085.1 GI: 939695932 |
| uncharacterized protein LOC106690972 [Halyomorpha halys] 334 aa protein | XP_014292082.1 GI: 939695928 |
| uncharacterized protein LOC106690969 [Halyomorpha halys] 280 aa protein | XP_014292080.1 GI: 939695923 |
| uncharacterized protein LOC106690968 isoform X2 [Halyomorpha halys] 356 aa protein | XP_014292079.1 GI: 939695921 |
| uncharacterized protein LOC106690968 isoform X1 [Halyomorpha halys] 381 aa protein | XP_014292078.1 GI: 939695919 |
| uncharacterized protein LOC106690056 [Halyomorpha halys] 419 aa protein | XP_014290808.1 GI: 939693496 |
| uncharacterized protein LOC106689927 isoform X2 [Halyomorpha halys] 402 aa protein | XP_014290638.1 GI: 939693169 |
| uncharacterized protein LOC106689927 isoform X1 [Halyomorpha halys] 430 aa protein | XP_014290637.1 GI: 939693167 |
| uncharacterized protein LOC106689925 [Halyomorpha halys] 430 aa protein | XP_014290634.1 GI: 939693163 |
| uncharacterized protein LOC106689759 [Halyomorpha halys] 126 aa protein | XP_014290404.1 GI: 939692739 |
| uncharacterized protein LOC106689626, partial [Halyomorpha halys] 361 aa protein | XP_014290195.1 GI: 939692350 |
| uncharacterized protein LOC106689110 [Halyomorpha halys] 395 aa protein | XP_014289383.1 GI: 939690780 |
| uncharacterized protein LOC106689027, partial [Halyomorpha halys] 349 aa protein | XP_014289256.1 GI: 939690551 |
| uncharacterized protein LOC106688861 [Halyomorpha halys] 354 aa protein | XP_014289023.1 GI: 939690122 |
| uncharacterized protein LOC106688860 [Halyomorpha halys] 402 aa protein | XP_014289021.1 GI: 939690120 |
| uncharacterized protein LOC106688858 [Halyomorpha halys] 401 aa protein | XP_014289019.1 GI: 939690116 |
| uncharacterized protein LOC106688856 isoform X3 [Halyomorpha halys] 291 aa protein | XP_014289018.1 GI: 939690114 |
| uncharacterized protein LOC106688856 isoform X3 [Halyomorpha halys] 291 aa protein | XP_014289017.1 GI: 939690112 |
| uncharacterized protein LOC106688856 isoform X2 [Halyomorpha halys] 349 aa protein | XP_014289016.1 GI: 939690110 |
| uncharacterized protein LOC106688856 isoform X1 [Halyomorpha halys] 391 aa protein | XP_014289015.1 GI: 939690108 |
| uncharacterized protein LOC106688855 [Halyomorpha halys] 122 aa protein | XP_014289014.1 GI: 939690106 |

TABLE 3-continued

Odorant receptors.

| Gene Name | Accession Number |
|---|---|
| uncharacterized protein LOC106688854 [Halyomorpha halys] 355 aa protein | XP_014289013.1 GI: 939690104 |
| uncharacterized protein LOC106688852 [Halyomorpha halys] 402 aa protein | XP_014289011.1 GI: 939690100 |
| uncharacterized protein LOC106688565 [Halyomorpha halys] 399 aa protein | XP_014288559.1 GI: 939689255 |
| uncharacterized protein LOC106688504 [Halyomorpha halys] 415 aa protein | XP_014288483.1 GI: 939689114 |
| uncharacterized protein LOC106688133 isoform X2 [Halyomorpha halys] 264 aa protein | XP_014287937.1 GI: 939688097 |
| uncharacterized protein LOC106688133 isoform X1 [Halyomorpha halys] 299 aa protein | XP_014287936.1 GI: 939688095 |
| uncharacterized protein LOC106687951 [Halyomorpha halys] 205 aa protein | XP_014287635.1 GI: 939687191 |
| uncharacterized protein LOC106687745 [Halyomorpha halys] 117 aa protein | XP_014287267.1 GI: 939686093 |
| uncharacterized protein LOC106687729 [Halyomorpha halys] 450 aa protein | XP_014287248.1 GI: 939686031 |
| uncharacterized protein LOC106687584 [Halyomorpha halys] 355 aa protein | XP_014287044.1 GI: 939685359 |
| uncharacterized protein LOC106687583 [Halyomorpha halys] 254 aa protein | XP_014287043.1 GI: 939685355 |
| uncharacterized protein LOC106687100 [Halyomorpha halys] 438 aa protein | XP_014286277.1 GI: 939683074 |
| uncharacterized protein LOC106686230 [Halyomorpha halys] 410 aa protein | XP_014284895.1 GI: 939678679 |
| uncharacterized protein LOC106686225 isoform X2 [Halyomorpha halys] 382 aa protein | XP_014284891.1 GI: 939678662 |
| uncharacterized protein LOC106686225 isoform X1 [Halyomorpha halys] 419 aa protein | XP_014284890.1 GI: 939678658 |
| uncharacterized protein LOC106684746 isoform X2 [Halyomorpha halys] 235 aa protein | XP_014282485.1 GI: 939671752 |
| uncharacterized protein LOC106684678 isoform X2 [Halyomorpha halys] 140 aa protein | XP_014282387.1 GI: 939671481 |
| uncharacterized protein LOC106684574 [Halyomorpha halys] 142 aa protein | XP_014282214.1 GI: 939671038 |
| uncharacterized protein LOC106684269 [Halyomorpha halys] 211 aa protein | XP_014281731.1 GI: 939669764 |
| uncharacterized protein LOC106682571 [Halyomorpha halys] 373 aa protein | XP_014278976.1 GI: 939662570 |
| uncharacterized protein LOC106682449 isoform X2 [Halyomorpha halys] 322 aa protein | XP_014278794.1 GI: 939662115 |
| uncharacterized protein LOC106682449 isoform X1 [Halyomorpha halys] 323 aa protein | XP_014278793.1 GI: 939662112 |
| uncharacterized protein LOC106682407, partial [Halyomorpha halys] 265 aa protein | XP_014278714.1 GI: 939661920 |
| uncharacterized protein LOC106681266 [Halyomorpha halys] 432 aa protein | XP_014276987.1 GI: 939657430 |
| uncharacterized protein LOC106681101, partial [Halyomorpha halys] 182 aa protein | XP_014276742.1 GI: 939656824 |
| uncharacterized protein LOC106681099 [Halyomorpha halys] 323 aa protein | XP_014276740.1 GI: 939656818 |
| uncharacterized protein LOC106680703 [Halyomorpha halys] 228 aa protein | XP_014276067.1 GI: 939654990 |
| uncharacterized protein LOC106680013 [Halyomorpha halys] 197 aa protein | XP_014274955.1 GI: 939651857 |
| uncharacterized protein LOC106679982 [Halyomorpha halys] 398 aa protein | XP_014274899.1 GI: 939651709 |
| uncharacterized protein LOC106679017 isoform X3 [Halyomorpha halys] 392 aa protein | XP_014273409.1 GI: 939647459 |
| uncharacterized protein LOC106679017 isoform X2 [Halyomorpha halys] 402 aa protein | XP_014273408.1 GI: 939647457 |
| uncharacterized protein LOC106679017 isoform X1 [Halyomorpha halys] 427 aa protein | XP_014273407.1 GI: 939647455 |
| uncharacterized protein LOC106678921 isoform X2 [Halyomorpha halys] 385 aa protein | XP_014273270.1 GI: 939647059 |
| uncharacterized protein LOC106678921 isoform X1 [Halyomorpha halys] 437 aa protein | XP_014273269.1 GI: 939647056 |
| uncharacterized protein LOC106678586 [Halyomorpha halys] 317 aa protein | XP_014272658.1 GI: 939645318 |
| uncharacterized protein LOC106678578 [Halyomorpha halys] 169 aa protein | XP_014272643.1 GI: 939645272 |
| uncharacterized protein LOC106678240 [Halyomorpha halys] 388 aa protein | XP_014272140.1 GI: 939643797 |
| uncharacterized protein LOC106677363 isoform X2 [Halyomorpha halys] 417 aa protein | XP_014270733.1 GI: 939639742 |

TABLE 3-continued

Odorant receptors.

| Gene Name | Accession Number |
|---|---|
| uncharacterized protein LOC106677363 isoform X1 [Halyomorpha halys] 419 aa protein | XP_014270732.1 GI: 939639738 |
| uncharacterized protein LOC106677357 isoform X2 [Halyomorpha halys] 370 aa protein | XP_014270726.1 GI: 939639710 |
| uncharacterized protein LOC106677357 isoform X1 [Halyomorpha halys] 404 aa protein | XP_014270725.1 GI: 939639708 |
| uncharacterized protein LOC106677356 [Halyomorpha halys] 355 aa protein | XP_014270724.1 GI: 939639706 |
| uncharacterized protein LOC106693012 [Halyomorpha halys] 415 aa protein | XP_014294797.1 GI: 939638057 |
| uncharacterized protein LOC106693004 [Halyomorpha halys] 297 aa protein | XP_014294789.1 GI: 939638041 |
| uncharacterized protein LOC106692786 isoform X2 [Halyomorpha halys] 348 aa protein | XP_014294440.1 GI: 939637036 |
| uncharacterized protein LOC106692425 isoform X2 [Halyomorpha halys] 378 aa protein | XP_014293860.1 GI: 939635393 |
| uncharacterized protein LOC106687938 [Halyomorpha halys] 358 aa protein | XP_014287615.1 GI: 939633287 |
| uncharacterized protein LOC106684029 isoform X1 [Halyomorpha halys] 400 aa protein | XP_014281345.1 GI: 939631378 |
| uncharacterized protein LOC106683667 isoform X2 [Halyomorpha halys] 345 aa protein | XP_014280777.1 GI: 939631233 |
| uncharacterized protein LOC106683640 [Halyomorpha halys] 353 aa protein | XP_014280732.1 GI: 939631224 |
| uncharacterized protein LOC106683586, partial [Halyomorpha halys] 400 aa protein | XP_014280634.1 GI: 939631202 |
| uncharacterized protein LOC106681860 [Halyomorpha halys] 402 aa protein | XP_014277890.1 GI: 939630417 |
| uncharacterized protein LOC106681850 [Halyomorpha halys] 358 aa protein | XP_014277878.1 GI: 939630413 |
| uncharacterized protein LOC106681777 [Halyomorpha halys] 428 aa protein | XP_014277766.1 GI: 939630367 |
| uncharacterized protein LOC106678083 [Halyomorpha halys] 426 aa protein | XP_014271872.1 GI: 939628624 |
| uncharacterized protein LOC106692148 [Halyomorpha halys] 372 aa protein | XP_014293574.1 GI: 939627857 |
| olfactory receptor 3 [Bombyx mori] 439 aa protein | NP_001036925.1 GI: 112982950 |
| olfactory receptor 9 [Plutella xylostella] 449 aa protein | ALV82554.1 GI: 971834990 |
| olfactory receptor 2 [Bombyx mori] 472 aa protein | NP_001037060.1 GI: 112983084 |
| olfactory receptor 1 [Bombyx mori] 430 aa protein | NP_001036875.1 GI: 1 12983558 |
| Chain A, Structure Of Pheromone-binding Protein 1 In Complex With (z,z)-11,13-Hexadecadienol 140 aa protein | 4INX_A GI: 459358923 |
| Chain A, Structure Of Pheromone-binding Protein 1 In Complex With (11z,13z)-Hexadecadienal 140 aa protein | 4INW_A GI: 459358922 |
| olfactory receptor [Ostrinia furnacalis] 424 aa protein | BAH57982.1 GI: 229365469 |
| olfactory receptor [Ostrinia latipennis] 424 aa protein | BAH57981.1 GI: 229365467 |
| olfactory receptor [Ostrinia nubilalis] 424 aa protein | BAH57980.1 GI: 229365465 |
| olfactory receptor [Ostrinia ovalipennis] 424 aa protein | BAH57979.1 GI: 229365463 |
| olfactory receptor [Ostrinia palustralis] 424 aa protein | BAH57978.1 GI: 229365461 |
| olfactory receptor [Ostrinia zealis] 424 aa protein | BAH57977.1 GI: 229365459 |
| olfactory receptor [Ostrinia zaguliaevi] 424 aa protein | BAH57976.1 GI: 229365457 |
| olfactory receptor [Ostrinia scapulalis] 424 aa protein | BAH57975.1 GI: 229365455 |
| Sequence 10 from patent U.S. Pat. No. 7,601,829 486 aa protein | ADA08702.1 GI: 281014387 |
| Sequence 6 from patent U.S. Pat. No. 7,601,829 478 aa protein | ADA08700.1 GI: 281014385 |
| Sequence 4 from patent U.S. Pat. No. 7,601,829 472 aa protein | ADA08699.1 GI: 281014384 |
| Sequence 2 from patent U.S. Pat. No. 7,601,829 473 aa protein | ADA08698.1 GI: 281014383 |
| Sequence 10 from patent U.S. Pat. No. 7,550,574 486 aa protein | ACW03545.1 GI: 259184438 |
| Sequence 6 from patent U.S. Pat. No. 7,550,574 478 aa protein | ACW03543.1 GI: 259184436 |
| Sequence 4 from patent U.S. Pat. No. 7,550,574 472 aa protein | ACW03542.1 GI: 259184435 |
| Sequence 2 from patent U.S. Pat. No. 7,550,574 473 aa protein | ACW03541.1 GI: 259184434 |
| putative chemosensory receptor 2 [Antheraea pernyi] 472 aa protein | CAD88205.1 GI: 32399809 |
| hypothetical protein TcasGA2_TC032780 [Tribolium castaneum] 1096 aa protein | KYB27892.1 GI: 1004400598 |
| olfactory receptor 65 [Bombyx mori] 239 aa protein | NP_001166622.1 GI: 290560867 |
| olfactory receptor 13 [Bombyx mori] 385 aa protein | NP_001166603.1 GI: 290559921 |
| olfactory receptor-like [Bombyx mori] 410 aa protein | NP_001159623.1 GI: 261245107 |
| olfactory receptor 4 [Bombyx mori] 424 aa protein | NP_001036926.1 GI: 112982926 |
| AKH receptor variant AKHR3 isoform AKHR-B [Pseudoregma bambucicola] 591 aa protein | AKH80290.1 GI: 822549471 |
| olfactory receptor 10 [Bombyx mori] 388 aa protein | NP_001104819.1 GI: 162462631 |
| olfactory receptor 6 [Bombyx mori] 407 aa protein | NP_001036928.1 GI: 112982988 |
| olfactory receptor 5 [Bombyx mori] 417 aa protein | NP_001036927.1 GI: 112982948 |
| olfactory receptor 2 [Chilo suppressalis] 474 aa protein | AFQ94048.1 GI: 402746958 |
| unknown [Dendroctonus ponderosae] 382 aa protein | AEE63423.1 GI: 332376567 |
| unknown [Dendroctonus ponderosae] 396 aa protein | AEE63326.1 GI: 332376372 |

TABLE 3-continued

Odorant receptors.

| Gene Name | Accession Number |
|---|---|
| unknown [Dendroctonus ponderosae] 404 aa protein | AEE63155.1 GI: 332376029 |
| unknown [Dendroctonus ponderosae] 394 aa protein | AEE62970.1 GI: 332375658 |
| unknown [Dendroctonus ponderosae] 395 aa protein | AEE62637.1 GI: 332374992 |
| unknown [Dendroctonus ponderosae] 400 aa protein | AEE62488.1 GI: 332374694 |
| unknown [Dendroctonus ponderosae] 480 aa protein | AEE62122.1 GI: 332373962 |
| unknown [Dendroctonus ponderosae] 396 aa protein | AEE61493.1 GI: 332372702 |
| unknown [Dendroctonus ponderosae] 403 aa protein | AEE61404.1 GI: 332372524 |
| olfactory receptor [Dendroctonus ponderosae] 480 aa protein | AFI45064.1 GI: 385200032 |
| putative olfactory receptor 18 [Spodoptera littoralis] 398 aa protein | ACL81189.1 GI: 220715234 |
| putative olfactory receptor 18 [Mamestra brassicae] 400 aa protein | ACL81188.1 GI: 220715232 |
| putative olfactory receptor 18 [Helicoverpa armigera] 398 aa protein | ACL81187.1 GI: 220715230 |
| putative olfactory receptor 18 [Helicoverpa zea] 398 aa protein | ACL81186.1 GI: 220715228 |
| putative olfactory receptor 18 [Agrotis segetum] 400 aa protein | ACL81185.1 GI: 220715226 |
| putative olfactory receptor 18 [Sesamia nonagrioides] 400 aa protein | ACL81184.1 GI: 220715224 |
| Sequence 18 from patent U.S. Pat. No. 7,601,829 33 aa protein | ADA08710.1 GI: 281014395 |
| Sequence 17 from patent U.S. Pat. No. 7,601,829 43 aa protein | ADA08709.1 GI: 281014394 |
| Sequence 16 from patent U.S. Pat. No. 7,601,829 43 aa protein | ADA08708.1 GI: 281014393 |
| Sequence 15 from patent U.S. Pat. No. 7,601,829 43 aa protein | ADA08707.1 GI: 281014392 |
| Sequence 14 from patent U.S. Pat. No. 7,601,829 43 aa protein | ADA08706.1 GI: 281014391 |
| Sequence 13 from patent U.S. Pat. No. 7,601,829 11 aa protein | ADA08705.1 GI: 281014390 |
| Sequence 12 from patent U.S. Pat. No. 7,601,829 16 aa protein | ADA08704.1 GI: 281014389 |
| Sequence 11 from patent U.S. Pat. No. 7,601,829 498 aa protein | ADA08703.1 GI: 281014388 |
| Sequence 8 from patent U.S. Pat. No. 7,601,829 486 aa protein | ADA08701.1 GI: 281014386 |
| Sequence 18 from patent U.S. Pat. No. 7,550,574 33 aa protein | ACW03553.1 GI: 259184446 |
| Sequence 17 from patent U.S. Pat. No. 7,550,574 43 aa protein | ACW03552.1 GI: 259184445 |
| Sequence 16 from patent U.S. Pat. No. 7,550,574 43 aa protein | ACW03551.1 GI: 259184444 |
| Sequence 15 from patent U.S. Pat. No. 7,550,574 43 aa protein | ACW03550.1 GI: 259184443 |
| Sequence 14 from patent U.S. Pat. No. 7,550,574 43 aa protein | ACW03549.1 GI: 259184442 |
| Sequence 13 from patent U.S. Pat. No. 7,550,574 11 aa protein | ACW03548.1 GI: 259184441 |
| Sequence 12 from patent U.S. Pat. No. 7,550,574 16 aa protein | ACW03547.1 GI: 259184440 |
| Sequence 11 from patent U.S. Pat. No. 7,550,574 498 aa protein | ACW03546.1 GI: 259184439 |
| Sequence 8 from patent U.S. Pat. No. 7,550,574 486 aa protein | ACW03544.1 GI: 259184437 |
| Sequence 6 from patent U.S. Pat. No. 7,541,155 486 aa protein | ACS10701.1 GI: 239686039 |
| Sequence 4 from patent U.S. Pat. No. 7,541,155 376 aa protein | ACS10700.1 GI: 239686038 |
| unnamed protein product [Drosophila melanogaster] 379 aa protein | CAY86014.1 GI: 237677885 |
| unnamed protein product [Drosophila melanogaster] 376 aa protein | CAY86011.1 GI: 237677879 |
| unnamed protein product [Drosophila melanogaster] 467 aa protein | CAY86010.1 GI: 237677877 |
| unnamed protein product, partial [Drosophila melanogaster] 153 aa protein | CAY86009.1 GI: 237677875 |
| Sequence 104 from patent U.S. Pat. No. 7,241,881 486 aa protein | ABU34893.1 GI: 155712034 |
| Sequence 100 from patent U.S. Pat. No. 7,241,881 392 aa protein | ABU34891.1 GI: 155712032 |
| Sequence 98 from patent U.S. Pat. No. 7,241,881 406 aa protein | ABU34890.1 GI: 155712031 |
| Sequence 78 from patent U.S. Pat. No. 7,241,881 378 aa protein | ABU34880.1 GI: 155712021 |
| Sequence 70 from patent U.S. Pat. No. 7,241,881 392 aa protein | ABU34876.1 GI: 155712017 |
| Sequence 68 from patent U.S. Pat. No. 7,241,881 397 aa protein | ABU34875.1 GI: 155712016 |
| Sequence 66 from patent U.S. Pat. No. 7,241,881 413 aa protein | ABU34874.1 GI: 155712015 |
| Sequence 50 from patent U.S. Pat. No. 7,241,881 398 aa protein | ABU34866.1 GI: 155712007 |
| Sequence 40 from patent U.S. Pat. No. 7,241,881 412 aa protein | ABU34861.1 GI: 155712002 |
| Sequence 34 from patent U.S. Pat. No. 7,241,881 383 aa protein | ABU34858.1 GI: 155711999 |
| Sequence 30 from patent U.S. Pat. No. 7,241,881 396 aa protein | ABU34856.1 GI: 155711997 |
| Sequence 28 from patent U.S. Pat. No. 7,241,881 375 aa protein | ABU34855.1 GI: 155711996 |
| Sequence 24 from patent U.S. Pat. No. 7,241,881 385 aa protein | ABU34853.1 GI: 155711994 |
| Sequence 20 from patent U.S. Pat. No. 7,241,881 379 aa protein | ABU34851.1 GI: 155711992 |
| Sequence 18 from patent U.S. Pat. No. 7,241,881 378 aa protein | ABU34850.1 GI: 155711991 |
| Sequence 16 from patent U.S. Pat. No. 7,241,881 379 aa protein | ABU34849.1 GI: 155711990 |
| Sequence 12 from patent U.S. Pat. No. 7,241,881 379 aa protein | ABU34847.1 GI: 155711988 |
| Sequence 10 from patent U.S. Pat. No. 7,241,881 397 aa protein | ABU34846.1 GI: 155711987 |
| Sequence 8 from patent U.S. Pat. No. 7,241,881 397 aa protein | ABU34845.1 GI: 155711986 |
| Sequence 6 from patent U.S. Pat. No. 7,241,881 376 aa protein | ABU34844.1 GI: 155711985 |
| Sequence 4 from patent U.S. Pat. No. 7,241,881 467 aa protein | ABU34843.1 GI: 155711984 |
| Sequence 2 from patent U.S. Pat. No. 7,241,881 397 aa protein | ABU34842.1 GI: 155711983 |
| olfactory receptor-like receptor [Bombyx mori] 407 aa protein | BAD89570.1 GI: 59796989 |
| olfactory receptor-like receptor [Bombyx mori] 417 aa protein | BAD89569.1 GI: 59796987 |
| olfactory receptor-like receptor [Bombyx mori] 424 aa protein | BAD89568.1 GI: 59796985 |
| olfactory receptor-like receptor [Bombyx mori] 439 aa protein | BAD89567.1 GI: 59796983 |
| putative chemosensory receptor 2, partial [Tenebrio molitor] 206 aa protein | CAD88247.1 GI: 32400236 |
| putative chemosensory receptor 2, partial [Calliphora vicina] 208 aa protein | CAD88246.1 GI: 32400234 |

TABLE 3-continued

Odorant receptors.

| Gene Name | Accession Number |
|---|---|
| putative chemosensory receptor 2, partial [Apis mellifera] 210 aa protein | CAD88245.1 GI: 32399813 |
| putative chemosensory receptor 2 [Bombyx mori] 472 aa protein | CAD88206.1 GI: 32399811 |

TABLE 4

OR1A1 (*Homo sapiens*)
MOR106-1 (*Mus musculus*)
OR51E1 (*Homo sapiens*)
OR10J5 (*Homo sapiens*)
OR51E2 (*Homo sapiens*)
MOR9-1 (*Mus musculus*)
MOR18-1 (*Mus musculus*)
MOR272-1 (*Mus musculus*)
MOR31-1 (*Mus musculus*)
MOR136-1 (*Mus musculus*)

Example 2 Detection System for Identification of Volatile Compounds and Determination of Source Location In some embodiments, a detection system comprising multiple cell-based sensor panels positioned at known locations in a space (e.g., a room, passageway, parking garage, or other place) may be used to monitor air samples for the presence of volatile compounds, e.g., volatile markers of or taggants used in the manufacture of explosive materials. Each sensor panel may be assigned a set of known 3-dimensional coordinates (x, y, z) which may be used by a sensor signal processing algorithm to not only detect and identify one or more volatile compounds of interest, but also to determined the location of the source of the volatile compound(s) within the space. As described above, the signal processing algorithm can be used to differentially detect a gradient of a compound and correlate the local compound concentration with the (x, y, z) coordinates of the sensor panel at each location, thus, permitting generation of a 3-dimensional map. By collecting multiple readings over time, a 4-dimensional map (x, y, z, t) (where t=time) may be created such that a detection system can map increasing and decreasing chemical concentrations across space and time. By tracking an increase in compound concentration over time, one can detect a path for the chemical gradient, thereby permitting the detection of the location of a fixed position chemical source, or the mapping of the path of a moving chemical source.

Such detection systems may be applied to a variety of different scenarios, such as detection of explosives in an airport environment. Examples of specific airport detection scenarios in which the disclosed detection systems may be applied include: (a) parking garage locations with outside airflow; (b) passenger entry-way vestibules; (c) passenger boarding pass and baggage check-in counters; (d) passenger screening in open spaces or passages by the Transportation Security Administration (TSA); (e) gate open spaces; (f) boarding or off-loading passenger gate pathways onto an airplane; (g) train station platforms within or entering the airport, including spaces that comprise multi-level (elevator, escalator or stairway) transport.

In some cases, the airport environment may be akin to that in other large buildings with public access, e.g., shopping malls, train stations, or office building lobbies. These locations are similar in that they typically comprise large enclosed spaces, often with significant human traffic flow, which cannot be easily monitored due to excessive movement and/or the size of the open space.

In some embodiments, a 3-dimensional grid of sensor panels may be located around the entire airport space. In some embodiments a 3-dimensional grid of sensor panels may be confined to localized areas of the airport. For rough position coordinate estimates, the GPS grid may be used, but the resolution of the disclosed detection systems for location of an odorant source (which is determined in part by the accuracy of determining the position coordinates of the sensor panels) may be more fine-grained than that achievable by Global Positioning System (GPS) readings (approximately 3-4 meters horizontally). Therefore, a higher resolution mapping of the grid of sensor panels within the space may be required. For example, in some cases, one may be able to identify the locations of the detectors and the odorant source to within about 2 meters in any dimensions. In some cases, one may be able to identify the locations of the detectors and the odorant source to within about 1 meter in any dimension. In some cases, one may be able to identify the locations of the detectors and the odorant source to within about 0.5 meters in any dimension. In some cases, one may be able to identify the locations of the detectors and odorant source to within about 0.1 meters in any dimensions. In some cases, one may be able to identify the locations of the detectors and the odorant source to within about 0.05 meters in any dimension. In some cases, one may be able to identify the locations of the detectors and odorant source to within about 0.01 meters in any dimension, or better.

Consider a vestibule through which a stream of passengers may enter an airport. The vestibule may comprise a long hallway, or a short entryway with revolving doors, or a short passageway with two sets of sliding glass doors (one at each end). As a specific example, consider a 3-dimensional grid of sensor panels assigned to a passageway. This passageway may be assigned ID=#23 in the detection system's system control software. Coordinates of the sensor panel detectors may be entered into the system control software in units of meters. Three evenly spaced detectors may be placed along the passageway. Both the 3D coordinates and the gross location of each of the detectors may be entered in the system software. For example, detector #1 may be located in southwest entryway #23 at location (x=75, y=190, z=1); detector #2 may be located in southwest entryway #23 at location (x=75, y=192, z=1); and detector #3 may be located in southwest entryway #23 at location (x=75, y=194, z=1).

These coordinates indicate that detectors are spaced about 2 meters apart (based on 2 m increments in y) and about 1 meter above the floor of the passage way #23.

Each sensor panel or detector may comprise an array of cell-based sensors, each of which comprises an array of neurons, with different odorant receptors assigned to different locations on the array. The detector may comprise a certain amount of redundancy such that a given receptor may reside in more than one neuron or more than one position on the array. In some cases, a single receptor may be over-expressed in each neuron. This may permit successful mapping of the neuron activation back to a single odorant receptor, and thus to a single pre-determined set of odorants that may be detected by that receptor. Each detector array may be trained for different odorants such that a specific signal pattern across receptors on the array may be associated with each odorant. Some receptors may be more specific for binding of a specific compound, and thus may specifically detect some odorants. Other receptors may be more general or promiscuous in their binding of odorants, and thus may exhibit activation responses to a wider range of odorants. The pattern of electrical signals induced upon binding of specific odorants can be determined for the detector array beforehand.

In some cases, a specific odorant may bind to a set number of receptors at different levels based on concentration. For example, when tested during training, DNT (dinitrotoluene, a chemical precursor of the explosive trinitrotoluene (TNT)) may bind to receptors 7, 9, and 47 on the array, thereby providing a DNT fingerprint on a specific detector array. Because these detectors may be able to detect sub-threshold (sub-action potential threshold) binding, one can map different signals to different concentrations of the Volatile compound detected.

In some cases, a single detector array may be able to detect binding events for the odorant(s) of interest. For example, in some cases, an odorant may bind to detector array neurons 7, 9, and 47, thereby allowing one to refer to a lookup table and determine that the odorant may be likely DNT. Locally, with that single detector, one can predict a likelihood that DNT was detected.

In determining the likelihood of having detected a specific compound, one can give a higher score or weighting factor to responses measured for narrowly-focused odorant receptors that are more likely to respond to the specific odorant, while factoring in partial scores or additional weighting factors for responses measured for more promiscuous receptors.

In some cases, e.g., where the detection system comprises multiple detectors connected to a single computing source (such as a server), one may detect the odorant at different locations and at different concentrations over time, thereby tracking the source of the odorant.

For example, if a passenger carrying TNT-based explosives were to enter the passageway at time t=0 seconds, then:

At t=5 seconds, when the passenger may be passing detector #1, a detection event for DNT may occur by observing increased signal for neurons 7, 9 and 47. The server can detect the event.

At t=10 seconds, when the passenger may be passing detector #2, a detection event may occur for detector #2.

At t=15 seconds, when the passenger may be passing detector #3, a detection event may occur for detector #3.

A computer server tracking signal activity at detectors #1, #2 and #3 may be alerted as the detectors respond to the presence of the odorant compound, and the algorithm may trigger an alert that an initial detection event has occurred in vestibule #237 at coordinates (75, 190, 1), after which it may perform a search for detection events for nearby detectors over a period of seconds such that a vector of increased detection events nearby (due to increasing local concentration of the DNT) can be tracked. As soon as a second detection event is identified by a nearby detector, the highest level of alert is triggered since there is little likelihood that a false positive event has occurred.

From the time-stamped data for the detection events, the computer can detect a direction of travel for the passenger carrying the explosive, and security measures may be taken by airport personnel (e.g., more detailed, directed video surveillance, locking of doors, and alerts to personnel directing them to intercept potential passengers).

"Smart Tunnel" configuration: In some embodiments, the detection systems described herein may comprise a "smart tunnel" for high-throughput, high-precision detection of explosives and other volatiles carried by passengers at airport security checkpoints. In some embodiments, one wall of the smart tunnel may be populated with several grids of cell-based sensor devices (i.e., bio-electronic chips) that may be able to detect explosive compounds with extremely high precision. The passengers may be proceed down the tunnel past a detection system optimized for delivering volatile compounds emanating from a passenger to the functional detection component of the chip, which may be a genetically engineered neural cell. Airport security personnel may be immediately alerted if a passenger appears to be carrying explosives detected by the cells with the sensor devices. The bioelectronic chips may comprise an array of neurons in contact with or in close proximity to an array of microelectrodes that are capable of capturing the electrical signals generated by the neurons, e.g., action potentials, which constitute a response to a volatile chemical present in the environment. Each neural cell may be engineered to express a single type of odorant receptor that may be specifically responsive to a single kind of ligand. The cell surface receptor, via a series of signaling proteins may internally trigger an action potential by the neuron. This electrical signal from the cell may be measured by the electrode (e.g., as a current or voltage pulse) and then processed by a machine learning back end that determines if the electrical signal pattern generated by the cells constitutes a detection event. In aggregate, the cells may differentially detect an array of compounds or mixtures of compounds, which collectively yield a signal "fingerprint" of detection. In some embodiments, for example, the tunnel may comprise four sensor panels, each with an adaptive sensitivity parameter to ensure robust detection of a range of volatile compounds of interest with a low rate of false positive events. Because this detection system takes advantage of the specificity of receptor-ligand binding interactions and the signal amplification that is inherent in intracellular signaling pathways, it may be able to detect compounds of interest at concentrations down to the parts per billion (ppb) range, with extremely high selectivity, such as concentrations of less than about 500 ppb, less than about 200 ppb, less than about 100 ppb, less than about 50 ppb, less than about 10 ppb, less than about 1 ppb, or less than about 0.1 ppb.

Tunnel design and four stage voting system: The passenger may proceed down a tunnel that may be, for example, about 1 meter wide past four separate sensor panels, each with one 'vote' as to whether or not the passenger may be carrying an explosive. In order for a detection event to be triggered, the detection system may require that all four panels form a positive consensus. Each panel may comprise an m×n grid of cell-based microelectrode array sensors. Each cell-based sensor device within the sensor panel may be engineered to be responsive to one compound of interest, and may comprise at least 128 separate neurons genetically engineered to express a cell surface odorant receptor that can bind to the explosive in question. That is, all or a portion of those neurons may be dedicated to responding to one species of volatile compound. If a significant proportion of these neurons begin firing in response to the volatile compounds or particulates emanating from a specific tunnel occupant, then the system may have detected a compound of interest. The next cell-based microelectrode array sensor in the grid may be comprised of neurons expressing a different set of receptors, which respond to a different compound. In this manner, each of the cell-based sensors in the array of sensor comprising the sensor panel may be designed and/or optimized for detection of a particular compound of interest, and each sensor panel may be able to respond to all compounds of interest.

The sensor panels may be intelligent, and may adapt in response to information from the preceding sensor panel. If the first sensor panel indicates that the passenger is likely to be carrying an explosive (i.e., one of the cell-based microelectrode array sensors has reached a positive consensus about one of the m×n detectable compounds), then the sensitivity of the second sensor panel can be immediately increased to verify this result. Following this second confirmation, the sensitivity can then be increased in the third and fourth subsequent sensor panels. As noted above, the sensitivity of individual cell-based sensor devices, and thus of the sensor panel comprising said devices, may be adjusted in a variety of ways, e.g., by addition of odorant binding proteins or compound stabilization additives in the culture medium bathing the cells. In some embodiments, sensitivity may also be adjusted by changing the threshold for signaling an alert, by altering airflow across the sensor devices of the panel, or by adjusting other environment control systems (e.g., temperature, humidity, electrical stimulation, etc.).

If the first sensor panel doesn't detect a compound of interest, the sensitivity of the second panel may remain unchanged. However, if the second sensor panel makes a positive detection, then the sensitivity of the third sensor panel may be updated to verify the result of the second sensor panel. This procedure may eliminate false positives and may ensure robust and reliable detection of every compound of interest that the tunnel has been designed to respond to.

Cell-based sensor devices: Each single sensor panel within the smart tunnel may comprise a grid of cell-based sensor devices (i.e., cell-based microelectrode array sensors), as previously discussed. Each cell-based microelectrode array sensor comprises a grid of neural cells which have been transfected with exogenous odorant receptors that are known to be responsive to a particular volatile or explosive. Non-limiting examples of volatile markers for and taggants used with explosive materials are listed in Table 5. The odorant receptors are proteins that the cell is constantly generating and trafficking to the cell surface. When the correct compound of interest binds of form a complex with the receptor protein, a bio-amplification cascade is triggered within the cell in which the signal is amplified by several thousand fold, eventually resulting in the depolarization of the cellular membrane by calcium and potassium ion exchange. This depolarization appears as an electrical signal called an action potential that can be detected by the one or more microelectrodes positioned within each chamber of the cell-based sensor device and translated into a digital signal by an analog to digital converter. From there, machine learning-based back-end signal processing comprising the use of, for example, a support vector machine, will determine if the level of firing is sufficient to constitute a detection event. The neurons are expected to have a low level of background action potential firing even in the absence of any appropriate stimuli. This will be taken as a baseline, and an appropriate level of deviation above this baseline will constitute the detection of the compound of interest. In some cases, the type of neuron or excitable cell used to express the odorant receptors may be selected or modified, e.g., genetically modified, to minimize background action potential firing. By using separate dedicated cell-based microelectrode array sensors for each individual compound of interest, security personnel will immediately alerted to the fact that a passenger is carrying or has come into contact with an explosive, but will also be informed as to precisely which explosive has been detected. In the event that the passenger is carrying or has been in contact with multiple explosives, it is therefore trivial for the smart tunnel to identify all of them simultaneously.

TABLE 5 non-limiting examples of volatile markers and taggants for explosive materials.

| Compound | Description |
| --- | --- |
| 2,3-dimethyl-2,3-dinitrobutane (DMDNB/DMNB)) | Taggant used in the U.S. for marking plastic explosives (detectable by dogs at 0.5 ppb in air) |
| ethylene glycol dinitrate (EGDN) | Taggant used to mark Semtex |
| ortho-mononitrotoluene (o-MNT) | Taggant used for marking plastic explosives |
| para-mononitrotoluene (p-MNT) | Taggant used for marking plastic explosives |
| Dinitrotoluene (DNT) | Chemical precursor of the explosive trinitrotoluene (TNT) |
| Trinitrotoluene (TNT) | Explosive material |
| Triacetone triperoxide (TATP) | Trimer of acetone peroxide (AP) - explosive material |

Air sampling: As discussed previously, in many embodiments an air-sampling device may be integrated with the cell-based sensor devices or sensor panels, or may be used in conjunction with said devices and panels to facilitate efficient transfer of volatile compounds from air within the tunnel into the liquid medium bathing the cells within the sensors. In a first option, neural sensor devices such as those shown in FIGS. 6A-B may be mounted on a wall or ceiling of the tunnel, and may comprise a semi-permeable gas exchange membrane that allows diffusible transport of volatile compounds through the membrane to the cell medium.

In a second option, as shown in FIG. 7, the air surrounding the current tunnel occupant may be drawn into a gas perfusion device and bubbled through an exact volume of cellular media, thus trapping the compound of interest. Turbines or fans may collect air samples from the vicinity of the current tunnel occupant as he or she enters the tunnel, and deliver it to the gas perfusion device, where it is bubbled through the liquid medium at a rate of about 2 liters per second. Through the use of a microfluidics-based perfusion system, the medium currently residing in the cell-based sensor device, which corresponds to the air sample drawn for the last tunnel occupant, may be flushed out and replaced with the medium now containing volatile or particulate matter from the air sample drawn for the current tunnel occupant. This air sampling, gas perfusion, and medium exchange process may occur in cycles lasting less than about 20, 15, 10, 9, 8, 7, 6, 5, 4, 3, 2, 1, 0.5, or 0.1 seconds, and the process may be repeated for each sensor panel that the passenger may walk past. This may ensure that volatile compounds of interest are efficiently introduced into the medium and reach the cell surface, as the diffusion path length from source to cell surface through the liquid medium has been identified a potentially confounding factor in previous research. The presently disclosed systems and method may eliminate this problem.

A third option for air sampling may be to perfuse the air surrounding the current tunnel occupant through a solvent rather than cell culture medium (e.g., using a device similar to that illustrated in FIG. 7), where the solvent may be chosen for its ability to dissolve even extremely volatile compounds. For example, this may be a polar aprotic solvent such as dimethyl sulfoxide or acetone, which may be less cytotoxic than other organic solvents, and are known to solvate compounds like TNT well. This compound-containing solution may then be aerosolized via an ultrasonic humidification device which uses high frequency vibration to form a vapor or mist. This vapor can then be blown over the surface of the semipermeable membrane of the cell-based sensor device. In some cases, the medium may not need to be constantly perfused through the sensor device with this approach, but may instead be changed at regular intervals that are determined empirically based on the needs of the cell population. The time course of air sampling, gas perfusion, and medium exchange events may be similar to that described above.

In a fourth option, as shown in the sensor devices illustrated in FIGS. 13A-B, the solvent perfusion/aerosol approach described for option 3 may be modified to pass the compound-loaded vapor over a highly texturized gas exchange membrane which, like the nasal cavity of any smelling organism, can form air currents and eddies which may facilitate entrapment of dissolved compounds or particulates, thereby increasing dwell time and the overall proportion of volatiles that diffuse through the membrane into the medium bathing the cells. This bio-inspired architecture for the semi-permeable gas exchange membrane may increase the proportion of compounds or particulates that end up in the cell medium and may therefore facilitate detection by the cells. In FIGS. 13A-B, medium enters the sensor device via medium inlet 1 and is delivered to the cells within each microwell 5 via microfluidic channels 3, before exiting the device via medium outlet 2. Air samples, or compound-loaded vapor, accesses the semi-permeable gas exchange membrane 7 via openings 4. Each microwell 5 comprises an active electrode region 6 (e.g., comprising one or more electrodes). The sensor device may further comprise an anti-shear stress membrane 8, and a contact for complementary electronics 9.

In another approach to air sampling, a passenger may walk past a large air-sampling device such as that illustrated in FIGS. 5A-B that comprises a series of microchannels containing only cell culture medium and covered by a very thin semi-permeable gas exchange membrane, from which the medium outlet may feed into a cell-based microelectrode array sensor device or sensor panel positioned downstream for detection. The purpose of this air-sampling device is to maximize the surface area over which volatile compounds or particulates emanating from a passenger passing through the tunnel can diffuse into the medium. In some cases, for example, the total amount of cell culture medium needed to fill the air-sampling device may be about 1 ml. The panel may be approximately 20 cm×20 cm×25 microns deep, for example, so that even very low concentrations of the volatile compound have a high probability of diffusion across the gas exchange membrane into the cell culture medium. This medium may then be pumped, e.g., via a microfluidic perfusion system, into the cell-based microelectrode array sensor device or panels positioned downstream. In this approach, the cell-based sensor devices or sensor panels may not require an integrated gas exchange membrane as the compounds or particulates of interest may already be dissolved by the medium.

FIG. 14 provides a non-limiting illustration of one embodiment the entire smart tunnel, including a four stage detection system that incorporates the neural cell-based sensor devices.

FIG. 15 shows a top view of one stage of the four stage detection system illustrated in FIG. 14. Air intake 2 is mounted on one wall is 1 of the tunnel. An air pump 3 delivers air samples drawn from the tunnel to a liquid/gas exchange apparatus 5. A cell culture medium reservoir 4 is also connected to the liquid/gas exchange apparatus 5. Air passing through the liquid/gas exchange apparatus is vented through air exhaust is 6, while the compound-containing medium is delivered to the bioelectric sensor panel 7. A computer and/or connections to other system units are interfaced with the detection system through connector 8. The waste medium is collected in reservoir 9. In this system configuration, ambient air containing volatile compounds of interest can be injected into a small mixing chamber where, for example, a device atomizes the gas with the medium. The resultant vapor may then be recondensed and injected into the medium reservoir of an impermeable (sealed) cell-based sensor panel. Top and side views of one such neural sensor panel, comprising an m×n grid (e.g., a 3×6 grid) of cell-based microelectrode array sensors, each of which further comprise genetically-engineered neurons in contact with a microelectrode array that are responsive to a range of explosive or volatile compounds, are shown in FIGS. 4A-B.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

We claim:

1. A method for detecting and identifying a volatile compound in an air sample, comprising:

providing an air sample to a cell-based sensor device having a plurality of chambers, wherein each chamber contains a liquid medium and a plurality of cells expressing one or more cell-surface receptors, the air sample provided to a first side of a membrane and the cells on a second side of the membrane, the membrane allowing for diffusion of the volatile compound from the air sample through the membrane and into the liquid medium;

using an electrode in each chamber to measure an electrical signal resulting from a binding event between one or more of the cell-surface receptors of the cell and the volatile compound present in the air sample; and processing the measured electrical signal to detect and identify the volatile compound.

2. The method of claim 1 wherein the cell is a neuron.

3. The method of claim 2 wherein the electrical signal comprises an action potential.

4. The method of claim 2 wherein the electrical signal comprises an excited electrical signal level that is below a threshold for an action potential.

5. The method of claim 2 wherein the electrical signals comprise a cell membrane depolarization.

6. The method of claim 2 wherein a cell in each of the plurality of chambers is genetically-modified to express the one or more cell-surface receptors.

7. The method of claim 1 wherein the membrane is a polytetrafluoroethylene membrane.

8. A method for detecting and identifying a volatile compound in an air sample, comprising:

providing an air sample to at least one sensor panel including one or more cell-based sensor devices, each cell-based sensor device having a plurality of chambers, each chamber containing a liquid medium and a plurality of cells on a membrane, the cells expressing one or more cell-surface receptors, the air sample provided to a first side of the membrane and the cells on a second side of the membrane, the volatile compound from the air sample diffusing through the membrane and into the liquid medium;

positioning an electrode in each chamber to measure an electrical signal resulting from a binding event between one or more of the cell-surface receptors and the volatile compound from the air sample; and the electrodes electrically connected to a controller configured to receive the electrical signals, the controller storing and processing a pattern of electrical signals associated with the volatile compound to identify the volatile compound.

9. The method of claim 8 further comprising positioning a first sensor panel at a first location and positioning a second sensor panel at a second location, and determining a spatial location of a source of the volatile organic compound.

10. The method of claim 8 wherein the cells are bathed in the liquid medium.

11. The method of claim 8 further comprising injecting pressurized air into a closed mixing chamber to increase a partial pressure of the volatile organic compound above an injection liquid, and subsequently injecting at least some of the injection liquid into the plurality of chambers in one or more of the sensor panels.

12. The method of claim 8 further comprising heating the liquid medium before exposing the liquid medium to the air sample.

13. The method of claim 8 further comprising mixing the air sample with a solvent and subsequently mixing the solvent with the liquid medium.

14. The method of claim 8 wherein the membrane is a polytetrafluoroethylene membrane.

* * * * *